(12) United States Patent
Pinney et al.

(10) Patent No.: US 7,429,681 B2
(45) Date of Patent: Sep. 30, 2008

(54) COMBRETASTATIN ANALOGS WITH TUBULIN BINDING ACTIVITY

(75) Inventors: Kevin G. Pinney, Woodway, TX (US); Madhavi Sriram, Waco, TX (US)

(73) Assignee: Baylor University, Waco, TX (US)

( * ) Notice: Subject to any disclaimer, the term of this patent is extended or adjusted under 35 U.S.C. 154(b) by 0 days.

(21) Appl. No.: 11/454,074

(22) Filed: Jun. 14, 2006

(65) Prior Publication Data

US 2006/0293394 A1    Dec. 28, 2006

Related U.S. Application Data

(60) Provisional application No. 60/690,689, filed on Jun. 14, 2005.

(51) Int. Cl.
*C07C 49/172* (2006.01)
*A01N 35/06* (2006.01)

(52) U.S. Cl. ...................... 568/325; 514/678

(58) Field of Classification Search ................ 514/678, 514/721; 568/308, 325, 328, 633
See application file for complete search history.

(56) References Cited

U.S. PATENT DOCUMENTS 3,859,356 A     1/1975   Houlihen et al. .......... 260/570.9
7,011,926 B2 *  3/2006   Hsieh ........................ 430/296

FOREIGN PATENT DOCUMENTS

GB    1 520 579       8/1978
WO    WO 00/48606    8/2000
WO    WO 01/68654 A2  9/2001

OTHER PUBLICATIONS

Sangwan et al. "Studies in Antifertility Agents: part XXXIII—synthesis of 1,2- trans-l-[p-(beta-pyrrolidinoethoxy)phenyl]-2-benzyl-7-methoxybenzosuberan", 1981, Indian journal of Chemistry, vol. 20B, pp. 140, 141.*
Humphreys et al. Novel Aromatic systems. Part X. some Aspects of the chemistry of 2,3,-dihydroxybenzocycloheptenes), 1972, Royal society of Chemistry, Journal of Chemical society, Perkins Trans. 1, pp. 722-726.*
Magarian et al., "The medicinal chemistry of nonsteroidal antiestrogens: a review", *Curr. Med. Chem.*, 1:61-104 (1994).
Nakayama et al., "Benzyne-induced fragmentation of 1,3-oxathiolanes. A novel method for deprotection of carbonyl groups. Preparation of phenyl vinyl sulfides and 1,2-carbonyl transposition", *Tetrahedron Lett.*, 26(18):2195-2198 (1985).
Sangwan et al., "Studies in antifertility agents: part XXXIII—synthesis of I,2-trans-I-[p-(β-pyrrolidinoethoxy)phenyl]-2-benzyl-7-methoxybenzosuberan", *Indian J. Chem.*, 20B(2):140-143 (1981).
International Search Report for PCT/US2006/023251, mailed May 8, 2007.

* cited by examiner

*Primary Examiner*—Yvonne Eyler
*Assistant Examiner*—Yate K Cutliff
(74) *Attorney, Agent, or Firm*—Karen E. Flick

(57) ABSTRACT

Analogs of combretastatin have been discovered which demonstrate impressive cytotoxicity as well as a remarkable ability to inhibit tubulin polymerization. Such compounds are excellent clinical candidates for the treatment of cancer in humans. In addition, certain of these ligands, as pro-drugs, may well prove to be tumor selective vascular targeting chemotherapeutic agents or to have vascular targeting activity resulting in the selective prevention and/or destruction of nonmalignant proliferating vasculature.

15 Claims, 13 Drawing Sheets

COMBRETASTATIN ANALOGS WITH TUBULIN BINDING ACTIVITY

RELATED APPLICATIONS

This application claims priority to U.S. Provisional Application 60/690,689, filed Jun. 14, 2005, entitled "Combretastatin Analogs with Tubulin Binding Activity". The entire content of the above-referenced application is incorporated herein by reference.

BACKGROUND OF THE INVENTION

The cytoskeletal protein tubulin is among the most attractive therapeutic drug targets for the treatment of solid tumors. A particularly successful class of chemotherapeutics mediates its anti-tumor effect through a direct binding interaction with tubulin. This clinically promising class of therapeutics, called tubulin binding agents or anti-tubulin agents, exhibit potent tumor cell cytotoxicity by efficiently inhibiting the assembly of $\alpha,\beta$-tubulin heterodimers into microtubule structures that are required to facilitate mitotic cell division (Li & Sham, *Expert Opin. Ther. Patents.*, 2002).

Currently, the most widely recognized and clinically useful anti-tubulin chemotherapeutics agents are the Vinca Alkaloids, such as Vinblastine and Vincristine (Owellen et al., *Cancer Res.*, 1976) along with Taxanes such as Taxol (Schiff et al., *Nature*, 1979). Additionally, natural products such as Rhizoxin (Rao et al., *Tetrahedron Lett.*, 1992), the Combretastatins (Pettit et al., *Can. J. Chem.*, 1982), Curacin A (Gerwick et al., *J. Org. Chem.*, 1994), Podophyllotoxin (Coretese et al., *I. Biol. Chem.*, 1977), Epothilones A and B (Nicolau et al., *Nature*, 1997), Dolastatin-10 (Pettit et al., *J. Am. Chem. Soc*, 1987), and Welwistatin (Zhang et al., *Molecular Pharmacology*, 1996), as well as certain synthetic analogs including Phenstatin (Pettit G R et al., *J. Med. Chem.*, 1998), 2-styrylquinazolin-4(3H)-ones ("SQOs", Jiang et al., *J. Med. Chem.*, 1990), highly oxygenated derivatives of cis- and trans-stilbene, and dihydrostilbene (Cushman et al., *J. Med. Chem.*, 1991) are all known to mediate tumor cytotoxic activity through a mode of action that includes tubulin binding and subsequent inhibition of mitosis.

Normally, during the metaphase of cell mitosis, the nuclear membrane has broken down and tubulin is able to form centrosomes (also called microtubule organizing centers) that facilitate the formation of the microtubule spindle apparatus to which the dividing chromosomes become attached. Subsequent assembly and disassembly of the spindle apparatus mitigates the separation of the daughter chromosomes during anaphase such that each daughter cell contains a full complement of chromosomes. As antiproliferatives or antimitotic agents, tubulin binding agents exploit the relatively rapid mitosis that occurs in proliferating tumor cells. By binding to tubulin and inhibiting the formation of the spindle apparatus in a tumor cell, the tubulin binding agent can cause significant tumor cell cytotoxicity with relatively minor effects on the slowly dividing normal cells of the patient.

The exact nature of tubulin binding site interactions remains largely unknown, and they definitely vary between each class of tubulin binding agent. Photoaffinity labeling and other binding site elucidation techniques have identified three key binding sites on tubulin: 1) the Colchicine site (Williams et al., *J. Biol. Chem.*, 1985); 2) the Vinca Alkaloid site (Safa et al., *Biochemistry*, 1987); and 3) a site on the polymerized microtubule to which taxol binds (Lin et al., *Biochemistry*, 1989). An important aspect of this work requires a detailed understanding, at the molecular level, of the "small molecule" binding domain of both the $\alpha$ and $\beta$ subunits of tubulin. The tertiary structure of the $\alpha,\beta$ tubulin heterodimer was reported in 1998 by Downing and co-workers at a resolution of 3.7 Å using a technique known as electron crystallography (Nogales et al., *Nature*, 1998). This brilliant accomplishment culminated decades of work directed toward the elucidation of this structure and should facilitate the identification of small molecule binding sites, such as the colchicine site, using techniques such as photoaffinity and chemical affinity labeling (Chavan et al., *Bioconjugate Chem.*, 1993; Hahn et al., *Photochem. Photobio L*, 1992).

Further significance is given to new drugs that bind to the colchicine site since it has recently been shown that many tubulin binding agents also demonstrate activity against malignant proliferating tumor vasculature, as opposed to the tumor itself. Antivascular chemotherapy is an emerging area of cancer chemotherapy which centers on the development of drugs that target the proliferation of the vasculature that supports tumor growth. Much of the research in anti-vascular cancer therapy has focused on understanding the process of new blood vessel formation, known as angiogenesis, and identifying anti-angiogenic agents which inhibit the formation of new blood vessels. Angiogenesis is characterized by the proliferation of tumor endothelial cells and generation of new vasculature to support the growth of a tumor. This growth is stimulated by certain growth factors produced by the tumor itself. One of these growth factors, Vascular Endothelial Growth Factor ("VEGF"), is relatively specific towards endothelial cells, by virtue of the restricted and up-regulated expression of its cognate receptor. Various anti-angiogenic strategies have been developed to inhibit this signaling process at one or more steps in the biochemical pathway in order to prevent the growth and establishment of the tumor vasculature. However, anti-angiogenic therapies act slowly and must be chronically administered over a period of months to years in order to produce the desired effect.

Vascular Targeting Agents ("VTAs"), also known as vascular disrupting agents or vascular damaging agents, are a separate class of antivascular chemotherapeutics. In contrast to anti-angiogenic drugs which disrupt the new microvessel formation of developing tumors, VTAs attack solid tumors by selectively targeting the established tumor vasculature and causing extensive shutdown of tumor blood flow. A single dose of a VTA can cause a rapid and selective shutdown of the tumor neovasculature within a period of minutes to hours, leading eventually to tumor necrosis by induction of hypoxia and nutrient depletion. This vascular-mediated cytotoxic mechanism of VTA action is quite divorced from that of anti-angiogenic agents, which inhibit the formation of new tumor vascularization rather than interfering with the existing tumor vasculature. Other agents have been known to disrupt tumor vasculature, but differ in that they also manifest substantial normal tissue toxicity at their maximum tolerated dose. In contrast, genuine VTAs retain their vascular shutdown activity at a fraction of their maximum tolerated dose. It is thought that tubulin-binding VTAs selectively destabilize the microtubule cytoskeleton of tumor endothelial cells, causing a profound alteration in the shape of the cell which ultimately leads to occlusion of the tumor blood vessel and shutdown of blood flow to the tumor (Kanthou et al., *Blood*, 2002).

Combretastatin A4 phosphate prodrug (CA4P) is one of the leading new candidates from among a relatively small collection of known world compounds with vascular targeting activity (U.S. Pat. No. 5,561,122; Chaplin et al., *Anticancer Res.*, 1999; Tozer et al., *Cancer Res.*, 1999; Pettit and Rhodes, *Anti-Cancer Drug Des.*, 1998; Iyer et al., *Cancer Res.*, 1998;

Dark et al., *Cancer Res.,* 1997). Its parent phenol compound, Combretastatin A-4 (CA4) was discovered by Professor George R. Pettit (Arizona State University) as an isolate from South African bush willow (*Combretum caffrum*) in the 1970s. CA4 is a potent inhibitor of tubulin polymerization and binds to the colchicine site on β-tubulin. Interestingly, CA4 itself does not demonstrate destruction of tumor vasculature, while CA4P is very active in terms of tumor vasculature destruction. Therefore, the phosphate ester portion of CA4P undergoes dephosphorylation to reveal the potent tubulin binder CA4 that destroys the tumor cell through an inhibition of tubulin polymerization.

CA4P is currently the lead drug in a group of tubulin-binding VTAs under clinical development. Other tubulin binding VTAs that have been discovered include the colchicinoid ZD6126 (Davis et al., *Cancer Research,* 2002) and the Combretastatin analog AVE8032 (Lejeune et al., *Proceedings of the AACR.,* 2002). Despite these advances, an aggressive chemotherapeutic strategy for the treatment and maintenance of solid tumor cancers continues to rely on the development of architecturally new and biologically more potent compounds. The present invention addresses this urgent need by providing a structurally novel class of tubulin binding agent compositions with potent antiproliferative activity and tumor cell cytotoxicity.

SUMMARY OF THE INVENTION

The present invention relates to a discovery of Combretastatin analogs which function as tubulin binding agents capable of inhibiting tubulin assembly and tumor cell proliferation. These Combretastatin analogs result from the judicious combination of a non-tubulin binding molecular template, suitably modified with structural features such as hydroxyl moieties and arylalkoxy groups. Furthermore, the invention provides compounds useful in the treatment, prevention or amelioration of one or more symptoms of vascular proliferative disorders and neoplastic diseases. The compounds of the invention are also useful in reducing the flow of blood to at least a portion of a neoplastic region, and for inhibiting tubulin polymerization.

In one general aspect, the present invention provides a Combretastatin analog of the following general formula I:

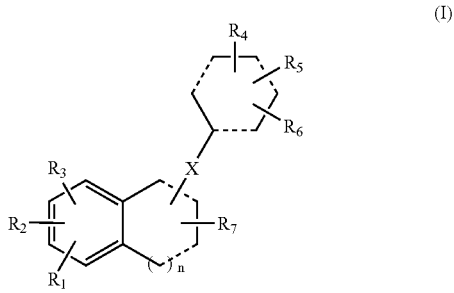

(I)

or a pharmaceutically acceptable salt thereof, wherein
the dashed lines indicate a single or double bond;
$R_1$, $R_2$, $R_3$, $R_4$, $R_5$, $R_6$ and $R_7$ are each, independently, selected from the group consisting of H, halogen, lower alkyl, lower alkoxy, hydroxyl, amine, phosphate, phosphoramidate, and amino acid acyl group;
X is selected from the group consisting of a single bond, $CH_2$, O, S, N(H), and C(O); and n is 0, 1, 2 or 3.

In one embodiment of Formula I, $R_1$, $R_2$, $R_3$, $R_4$, $R_5$, $R_6$ and $R_7$ are each, independently, selected from the group consisting of H, lower alkoxy, hydroxyl, phosphate and phosphoramidate. In another embodiment of Formula I, X is a single bond. In another embodiment of Formula I, n is 2 or 3.

In another general aspect, the present invention provides a Combretastatin analog of the following general formula II:

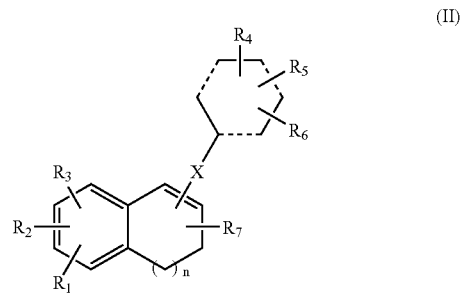

(II)

or a pharmaceutically acceptable salt thereof,
wherein the dashed lines indicate a single or double bond;
$R_1$, $R_2$, $R_3$, $R_4$, $R_5$, $R_6$ and $R_7$ are each, independently, selected from the group consisting of H, halogen, lower alkyl, lower alkoxy, hydroxyl, amine, phosphate, phosphoramidate, and amino acid acyl group;
X is selected from the group consisting of a single bond, $CH_2$, O, S, N(H), and
C(O); and n is 0, 1, 2 or 3.

In another embodiment of Formula II, $R_1$, $R_2$, $R_3$, $R_4$, $R_5$, $R_6$ and $R_7$ are each, independently, selected from the group consisting of H, lower alkoxy, hydroxyl, phosphate and phosphoramidate. In yet another embodiment of Formula II, X is a single bond. In another embodiment of Formula II, $R_1$, $R_2$ and $R_3$, are each, independently, selected from the group consisting of H, $OCH_3$, phosphate and OH. In still another embodiment of Formula II, $R_4$, $R_5$ and $R_6$, are each, independently, selected from the group consisting of H, $OCH_3$, phosphate and OH. In still another embodiment of Formula II, $R_7$ is H. In still another embodiment of Formula II, n is 2 or 3.

In another general aspect, the present invention provides a Combretastatin analog of the following general formula IIa:

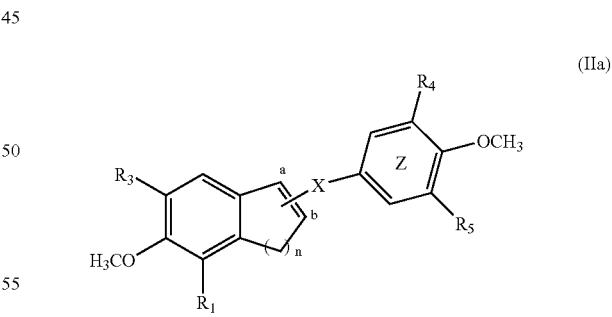

(IIa)

or a pharmaceutically acceptable salt thereof,
wherein the phenyl ring "Z" is bonded to either carbon "a" or "b";
$R_1$, $R_3$, $R_4$ and $R_5$ are each, independently, selected from the group consisting of H, lower alkoxy, hydroxyl, and phosphate;
X is selected from the group consisting of a single bond and C(O); and
n is 1, 2, 3 or 4.

In one embodiment of formula IIa, $R_4$ and $R_5$ are $OCH_3$. In another embodiment of Formula IIa, n is 1. In another embodiment of Formula IIa, n is 3. In another embodiment of Formula IIa, n is 4.

In another general aspect, the present invention provides a Combretastatin analog of the following general formula IIb:

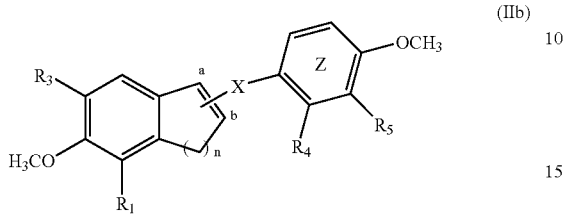

(IIb)

or a pharmaceutically acceptable salt thereof, wherein the phenyl ring "Z" is bonded to either carbon "a" or "b";

$R_1$, $R_3$, $R_4$ and $R_5$ are each, independently, selected from the group consisting of H, lower alkoxy, hydroxyl, and phosphate;

X is selected from the group consisting of a single bond and C(O); and n is 1, 2, 3 or 4.

In one embodiment of formula IIb, $R_4$ is H or OH, and $R_5$ is OH.

In particular embodiments of formula IIa or IIb, $R_1$ and $R_3$ are H. In other embodiments of formula IIa or IIb, $R_1$ is OH and $R_3$ is H. In yet other embodiments of formula IIa or IIb, $R_1$ and $R_3$ are $OCH_3$. In another embodiment of Formula IIb, n is 1. In another embodiment of Formula IIb, n is 3. In another embodiment of Formula IIb, n is 4.

In another general aspect, the present invention provides a Combretastatin analog of the following general Formula III:

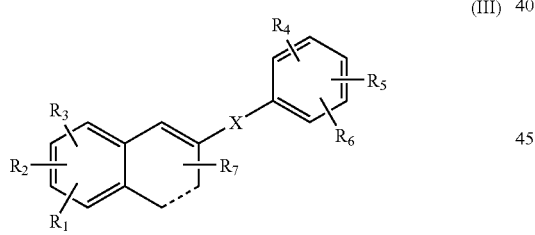

(III)

or a pharmaceutically acceptable salt thereof, wherein:

the dashed line indicates a single or double bond;

X is selected from the group consisting of a single bond, $CH_2$, O, S, N(H), and C(O);

and $R_1$, $R_2$, $R_3$, $R_4$, $R_5$, $R_6$ and $R_7$ are each, independently, selected from the group consisting of H, halogen, lower alkyl, lower alkoxy, hydroxyl, amine, phosphate, phosphoramidate, and amino acid acyl group.

In one embodiment of Formula III, X is a single bond, and $R_1$, $R_2$ and $R_3$, are each, independently, selected from the group consisting of H, $OCH_3$, phosphate and OH. In another embodiment of Formula III, X is a single bond, and $R_4$, $R_5$ and $R_6$, are each, independently, selected from the group consisting of H, $OCH_3$, phosphate and OH.

In another general aspect, the present invention provides a Combretastatin analog of the following general Formula IV:

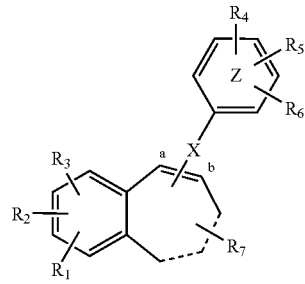

(IV)

or a pharmaceutically acceptable salt thereof, wherein:

the dashed lines independently indicate a single or double bond;

X is selected from the group consisting of a single bond, $CH_2$, O, S, N(H), and C(O);

$R_1$, $R_2$, $R_3$, $R_4$, $R_5$, $R_6$ and $R_7$ are each, independently, selected from the group consisting of H, halogen, lower alkyl, lower alkoxy, hydroxyl, amine, phosphate, phosphoramidate, and amino acid acyl group;

and phenyl ring "Z" is bonded to either carbon "a" or "b."

In another embodiment of Formula IV, the dashed lines are single bonds, X is a single bond, and $R_1$, $R_2$ and $R_3$, are each, independently, selected from the group consisting of H, $OCH_3$, phosphate and OH. In still another embodiment of Formula IV, the dashed lines are single bonds, X is a single bond, and $R_4$, $R_5$ and $R_6$, are each, independently, selected from the group consisting of H, $OCH_3$, phosphate and OH. In still another embodiment of Formula IV, the dashed lines are single bonds, X is a single bond, and the phenyl ring "Z" is bonded to carbon "a." In yet another embodiment of Formula IV, the dashed lines are single bonds, X is a single bond, and phenyl ring "Z" is bonded to carbon "b."

In another general aspect, the present invention provides a Combretastatin analog of the following general formula IVa:

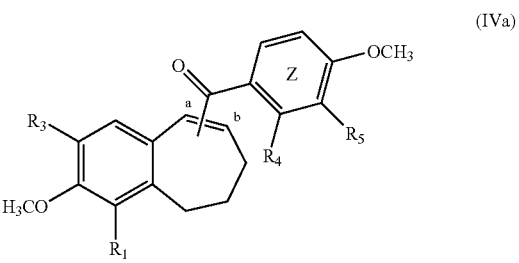

(IVa)

or a pharmaceutically acceptable salt thereof, wherein the phenyl ring "Z" is bonded to either carbon "a" or "b"; and $R_1$, $R_3$, $R_4$ and $R_5$ are each, independently, selected from the group consisting of H, lower alkoxy, hydroxyl, and phosphate.

In one embodiment of formula IVa, $R_1$ and $R_3$ are $OCH_3$. In another embodiment of formula IVa, $R_4$ and $R_5$ are OH. In another embodiment of formula IVa, $R_4$ and $R_5$ are phosphate. In yet another embodiment of formula IVa, phenyl ring "Z" is bonded to carbon "a."

In another general aspect, the present invention provides a Combretastatin analog of the following general formula IVb:

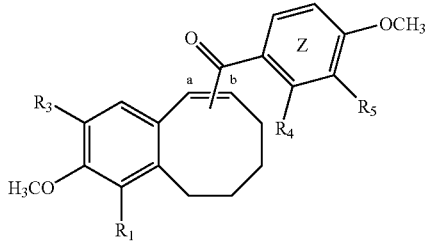

(IVb)

or a pharmaceutically acceptable salt thereof, wherein the phenyl ring "Z" is bonded to either carbon "a" or "b"; and $R_1$, $R_3$, $R_4$ and $R_5$ are each, independently, selected from the group consisting of H, lower alkoxy, hydroxyl, and phosphate.

In one embodiment of formula IVb, $R_1$ and $R_3$ are $OCH_3$. In another embodiment of formula IVb, $R_4$ and $R_5$ are OH. In another embodiment of formula IVb, $R_4$ and $R_5$ are phosphate. In yet another embodiment of formula IVb, phenyl ring "Z" is bonded to carbon "a."

In another general aspect, the present invention provides a Combretastatin analog of the following general Formula V:

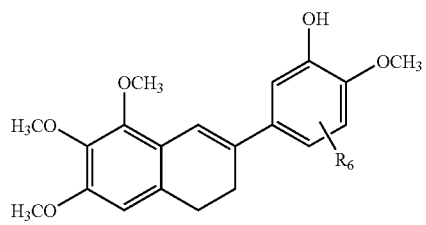

(V)

or a pharmaceutically acceptable salt thereof, wherein $R_6$ is selected from the group consisting of H, halogen, lower alkyl, lower alkoxy, hydroxyl, amine, phosphate, phosphoramidate, and amino acid acyl group.

In another embodiment of Formula V, $R_6$ is selected from the group consisting of H, $OCH_3$, phosphate and OH. In yet another embodiment of Formula V, $R_6$ is OH.

In another general aspect, the present invention provides a Combretastatin analog of the following general Formula VI:

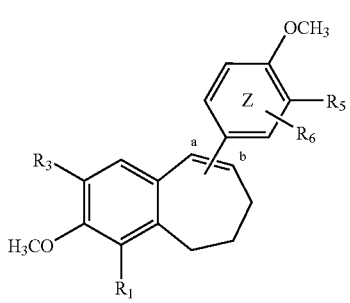

(VI)

or a pharmaceutically acceptable salt thereof, wherein:

$R_1$, $R_3$, $R_5$ and $R_6$ are each, independently, selected from the group consisting of H, halogen, lower alkyl, lower alkoxy, hydroxyl, amine, phosphate, phosphoramidate, and amino acid acyl group;

and phenyl ring "Z" is bonded to either carbon "a" or "b."

In one embodiment of Formula VI, $R_1$ and $R_3$ are selected from the group consisting of H, $OCH_3$, phosphate and OH. In another embodiment of Formula VI, $R_5$ and $R_6$, are each, independently, selected from the group consisting of H, $OCH_3$, phosphate and OH. In still another embodiment of Formula VI, the phenyl ring "Z" is bonded to carbon "a." In another embodiment of Formula VI, the phenyl ring "Z" is bonded to carbon "b."

In another general aspect, the present invention provides a Combretastatin analog of the following general Formula VII:

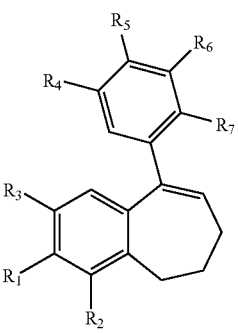

(VII)

or a pharmaceutically acceptable salt thereof, wherein $R_1$, $R_2$, $R_3$, $R_4$, $R_5$, $R_6$, and $R_7$ are each, independently, selected from the group consisting of OH, phosphate, and $OCH_3$.

In another general aspect, the present invention provides a Combretastatin analog of the following general formula VIII:

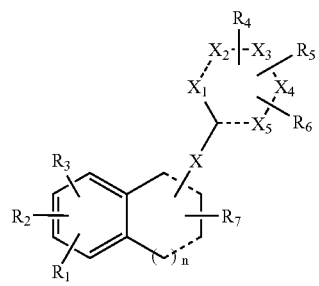

(VIII)

or a pharmaceutically acceptable salt thereof, wherein the dashed lines indicate a single or double bond; $R_1$, $R_2$, $R_3$, $R_4$, $R_5$, $R_6$ and $R_7$ are each, independently, selected from the group consisting of H, halogen, lower alkyl, lower alkoxy, hydroxyl, amine, phosphate, phosphoramidate, and amino acid acyl group; X is selected from the group consisting of a single bond, $CH_2$, O, S, N(H), and C(O); $X_1$, $X_2$, $X_3$, $X_4$ and $X_5$ are each, independently, selected from the group consisting of C, C(H), N, N(H), O and S, provided that at least one of $X_1$, $X_2$, $X_3$, $X_4$ and $X_5$ is not C or C(H); and n is 0, 1, 2 or 3.

In one embodiment of Formula VIII, $R_1$, $R_2$, $R_3$, $R_4$, $R_5$, $R_6$ and $R_7$ are each, independently, selected from the group consisting of H, lower alkoxy, hydroxyl, phosphate and phosphoramidate. In another embodiment of Formula VIII, X is a single bond. In another embodiment of Formula VIII, n is 0. In another embodiment of Formula VIII, n is 2. In another embodiment of Formula VIII, n is 3.

In another general aspect, the present invention provides a Combretastatin analog of the following general Formula IX:

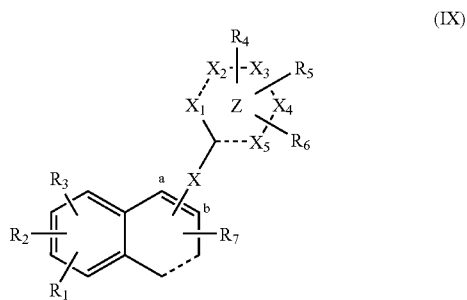

(IX)

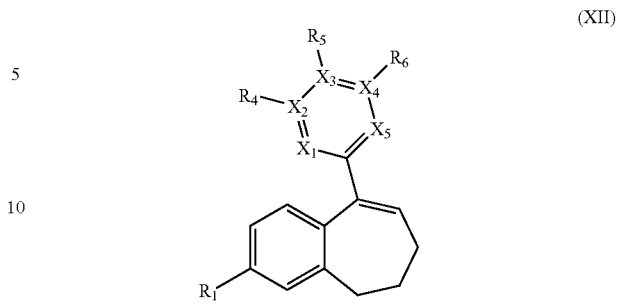

(XII)

or a pharmaceutically acceptable salt thereof, wherein the dashed line indicates a single or double bond; X is selected from the group consisting of a single bond, $CH_2$, O, S, N(H), and C(O); $X_1$, $X_2$, $X_3$, $X_4$ and $X_5$ are each, independently, selected from the group consisting of C, C(H), N, N(H), O and S, provided that at least one of $X_1$, $X_2$, $X_3$, $X_4$ and $X_5$ is not C or C(H); $R_1$, $R_2$, $R_3$, $R_4$, $R_5$, $R_6$ and $R_7$ are each, independently, selected from the group consisting of H, halogen, lower alkyl, lower alkoxy, hydroxyl, amine, phosphate, phosphoramidate, and amino acid acyl group, and ring "Z" is bonded to either carbon "a" or "b." In one embodiment of Formula IX, X is a single bond, and $R_1$, $R_2$ and $R_3$, are each, independently, selected from the group consisting of H, $OCH_3$, phosphate and OH. In another embodiment of Formula IX, X is a single bond, and $R_4$, $R_5$ and $R_6$, are each, independently, selected from the group consisting of H, $OCH_3$, phosphate and OH.

In another general aspect, the present invention provides a Combretastatin analog of the following general Formula X:

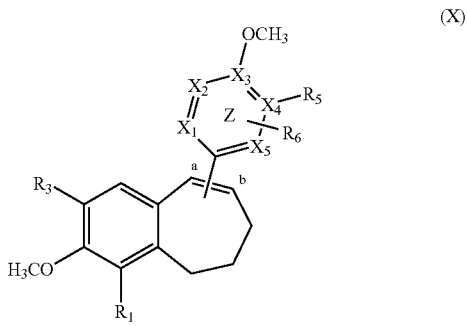

(X)

or a pharmaceutically acceptable salt thereof, wherein $R_1$, $R_3$, $R_5$ and $R_6$ are each, independently, selected from the group consisting of H, halogen, lower alkyl, lower alkoxy, hydroxyl, amine, phosphate, phosphoramidate, and amino acid acyl group, $X_1$, $X_2$, $X_3$, $X_4$ and $X_5$ are each, independently, selected from the group consisting of C, C(H) and N, provided that at least one of $X_1$, $X_2$, $X_3$, $X_4$ and $X_5$ is not C or C(H); and phenyl ring "Z" is bonded to either carbon "a" or "b." In one aspect of Formula X, $R_1$ and $R_3$ are selected from the group consisting of H, $OCH_3$, phosphate and OH. In another aspect of Formula X, $R_5$ and $R_6$, are each, independently, selected from the group consisting of H, $OCH_3$, phosphate and OH. In still another aspect of Formula X, the phenyl ring "Z" is bonded to carbon "a." In another aspect of Formula X, the phenyl ring "Z" is bonded to carbon "b."

In another general aspect, the present invention provides a Combretastatin analog of the following general Formula XII:

or a pharmaceutically acceptable salt thereof, wherein $R_1$, $R_4$, $R_5$ and $R_6$ are each, independently, selected from the group consisting of OH and $OCH_3$ and $X_1$, $X_2$, $X_3$, $X_4$ and $X_5$ are each, independently, selected from the group consisting of C, C(H) and N, provided that at least one of $X_1$, $X_2$, $X_3$, $X_4$ and $X_5$ is not C or C(H).

In another general aspect, the invention provides a method for treating a vascular proliferative disorder in an animal comprising administering to an animal an effective amount of a ring-substituted bicyclic fused ring system, wherein the centroid to centroid distance between the ring substituent and the outer ring of the bicyclic fused ring system is between 4 and 7 Å. In one embodiment, the centroid to centroid distance between the ring substituent and the outer ring of the bicyclic fused ring system is between 4 and 5 Å. In another embodiment, the centroid to centroid distance between the ring substituent and the outer ring of the bicyclic fused ring system is between 5 and 6 Å. In still another embodiment, the centroid to centroid distance between the ring substituent and the outer ring of the bicyclic fused ring system is between 6 and 7 Å. In another embodiment, the ring-substituted bicyclic fused ring system is represented by a compound of the Formula I, II, IIa, IIb, III, IV, IVa, IVb, V, VI, VII, VIII, IX, X and XII. In another embodiment, the ring-substituted bicyclic fused ring system is selected from the group consisting of 3-Methoxy-8-(3,4,5-trimethoxy-phenyl)-6,7-dihydro-5H-benzocycloheptene; 3-Methoxy-9-(3,4,5-trimethoxy-phenyl)-6,7-dihydro-5H-benzocycloheptene; 2-Methoxy-6-(3,4,5-trimethoxy-phenyl)-8,9-dihydro-7H-benzocyclohepten-1-ol; 2-Methoxy-5-(3,4,5-trimethoxy-phenyl)-8,9-dihydro-7H-benzocyclohepten-1-ol; 2-Methoxy-6-(3,4,5-trimethoxy-phenyl)-8,9-dihydro-7H-benzocyclohepten-1-ol; 2-Methoxy-6-(3,4,5-trimethoxy-phenyl)-7,8,9,10-tetrahydro-benzocycloocten-1-ol; 2-Methoxy-5-(3,4,5-trimethoxy-phenyl)-7,8,9,10-tetrahydro-benzocycloocten-1-ol; 3-Methoxy-6-(1,2,3-trimethoxy-8,9-dihydro-7H-benzocyclohepten-5-yl)-benzene-1,2-diol; 3-Methoxy-6-(1,2,3-trimethoxy-8,9-dihydro-7H-benzocyclohepten-5-yl)-benzene-1,2-diol; 2-Methoxy-5-(1,2,3-trimethoxy-8,9-dihydro-7H-benzocyclohepten-5-yl)-phenol; 3-Methoxy-6-(1,2,3-trimethoxy-7,8,9,10-tetrahydro-benzocycloocten-5-yl)-benzene-1,2-diol; 2-Methoxy-5-(1,2,3-trimethoxy-7,8,9,10-tetrahydro-benzocycloocten-5-yl)-phenol; 2-Methoxy-5-(1,2,3-trimethoxy-8,9-dihydro-7H-benzocyclohepten-6-yl)-phenol; 3-Methoxy-6-(1,2,3-trimethoxy-8,9-dihydro-7H-benzocyclohepten-6-yl)-benzene-1,2-diol; (1-Hydroxy-2-methoxy-8,9-dihydro-7H-benzocyclohepten-6-yl)-(3,4,5-trimethoxy-phenyl)-methanone; (1-Hydroxy-2-methoxy-8,9-dihydro-7H-benzocyclohepten-6-yl)-(3,4,5-trimethoxy-phenyl)-methanone; (1-Hydroxy-2-methoxy-7,8,9,10-tetrahydro-benzocycloocten-6-yl)-(3,4,5-trimethoxy-phenyl)-methanone; (1-Hydroxy-2-methoxy-7,8,9,10- tetrahydro-benzocyclooctcn-5-yl)-(3,4,5-trimethoxy-phenyl)-methanone; (2,3-Dihydroxy-4-methoxy-phenyl)-(1,2,3-trimethoxy-8,9-dihydro-7H-benzocyclohepten-5-yl)-methanone; (3-Hydroxy-4-methoxy-phenyl)-(1,2,3-trimethoxy-8,9-dihydro-7H-benzocyclohepten-5-yl)-methanone; (2,3-Dihydroxy-4-methoxy-phenyl)-(1,2,3-trimethoxy-7,8,9,10-tetrahydro-benzocycloocten-5-yl)-methanone and (3-Hydroxy-4-methoxy-phenyl)-(1,2,3-trimethoxy-7,8,9,10-tetrahydro-benzocycloocten-5-yl)-methanone.

In another aspect, the invention provides a method for selectively reducing the flow of blood to at least a portion of a neoplastic region, comprising administering a ring-substituted bicyclic fused ring system, wherein the centroid to centroid distance between the ring substituent and the outer ring of the bicyclic fused ring system is between 4 and 7 Å, thereby causing substantial necrosis of tissue in the neoplastic region without substantial necrosis of tissue in adjoining regions. In one embodiment, the centroid to centroid distance between the ring substituent and the outer ring of the bicyclic fused ring system is between 4 and 5 Å. In another embodiment, the centroid to centroid distance between the ring substituent and the outer ring of the bicyclic fused ring system is between 5 and 6 Å. In still another embodiment, the centroid to centroid distance between the ring substituent and the outer ring of the bicyclic fused ring system is between 6 and 7 Å. In another embodiment, the ring-substituted bicyclic fused ring system is represented by a compound of the Formula I, II, IIa, IIb, III, IV, IVa, IVb, V, VI, VII, VIII, IX, X and XII. In another embodiment, the ring-substituted bicyclic fused ring system is selected from the group consisting of 3-Methoxy-8-(3,4,5-trimethoxy-phenyl)-6,7-dihydro-5H-benzocycloheptene; 3-Methoxy-9-(3,4,5-trimethoxy-phenyl)-6,7-dihydro-5H-benzocycloheptene; 2-Methoxy-6-(3,4,5-trimethoxy-phenyl)-8,9-dihydro-7H-benzocyclohepten-1-ol; 2-Methoxy-5-(3,4,5-tri methoxy-phenyl)-8,9-dihydro-7H-benzocyclohepten-1-ol; 2-Methoxy-6-(3,4,5-trimethoxy-phenyl)-8,9-dihydro-7H-benzocyclohepten-1-ol; 2-Methoxy-6-(3,4,5-trimethoxy-phenyl)-7,8,9,10-tetrahydro-benzocycloocten-1-ol; 2-Methoxy-5-(3,4,5-trimethoxy-phenyl)-7,8,9,10-tetrahydro-benzocycloocten-1-ol; 3-Methoxy-6-(1,2,3-trimethoxy-8,9-dihydro-7H-benzocyclohepten-5-yl)-benzene-1,2-diol; 3-Methoxy-6-(1,2,3-trimethoxy-8,9-dihydro-7H-benzocyclohepten-5-yl)-benzene-1,2-diol; 2-Methoxy-5-(1,2,3-trimethoxy-8,9-dihydro-7H-benzocyclohepten-5-yl)-phenol; 3-Methoxy-6-(1,2,3-trimethoxy-7,8,9,10-tetrahydro-benzocycloocten-5-yl)-benzene-1,2-diol; 2-Methoxy-5-(1,2,3-trimethoxy-7,8,9,10-tetrahydro-benzocycloocten-5-yl)-phenol; 2-Methoxy-5-(1,2,3-trimethoxy-8,9-dihydro-7H-benzocyclohepten-6-yl)-phenol; 3-Methoxy-6-(1,2,3-trimethoxy-8,9-dihydro-7H-benzocyclohepten-6-yl)-benzene-1,2-diol; (1-Hydroxy-2-methoxy-8,9-dihydro-7H-benzocyclohepten-6-yl)-(3,4,5-trimethoxy-phenyl)-methanone; (1-Hydroxy-2-methoxy-8,9-dihydro-7H-benzocyclohepten-5-yl)-(3,4,5-trimethoxy-phenyl)-methanone; (1-Hydroxy-2-methoxy-7,8,9,10-tetrahydro-benzocycloocten-6-yl)-(3,4,5-trimethoxy-phenyl)-methanone; (1-Hydroxy-2-methoxy-7,8,9,10-tetrahydro-benzocycloocten-5-yl)-(3,4,5-trimethoxy-phenyl)-methanone; (2,3-Dihydroxy-4-methoxy-phenyl)-(1,2,3-trimethoxy-8,9-dihydro-7H-benzocyclohepten-5-yl)-methanone; (3-Hydroxy-4-methoxy-phenyl)-(1,2,3-trimethoxy-8,9-dihydro-7H-benzocyclohepten-5-yl)-methanone; (2,3-Dihydroxy-4-methoxy-phenyl)-(1,2,3-trimethoxy-7,8,9,10-tetrahydro-benzocycloocten-5-yl)-methanone and (3-Hydroxy-4-methoxy-phenyl)-(1,2,3-trimethoxy-7,8,9,10-tetrahydro-benzocycloocten-5-yl)-methanone.

In another embodiment, the ring-substituted bicyclic fused ring system is selected from the group consisting of 3-Methoxy-6-(4,5,6-trimethoxy-3H-inden-1-yl)-benzene-1,2-diol; 2-Methoxy-5-(4,5,6-trimethoxy-3H-inden-1-yl)-phenol; 2-Methoxy-5-(5,6,7-trimethoxy-3,4-dihydro-naphthalen-1-yl)-phenol; 2-Methoxy-5-(6,7,8-trimethoxy-3,4-dihydro-naphthalen-1-yl)-phenol; 2-Methoxy-5-(6,7,8-trimethoxy-3,4-dihydro-naphthalen-2-yl)-phenol; 3-Methoxy-6-(6,7,8-trimethoxy-3,4-dihydro-naphthalen-1-yl)-benzene-1,2-diol; 3-Methoxy-6-(6,7,8-trimethoxy-3,4-dihydro-naphthalen-2-yl)-benzene-1,2-diol; (2,3-Dihydroxy-4-methoxy-phenyl)-(4,5,6-trimethoxy-3H-inden-1-yl)-methanone; (3-Hydroxy-4-methoxy-phenyl)-(4,5,6-trimethoxy-3H-inden-1-yl)-methanone; (2,3-Dihydroxy-4-methoxy-phenyl)-(5,6,7-trimethoxy-3,4-dihydro-naphthalen-1-yl)-methanone and (3-Hydroxy-4-methoxy-phenyl)-(5,6,7-trimethoxy-3,4-dihydro-naphthalen-1-yl)-methanone.

In another embodiment, the reduction in tumor blood flow is reversible such that normal tumor blood flow is restored following cessation of treatment.

In another aspect, the invention provides a method for treating neoplastic disease in an animal comprising administering to an animal a ring-substituted bicyclic fused ring system, wherein the centroid to centroid distance between the ring substituent and the outer ring of the bicyclic fused ring system is between 4 and 7 Å. In one embodiment, the centroid to centroid distance between the ring substituent and the outer ring of the bicyclic fused ring system is between 4 and 5 Å. In another embodiment, the centroid to centroid distance between the ring substituent and the outer ring of the bicyclic fused ring system is between 5 and 6 Å. In still another embodiment, the centroid to centroid distance between the ring substituent and the outer ring of the bicyclic fused ring system is between 6 and 7 Å. In another embodiment, the ring-substituted bicyclic fused ring system is represented by a compound of the Formula I, II, IIa, IIb, III, IV, IVa, IVb, V, VI, VII, VIII, IX, X and XII. In another embodiment, the ring-substituted bicyclic fused ring system is selected from the group consisting of 3-Methoxy-8-(3,4,5-trimethoxy-phenyl)-6,7-dihydro-5H-benzocycloheptene; 3-Methoxy-9-(3,4,5-trimethoxy-phenyl)-6,7-dihydro-5H-benzocycloheptene; 2-Methoxy-6-(3,4,5-trimethoxy-phenyl)-8,9-dihydro-7H-benzocyclohepten-1-ol; 2-Methoxy-5-(3,4,5-trimethoxy-phenyl)-8,9-dihydro-7H-benzocyclohepten-1-ol; 2-Methoxy-6-(3,4,5-trimethoxy-phenyl)-8,9-dihydro-7H-benzocyclohepten-1-ol; 2-Methoxy-6-(3,4,5-trimethoxy-phenyl)-7,8,9,10-tetrahydro-benzocycloocten-1-ol; 2-Methoxy-5-(3,4,5-trimethoxy-phenyl)-7,8,9,10-tetrahydro-benzocycloocten-1-ol; 3-Methoxy-6-(1,2,3-trimethoxy-8,9-dihydro-7H-benzocyclohepten-5-yl)-benzene-1,2-diol; 3-Methoxy-6-(1,2,3-trimethoxy-8,9-dihydro-7H-benzocyclohepten-5-yl)-benzene-1,2-diol; 2-Methoxy-5-(1,2,3-trimethoxy-8,9-dihydro-7H-benzocyclohepten-5-yl)-phenol; 3-Methoxy-6-(1,2,3-trimethoxy-7,8,9,10-tetrahydro-benzocycloocten-5-yl)-benzene-1,2-diol; 2-Methoxy-5-(1,2,3-trimethoxy-7,8,9,10-tetrahydro-benzocycloocten-5-yl)-phenol; 2-Methoxy-5-(1,2,3-trimethoxy-8,9-dihydro-7H-benzocyclohepten-6-yl)-phenol; 3-Methoxy-6-(1,2,3-trimethoxy-8,9-dihydro-7H-benzocyclohepten-6-yl)-benzene-1,2-diol; (1-Hydroxy-2-methoxy-8,9-dihydro-7H-benzocyclohepten-6-yl)-(3,4,5-trimethoxy-phenyl)-methanone; (1-Hydroxy-2-methoxy-8,9-dihydro-7H-benzocyclohepten-5-yl)-(3,4,5-trimethoxy-phenyl)-methanone; (1-Hydroxy-2-methoxy-7,8,9,10-tetrahydrobenzocycloocten-6-yl)-(3,4,5-trimethoxy-phenyl)-methanone; (1-Hydroxy-2-methoxy-7,8,9,10-tetrahydro-benzocycloocten-5-yl)-(3,4,5-trimethoxy-phenyl)-methanone; (2,3-Dihydroxy-4-methoxy-phenyl)-(1,2,3-trimethoxy-8,9-dihydro-7H-benzocyclohepten-5-yl)-methanone; (3-Hydroxy-4-methoxy-phenyl)-(1,2,3-trimethoxy-8,9-dihydro-7H-benzocyclohepten-5-yl)-methanone; (2,3-Dihydroxy-4-methoxy-phenyl)-(1,2,3-trimethoxy-7,8,9,10-tetrahydro-benzocycloocten-5-yl)-methanone and (3-Hydroxy-4-methoxy-phenyl)-(1,2,3-trimethoxy-7,8,9,10-tetrahydro-benzocycloocten-5-yl)-methanone.

In another embodiment, the ring-substituted bicyclic fused ring system is selected from the group consisting of 3-Methoxy-6-(4,5,6-trimethoxy-3H-inden-1-yl)-benzene-1,2-diol; 2-Methoxy-5-(4,5,6-trimethoxy-3H-inden-1-yl)-phenol; 2-Methoxy-5-(5,6,7-trimethoxy-3,4-dihydro-naphthalen-1-yl)-phenol; 2-Methoxy-5-(6,7,8-trimethoxy-3,4-dihydro-naphthalen-1-yl)-phenol; 2-Methoxy-5-(6,7,8-trimethoxy-3,4-dihydro-naphthalen-2-yl)-phenol; 3-Methoxy-6-(6,7,8-trimethoxy-3,4-dihydro-naphthalen-1-yl)-benzene-1,2-diol; 3-Methoxy-6-(6,7,8-trimethoxy-3,4-dihydro-naphthalen-2-yl)-benzene-1,2-diol; (2,3-Dihydroxy-4-methoxy-phenyl)-(4,5,6-trimethoxy-3H-inden-1-yl)-methanone; (3-Hydroxy-4-methoxy-phenyl)-(4,5,6-trimethoxy-3H-inden-1-yl)-methanone; (2,3-Dihydroxy-4-methoxy-phenyl)-(5,6,7-trimethoxy-3,4-dihydro-naphthalen-1-yl)-methanone and (3-Hydroxy-4-methoxy-phenyl)-(5,6,7-trimethoxy-3,4-dihydro-naphthalen-1-yl)-methanone.

In another embodiment, the compound has the direct result of causing tumor cell cytotoxicity due to inhibition of mitosis.

In another aspect, the invention provides a method for inhibiting tubulin polymerization by contacting a tubulin-containing system with a ring-substituted bicyclic fused ring system, wherein the centroid to centroid distance between the ring substituent and the outer ring of the bicyclic fused ring system is between 4 and 7 Å. In one embodiment, the centroid to centroid distance between the ring substituent and the outer ring of the bicyclic fused ring system is between 4 and 5 Å. In another embodiment, the centroid to centroid distance between the ring substituent and the outer ring of the bicyclic fused ring system is between 5 and 6 Å. In still another embodiment, the centroid to centroid distance between the ring substituent and the outer ring of the bicyclic fused ring system is between 6 and 7 Å. In another embodiment, the ring-substituted bicyclic fused ring system is represented by a compound of the Formula I, II, IIa, IIb, III, IV, IVa, IVb, V, VI, VII, VIII, IX, X and XII. In another embodiment, the ring-substituted bicyclic fused ring system is selected from the group consisting of 3-Methoxy-8-(3,4,5-trimethoxy-phenyl)-6,7-dihydro-5H-benzocycloheptene; 3-Methoxy-9-(3,4,5-trimethoxy-phenyl)-6,7-dihydro-5H-benzocycloheptene; 2-Methoxy-6-(3,4,5-trimethoxy-phenyl)-8,9-dihydro-7H-benzocyclohepten-1-ol; 2-Methoxy-5-(3,4,5-trimethoxy-phenyl)-8,9-dihydro-7H-benzocyclohepten-1-ol; 2-Methoxy-6-(3,4,5-trimethoxy-phenyl)-8,9-dihydro-7H-benzocyclohepten-1-ol; 2-Methoxy-6-(3,4,5-trimethoxy-phenyl)-7,8,9,10-tetrahydro-benzocycloocten-1-ol; 2-Methoxy-5-(3,4,5-trimethoxy-phenyl)-7,8,9,10-tetrahydro-benzocycloocten-1-ol; 3-Methoxy-6-(1,2,3-trimethoxy-8,9-dihydro-7H-benzocyclohepten-5-yl)-benzene-1,2-diol; 3-Methoxy-6-(1,2,3-trimethoxy-8,9-dihydro-7H-benzocyclohepten-5-yl)-benzene-1,2-diol; 2-Methoxy-5-(1,2,3-trimethoxy-8,9-dihydro-7H-benzocyclohepten-5-yl)-phenol; 3-Methoxy-6-(1,2,3-trimethoxy-7,8,9,10-tetrahydro-benzocycloocten-5-yl)-benzene-1,2-diol; 2-Methoxy-5-(1,2,3-trimethoxy-7,8,9,10-tetrahydro-benzocycloocten-5-yl)-phenol; 2-Methoxy-5-(1,2,3-trimethoxy-8,9-dihydro-7H-benzocyclohepten-6-yl)-phenol; 3-Methoxy-6-(1,2,3-trimethoxy-8,9-dihydro-7H-benzocyclohepten-6-yl)-benzene-1,2-diol; (1-Hydroxy-2-methoxy-8,9-dihydro-7H-benzocyclohepten-6-yl)-(3,4,5-trimethoxy-phenyl)-methanone; (1-Hydroxy-2-methoxy-8,9-dihydro-7H-benzocyclohepten-5-yl)-(3,4,5-trimethoxy-phenyl)-methanone; (1-Hydroxy-2-methoxy-7,8,9,10-tetrahydro-benzocycloocten-6-yl)-(3,4,5-trimethoxy-phenyl)-methanone; (1-Hydroxy-2-methoxy-7,8,9,10-tetrahydro-benzocycloocten-5-yl)-(3,4,5-trimethoxy-phenyl)-methanone; (2,3-Dihydroxy-4-methoxy-phenyl)-(1,2,3-trimethoxy-8,9-dihydro-7H-benzocyclohepten-5-yl)-methanone; (3-Hydroxy-4-methoxy-phenyl)-(1,2,3-trimethoxy-8,9-dihydro-7H-benzocyclohepten-5-yl)-methanone; (2,3-Dihydroxy-4-methoxy-phenyl)-(1,2,3-trimethoxy-7,8,9,10-tetrahydro-benzocycloocten-5-yl)-methanone and (3-Hydroxy-4-methoxy-phenyl)-(1,2,3-trimethoxy-7,8,9,10-tetrahydro-benzocycloocten-5-yl)-methanone.

In another embodiment, the ring-substituted bicyclic fused ring system is selected from the group consisting of 3-Methoxy-6-(4,5,6-trimethoxy-3H-inden-1-yl)-benzene-1,2-diol; 2-Methoxy-5-(4,5,6-trimethoxy-3H-inden-1-yl)-phenol; 2-Methoxy-5-(5,6,7-trimethoxy-3,4-dihydro-naphthalen-1-yl)-phenol; 2-Methoxy-5-(6,7,8-trimethoxy-3,4-dihydro-naphthalen-1-yl)-phenol; 2-Methoxy-5-(6,7,8-trimethoxy-3,4-dihydro-naphthalen-2-yl)-phenol; 3-Methoxy-6-(6,7,8-trimethoxy-3,4-dihydro-naphthalen-1-yl)-benzene-1,2-diol; 3-Methoxy-6-(6,7,8-trimethoxy-3,4-dihydro-naphthalen-2-yl)-benzene-1,2-diol; (2,3-Dihydroxy-4-methoxy-phenyl)-(4,5,6-trimethoxy-3H-inden-1-yl)-methanone; (3-Hydroxy-4-methoxy-phenyl)-(4,5,6-trimethoxy-3H-inden-1-yl)-methanone; (2,3-Dihydroxy-4-methoxy-phenyl)-(5,6,7-trimethoxy-3,4-dihydro-naphthalen-1-yl)-methanone and (3-Hydroxy-4-methoxy-phenyl)-(5,6,7-trimethoxy-3,4-dihydro-naphthalen-1-yl)-methanone.

In another embodiment, the system is a tumor cell.

In another aspect, the invention provides a pharmaceutical formulation containing a compound of Formula I, II, IIa, IIb, III, IV, IVa, IVb, V, VI, VII, VIII, IX, X and XII in a pharmaceutically suitable carrier.

DETAILED DESCRIPTION OF THE INVENTION

Figure 1:
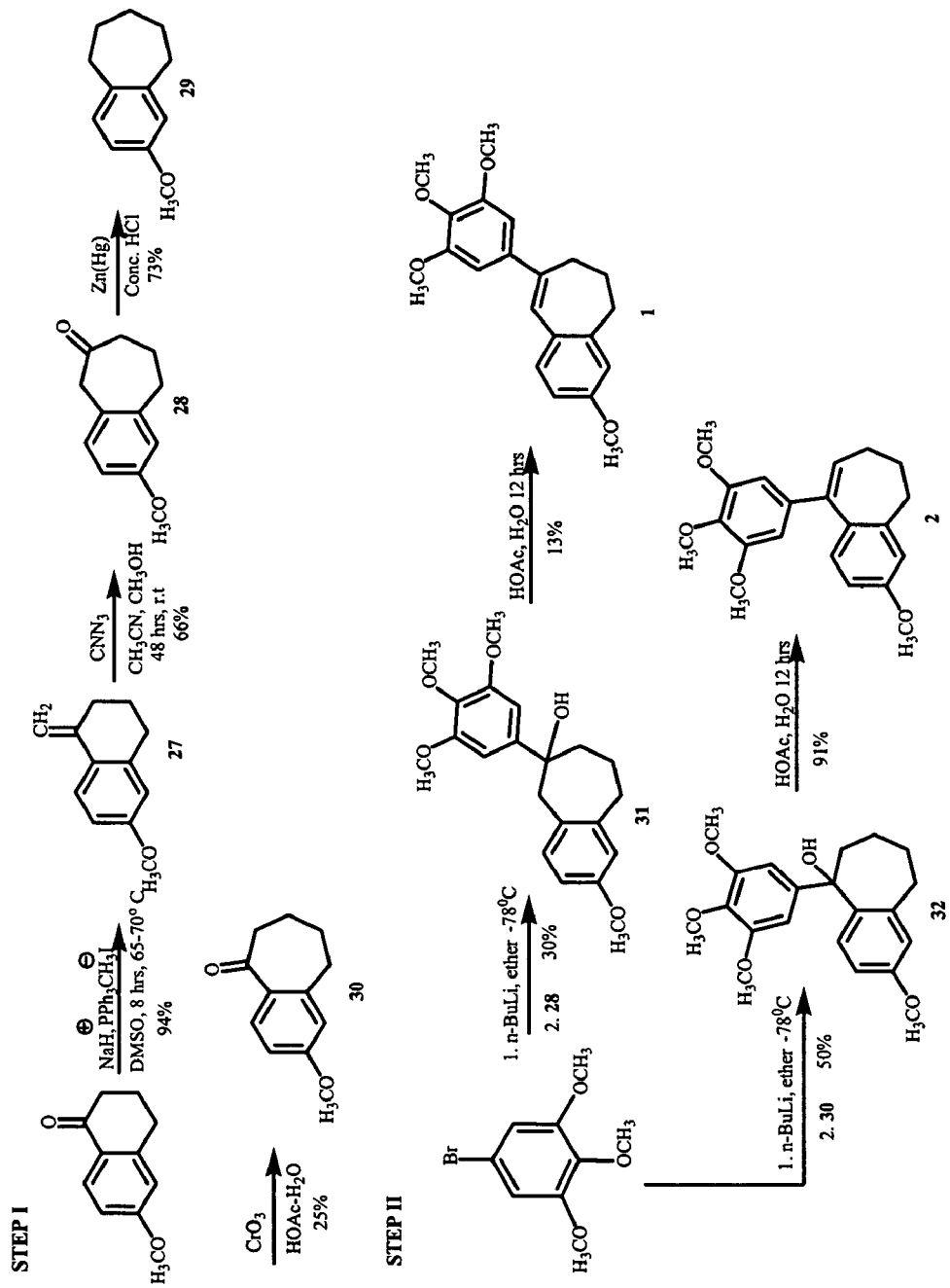
FIG. 1 depicts a route for the synthesis of Compounds 1 and 2, exemplary compounds of the invention.
Figure 2:
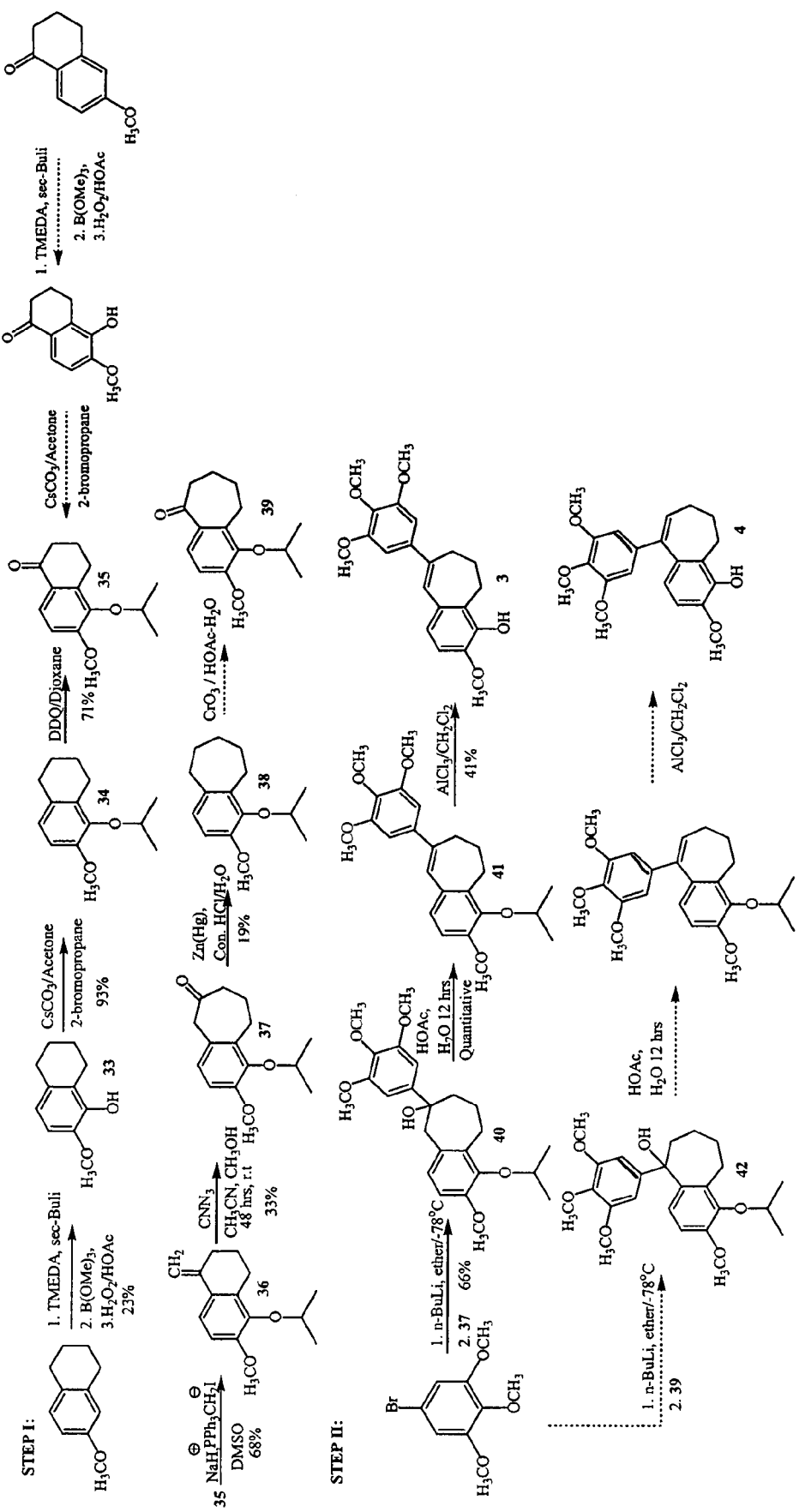
FIG. 2 depicts a route for the synthesis of Compounds 3 and 4, exemplary compounds of the invention.

The discovery of new anti-mitotic agents has resulted from the judicious combination of a molecular template (scaffold) that interacts with estrogen receptor (ER), and is modified with structural features deemed imperative for tubulin binding (i.e. hydroxyl, arylalkoxy groups, certain halogen substitutions, etc.). In particular, the methoxy aryl functionality seems important for increased interaction at the colchicine binding site in certain analogs (Shirai et al., *Biomedical Chem. Lett.* 1994). Our initial design and synthesis efforts centered on benzo[b]thiophene ligands containing structural motifs reminiscent of raloxifene, the selective estrogen receptor modulator (SERM) developed by Eli Lilly and Co. (Jones et al., *J. Med Chem.* 1984; Grese et al., *J. Med Chem.,* 1997; Palkowitz et al., *J. Med Chem.,* 1997), as well the colchicine and combretastatin tubulin binding agents.

The design premise that molecular skeletons of traditional estrogen receptor (ER) binding compounds can be modified with structural motifs reminiscent of colchicine and combretastatin A4 to produce especially inhibitors of tubulin polymerization has been validated by our preparation of very active benzo[b]thiophene, benzo[b]furan, and indole antitubulin and anti-mitotic agents (U.S. Pat. Nos. 5,886,025; 6,162,930; 6,350,777; and 6,593,374; PCT publication no. WO 01/19794; Mullica et al., *J. Chem. Cryst.,* 1998; Pinney, et al., *Bioorg. Med. Chem. Lett.,* 1999). The lead compounds in each series demonstrate remarkable biological activity against a variety of human cancer cell lines.

In further support of our hypothesis, recent studies have shown that certain estrogen receptor (ER) binding compounds (ex. 2-methoxyestradiol) can interact with tubulin and inhibit tubulin assembly as structurally modified estradiol congeners (D'Amato et al., *Proc. Natl. Acad Sci.,* 1994; Cushman et al., *J. Med Chem.,* 1995; Hamel et al., *Biochemistry,* 1996; Cushman et al., *J. Med. Chem.,* 1997). Estradiol is perhaps the most important estrogen in humans, and it is intriguing and instructive that the addition of the methoxy aryl motif to this compound makes it interactive with tubulin. It is also noteworthy that 2-methoxyestradiol is a natural mammalian metabolite of estradiol and may play a cell growth regulatory role especially prominent during pregnancy.

Our analysis of the structure-activity relationships of benzo[b]thiophene constructs has emphasized the importance of judicious placement of the trimethoxyphenyl ring and 4-methoxyphenyl rings. Without being bound by theory, pseudo pi stacking of the two aryl rings along with $sp^1$ hybridization at the bridge atoms between the rings is important for retaining tubulin binding properties. In addition to these factors, the centroid-to-centroid distances between the two-aryl rings are important. Optimization of this distance to approach that of CA4 (4.7 Å) improves the binding affinity of the molecule for the colchicine-binding site of tubulin. Introduction of spacer moiety of two contiguous atoms between the two rings improves tubulin binding properties by allowing the molecule more freedom to align itself for pseudo pi stacking. Similarly, restriction to free rotation by the introduction of a double bond resulted in better biological activity.

Surprisingly, the novel Combrestatin analogs described herein retain antiproliferative and tubulin binding properties despite the presence a 5, 6, 7, or 8-membered ring which confers increased flexibility to the molecule.

I) Definitions

As used herein, the following terms in quotations shall have the indicated meanings, whether in plural or singular form:

"Amino acid acyl group" in the amino acid acylamino group is an acyl group derived from the amino acid. The amino acids may be enumerated by a-amino acids, p-amino acids and y-amino acids. Examples of preferred amino acids include glycine, alanine, leucine, serine, lysine, glutamic acid, aspartic acid, threonine, valine, isoleucine, onithine, glutamine, asparagine, tyrosine, phenylalanine, cysteine, methionine, arginine, P-alanine, tryptophan, proline, histidine, etc. The preferred amino acid is serine and the preferred amino acid acyl group is a serinamide.

"Amine" refers to a free amine $NH_2$ or a lower alkylamino.

"Animal" refers to any warm-blooded mammal, preferably a human.

"Alkyl" refers to a group containing from 1 to 8 carbon atoms and may be straight chained or branched. An alkyl group is an optionally substituted straight, branched or cyclic saturated hydrocarbon group. When substituted, alkyl groups may be substituted with up to four substituent groups, R as defined, at any available point of attachment. When the alkyl group is said to be substituted with an alkyl group, this is used interchangeably with "branched alkyl group." Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include but are not limited to one or more of the following groups: halo (such as F, Cl, Br, I), haloalkyl (such as CCl3 or CF3), alkoxy, alkylthio, hydroxy, carboxy (—COOH), alkyloxycarbonyl (—C(O)R), alkylcarbonyloxy (—OCOR), amino (—NH2), carbamoyl (—NHCOOR— or —OCONHR—), urea (—NHCONHR—) or thiol (—SH). Alkyl groups as defined may also comprise one or more carbon to carbon double bonds or one or more carbon to carbon triple bonds.

The term "aryl" herein includes 5- and 6-membered single-ring aromatic groups that may include from zero to four heteroatoms, for example, benzene, pyrrole, furan, thiophene, imidazole, oxazole, thiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" include unsaturated aliphatic groups analogous in length and possible substitution to the alkyls described above, but that contain at least one double or triple bond respectively.

Unless the number of carbons is otherwise specified, "lower alkyl" means an alkyl group, as defined above, but having from one to ten carbons, more preferably from one to six carbon atoms (e.g., "$C_1$-$C_6$-alkyl") in its backbone structure. Likewise, "lower alkenyl," "lower alkoxy" and "lower alkynyl" have similar chain lengths. Preferred alkyl groups are lower alkyls. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl. Moreover, the term $C_{3-6}$-cycloalkyl includes, but is not limited to, cyclopropyl, cyclopentyl, and cyclohexyl. These alkyl groups, as well as cycloalkyl groups, may be further substituted.

The terms "heterocyclyl" or "heterocyclic group" include 3- to 10-membered ring structures, more preferably 4- to 7-membered rings, which ring structures include one to four heteroatoms. Heterocyclyl groups include pyrrolidine, oxolane, thiolane, piperidine, piperazine, morpholine, lactones, lactams such as azetidinones and pyrrolidinones, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, or an aromatic or heteroaromatic moiety.

"Aroyl" refers to the —(C=O)-aryl groups, wherein aryl is defined as hereinabove. The aryl group is bonded to the core compound through a carbonyl bridge.

"Cycloalkyl" is a species of alkyl containing from 3 to 15 carbon atoms, without alternating or resonating double bonds between carbon atoms. It may contain from 1 to 4 rings. Exemplary unsubstituted such groups include cyclopropyl, cyclobutyl, cyclopentyl, cyclohexyl, adamantyl, etc. Exemplary substituents include one or more of the following groups: halogen, alkyl, alkoxy, alkyl hydroxy, ammo, nitro, cyano, thiol and/or alkylthio.

"Halogen" or "Halo" refers to chlorine, bromine, fluorine or iodine.

"Lower alkoxy" refers to —O-alkyl groups, wherein alkyl is as defined hereinabove. The alkoxy group is bonded to the core compound through the oxygen bridge. The alkoxy group may be straight-chained or branched; although the straight-chain is preferred. Examples include methoxy, ethyloxy, propoxy, butyloxy, t-butyloxy, i-propoxy, and the like. Preferred alkoxy groups contain 1-4 carbon atoms, especially preferred alkoxy groups contain 1-3 carbon atoms. The most preferred alkoxy group is methoxy.

"Lower alkylamino" refers to a group wherein one or two alkyl groups is bonded to an amino nitrogen, i.e., NH(alkyl). The nitrogen is the bridge connecting the alkyl group to the core compound. Examples include NHMe, NHEt, NHPr, and the like.

The term "heteroatom" includes an atom of any element other than carbon or hydrogen. Preferred heteroatoms are nitrogen, oxygen, sulfur and phosphorus.

The term "aryl aldehyde," as used herein, includes compounds represented by the formula Ar—C(O)H, in which Ar is an aryl moiety (as described above) and —C(O)H is a formyl or aldehydo group "Prodrug" refers to a precursor form of the drug which is metabolically converted in vivo to produce the active drug. Preferred prodrugs of the present invention include the phosphate, phosphoramidate, or amino acid acyl groups as defined herein. The phosphate ester salt moiety may also include (—OP(O)(O-alkyl)$_2$ or (—OP(O)(O$^-$NH$_4^+$)$_2$). In preferred embodiments, a prodrug of the invention comprises a substitution of a phenolic moiety or amine moiety of the active drug with a phosphate, phosphoramidate, or amino acid acyl group. A wide variety of methods for the preparation of prodrugs are known to those skilled in the art (see, for example, Pettit and Lippert, *Anti-Cancer Drug Design*, (2000), 15, 203-216).

"Phenolic moiety" means herein a hydroxyl group when it refers to an R group on an aryl ring.

"Phosphate", "Phosphate moiety", or "Phosphate prodrug salt" refers to phosphate disalt moiety (—OP(O)(O$^-$M$^+$)$_2$), a phosphate triester moiety (—OP(O)(OR)$_2$) or a phosphate ester salt moiety (—OP(O)(OR)(O$^-$M$^+$), where M is a salt and R is chosen to be any appropriate alkyl or branched alkyl substituent (the two R groups may be the same alkyl group or may be mixed), or benzyl, or aryl groups. The salt M is advantageously Na, K and Li, but the invention is not limited in this respect.

Phosphoramidate" refers to a phosphoramidate ester salt moiety (—NP(O)(OR)(O-M+), a phosphoramidate diester moiety (—NP(O)(OR)2), or a phosphoramidate disalt moiety (—NP(O)(O-M+)2), where M is a salt and R is chosen to be any appropriate alkyl or branched alkyl substituent (the two R groups may be the same alkyl group or may be mixed), or benzyl, or aryl groups. The salt M is advantageously Na, K and Li, but the invention is not limited in this respect.

"Salt" is a pharmaceutically acceptable salt and can include acid addition salts such as the hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as Na, K, Li; alkali earth metal salts such as Mg or Ca; or organic amine salts such as those disclosed in PCT International Application Nos. WO02/22626 or WO00/48606, which are incorporated herein by reference in their entireties. Exemplary organic amine salts are tromethamine (TRIS) salts and amino acid salts (e.g. histidine salts) of the compounds of the invention.

"Treating" (or "treat") as used herein includes its generally accepted meaning which encompasses prohibiting, preventing, restraining, and slowing, stopping, or reversing progression, severity, of a resultant symptom. As such, the methods of this invention encompass both therapeutic and prophylactic administration.

"Tubulin Binding Agent" shall refer to a ligand of tubulin or a compound capable of binding to either Aβ-tubulin heterodimers or microtubules and interfering with the assembly or disassembly of microtubules.

"Effective amount" refers to the amount or dose of the compound, upon single or multiple dose administration to the patient, which provides the desired effect in the patient under diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

II) Compounds of the Invention

The compounds of the invention are Combretastatin analogs which are characterized by a bicyclic fused ring system substituted by a 6-membered ring. Such compounds are referred to herein as a "ring-substituted bicyclic fused ring systems" or "Combretastatin analogs." For demonstration purposes, an example of a ring-substituted bicyclic fused ring system is shown below:

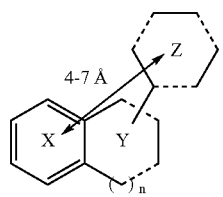

The X and Y rings constitute the bicyclic fused ring component, and the Z ring constitutes the 6-membered ring component. The dashed lines independently indicate a single or double line, and n can be 0, 1, 2 or 3. The carbons of the ring-substituted bicyclic fused ring system shown below can be individually substituted with an additional functional group, as is the case in Formula I, II, IIa, IIb, III, IV, IVa, IVb, V, VI, VII, VIII, IX, X and XII as demonstrated below. Examples of bicyclic fused ring systems include, but are not limited to, 1,2-dihydro-naphthalene, 1,2,3,4-tetrahydro-naphthalene, naphthalene, 6,7,8,9-tetrahydro-5H-benzocycloheptene, 6,7-dihydro-5H-benzocycloheptene, 7H-benzocycloheptene, 5,6,7,8,9,10-hexahydro-benzocyclooctene, 5H-benzocycloheptene, 5,6,7,8-tetrahydro-benzocyclooctene, and 5,6-dihydro-benzocyclooctene, and 5,8-dihydro-benzocyclooctene. Examples of 6-membered rings include, but are not limited to, cyclohexane, cyclohexene, cyclohexa-1,3-diene and benzene.

In a particular embodiment, the centroid to centroid distance between the ring substituent (ring Z) and the outer ring of the bicyclic fused ring system (ring X) is between 4 and 7 Å. In a preferred embodiment, the centroid to centroid distance between the ring substituent and the outer ring of the bicyclic fused ring system is between 4 and 5 Å. In another embodiment, the centroid to centroid distance between the ring substituent and the outer ring of the bicyclic fused ring system is between 5 and 6 Å. In still another embodiment, the centroid to centroid distance between the ring substituent and the outer ring of the bicyclic fused ring system is between 6 and 7 Å. As used herein, the term "centroid to centroid distance" refers to the distance between the center of geometries of the ring substituent of the ring-substituted bicyclic fused ring system and the outer ring of the ring-substituted bicyclic fused ring system. As used herein, the term "outer ring of the ring-substituted bicyclic fused ring system" refers to the ring of the ring-substituted bicyclic fused ring system that is not substituted by a 6-membered ring.

In one general aspect, the present invention provides a Combretastatin analog of the following general formula I:

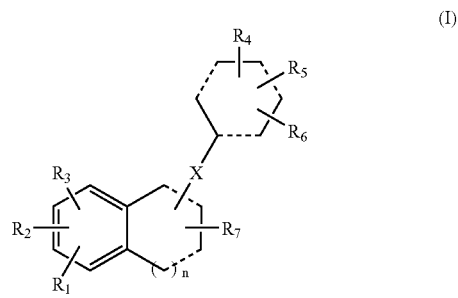

or a pharmaceutically acceptable salt thereof, wherein the dashed lines indicate a single or double bond; $R_1$, $R_2$, $R_3$, $R_4$, $R_5$, $R_6$ and $R_7$ are each, independently, selected from the group consisting of H, halogen, lower alkyl, lower alkoxy, hydroxyl, amine, phosphate, phosphoramidate, and amino acid acyl group; X is selected from the group consisting of a single bond, $CH_2$, O, S, N(H), and C(O); and n is 0, 1, 2 or 3. In one embodiment of Formula I, $R_1$, $R_2$, $R_3$, $R_4$, $R_5$, $R_6$ and $R_7$ are each, independently, selected from the group consisting of H, lower alkoxy, hydroxyl, phosphate and phosphoramidate. In another embodiment of Formula I, X is a single bond.

In another general aspect, the present invention provides a Combretastatin analog of the following general formula II:

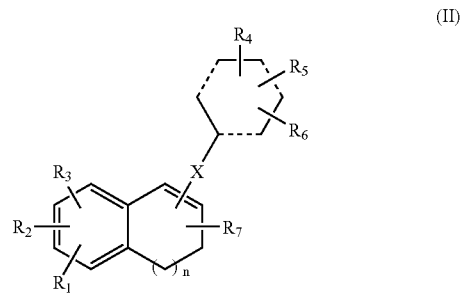

or a pharmaceutically acceptable salt thereof, wherein the dashed lines indicate a single or double bond; $R_1$, $R_2$, $R_3$, $R_4$, $R_5$, $R_6$ and $R_7$ are each, independently, selected from the group consisting of H, halogen, lower alkyl, lower alkoxy, hydroxyl, amine, phosphate, phosphoramidate, and amino acid acyl group; X is selected from the group consisting of a single bond, $CH_2$, O, S, N(H), and C(O); and n is 0, 1, 2 or 3. In another embodiment of Formula II, $R_1$, $R_2$, $R_3$, $R_4$, $R_5$, $R_6$ and $R_7$ are each, independently, selected from the group consisting of H, lower alkoxy, hydroxyl, phosphate and phosphoramidate. In yet another embodiment of Formula I, X is a single bond. In another embodiment of Formula II, $R_1$, $R_2$ and $R_3$, are each, independently, selected from the group consisting of H, $OCH_3$, phosphate and OH. In still another embodiment of Formula II, $R_4$, $R_5$ and $R_6$, are each, independently, selected from the group consisting of H, $OCH_3$, phosphate and OH. In still another embodiment of Formula II, $R_7$ is H.

In another general aspect, the present invention provides a Combretastatin analog of the following general formula IIa:

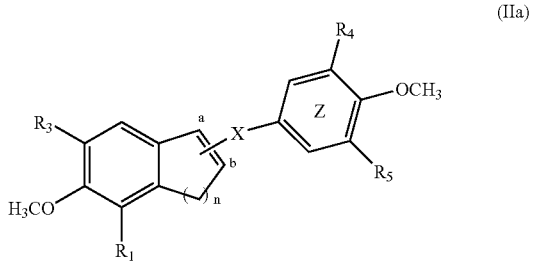

or a pharmaceutically acceptable salt thereof,
wherein the phenyl ring "Z" is bonded to either carbon "a" or "b";

$R_1$, $R_3$, $R_4$ and $R_5$ are each, independently, selected from the group consisting of H, lower alkoxy, phosphate, and hydroxyl;

X is selected from the group consisting of a single bond and C(O); and n is 1, 2, 3 or 4.

In one embodiment of formula IIa, $R_4$ and $R_5$ are $OCH_3$. In another embodiment of formula IIa, n is 1. In another embodiment of formula IIa, n is 3. In another embodiment of formula IIa, n is 4.

In another general aspect, the present invention provides a Combretastatin analog of the following general formula IIb:

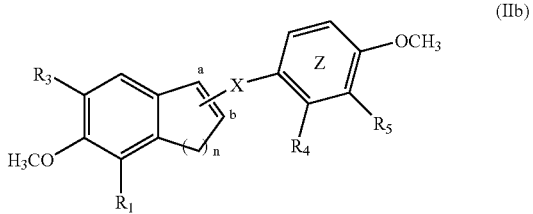

or a pharmaceutically acceptable salt thereof,
wherein the phenyl ring "Z" is bonded to either carbon "a" or "b";

$R_1$, $R_3$, $R_4$ and $R_5$ are each, independently, selected from the group consisting of H, lower alkoxy, phosphate, and hydroxyl;

X is selected from the group consisting of a single bond and C(O); and n is 1, 2, 3 or 4.

In one embodiment of formula IIb, $R_4$ is H or OH, and $R_5$ is OH. In another embodiment of formula IIb, $R_4$ is H or phosphate, and $R_5$ is phosphate. In another embodiment of formula IIb, n is 1. In another embodiment of formula IIb, n is 3. In another embodiment of formula IIb, n is 4.

In particular embodiments of formula IIa or IIb, $R_1$ and $R_3$ are H. In other embodiments of formula IIa or IIb, $R_1$ is OH and $R_3$ is H. In other embodiments of formula IIa or IIb, $R_1$ is phosphate and $R_3$ is H. In yet other embodiments of formula IIa or IIb, $R_1$ and $R_3$ are $OCH_3$.

In another general aspect, the present invention provides a Combretastatin analog of the following general Formula III:

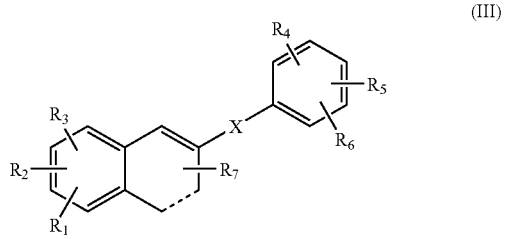

or a pharmaceutically acceptable salt thereof, wherein the dashed line indicates a single or double bond; X is selected from the group consisting of a single bond, $CH_2$, O, S, N(H), and C(O); and $R^1$, $R_2$, $R_3$, $R^4$, $R_5$, $R_6$ and $R_7$ are each, independently, selected from the group consisting of H, halogen, lower alkyl, lower alkoxy, hydroxyl, amine, phosphate, phosphoramidate, and amino acid acyl group. In one embodiment of Formula III, X is a single bond, and $R_1$, $R_2$ and $R_3$, are each, independently, selected from the group consisting of H, $OCH_3$, phosphate and OH. In another embodiment of Formula III, X is a single bond, and $R_4$, $R_5$ and $R_6$, are each, independently, selected from the group consisting of H, $OCH_3$, phosphate and OH.

In another general aspect, the present invention provides a Combretastatin analog of the following general Formula IV:

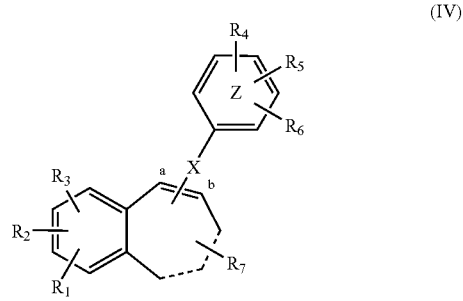

or a pharmaceutically acceptable salt thereof, wherein the dashed lines independently indicate a single or double bond; X is selected from the group consisting of a single bond, $CH_2$, O, S, N(H), and C(O); $R_1$, $R_2$, $R_3$, $R_4$, $R_5$, $R_6$ and $R_7$ are each, independently, selected from the group consisting of H, halogen, lower alkyl, lower alkoxy, hydroxyl, amine, phosphate, phosphoramidate, and amino acid acyl group; and phenyl ring "Z" is bonded to either carbon "a" or "b." In another embodiment of Formula IV, the dashed lines are single bonds, X is a single bond, and $R_1$, $R_2$ and $R_3$, are each, independently, selected from the group consisting of H, $OCH_3$, phosphate and OH. In still another embodiment of Formula IV, the dashed lines are single bonds, X is a single bond, and $R_4$, $R_5$ and $R_6$, are each, independently, selected from the group consisting of H, $OCH_3$, phosphate and OH. In still another embodiment of Formula IV, the dashed lines are single bonds, X is a single bond, and the phenyl ring "Z" is bonded to carbon "a." In yet another embodiment of Formula IV, the dashed lines are single bonds, X is a single bond, and phenyl ring "Z" is bonded to carbon "b."

In another general aspect, the present invention provides a Combretastatin analog of the following general formula IVa:

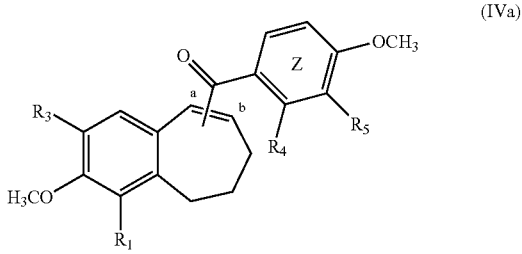

or a pharmaceutically acceptable salt thereof,
wherein the phenyl ring "Z" is bonded to either carbon "a" or "b"; and $R_1$, $R_3$, $R_4$ and $R_5$ are each, independently, selected from the group consisting of H, lower alkoxy, phosphate, and hydroxyl.

In one embodiment of formula IVa, $R_1$ and $R_3$ are $OCH_3$. In another embodiment of formula IVa, $R_4$ and $R_5$ are OH. In another embodiment of formula IVa, $R_4$ and $R_5$ are phosphate. In yet another embodiment of formula IVa, phenyl ring "Z" is bonded to carbon "a."

In another general aspect, the present invention provides a Combretastatin analog of the following general formula IVb:

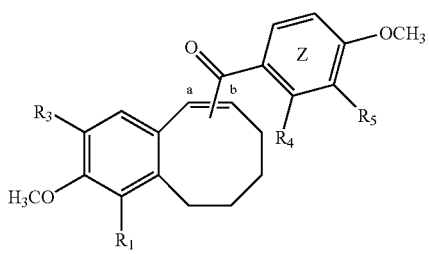

(IVb)

or a pharmaceutically acceptable salt thereof, wherein the phenyl ring "Z" is bonded to either carbon "a" or "b"; and $R_1$, $R_3$, $R_4$ and $R_5$ are each, independently, selected from the group consisting of H, lower alkoxy, phosphate, and hydroxyl.

In one embodiment of formula IVb, $R_1$ and $R_3$ are $OCH_3$. In another embodiment of formula IVb, $R_4$ and $R_5$ are OH. In another embodiment of formula IVb, $R_4$ and $R_5$ are phosphate. In yet another embodiment of formula IVb, phenyl ring "Z" is bonded to carbon "a."

In another general aspect, the present invention provides a Combretastatin analog of the following general Formula V:

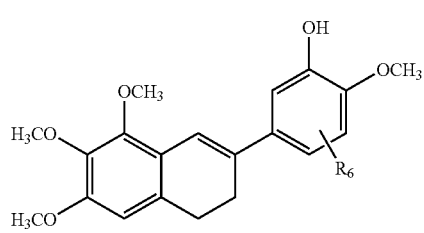

(V)

or a pharmaceutically acceptable salt thereof, wherein $R_6$ is selected from the group consisting of H, halogen, lower alkyl, lower alkoxy, hydroxyl, amine, phosphate, phosphoramidate, and amino acid acyl group. In another embodiment of Formula V, $R_6$ is selected from the group consisting of H, $OCH_3$, phosphate and OH. In yet another embodiment of Formula V, $R_6$ is OH.

In another general aspect, the present invention provides a Combretastatin analog of the following general Formula VI:

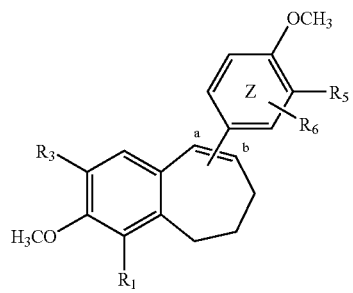

(VI)

or a pharmaceutically acceptable salt thereof, wherein $R_1$, $R_3$, $R_5$ and $R_6$ are each, independently, selected from the group consisting of H, halogen, lower alkyl, lower alkoxy, hydroxyl, amine, phosphate, phosphoramidate, and amino acid acyl group; and phenyl ring "Z" is bonded to either carbon "a" or "b." In one aspect of Formula VI, $R_1$ and $R_3$ are selected from the group consisting of H, $OCH_3$, phosphate and OH. In another aspect of Formula VI, $R_5$ and $R_6$, are each, independently, selected from the group consisting of H, $OCH_3$, phosphate and OH. In still another aspect of Formula VI, the phenyl ring "Z" is bonded to carbon "a." In another aspect of Formula VI, the phenyl ring "Z" is bonded to carbon "b."

In another general aspect, the present invention provides a Combretastatin analog of the following general Formula VII:

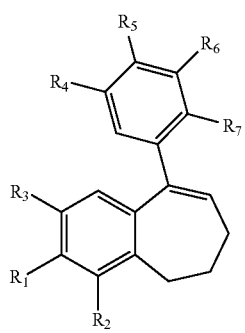

(VII)

or a pharmaceutically acceptable salt thereof, wherein $R_1$, $R_2$, $R_3$, $R_4$, $R_5$, $R_6$, and $R_7$ are each, independently, selected from the group consisting of OH, phosphate and $OCH_3$.

In another general aspect, the present invention provides a Combretastatin analog of the following general formula VIII:

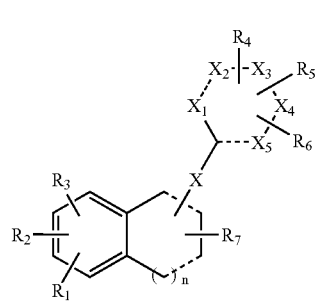

(VIII)

or a pharmaceutically acceptable salt thereof, wherein the dashed lines indicate a single or double bond; $R_1$, $R_2$, $R_3$, $R_4$, $R_5$, $R_6$ and $R_7$ are each, independently, selected from the group consisting of H, halogen, lower alkyl, lower alkoxy, hydroxyl, amine, phosphate, phosphoramidate, and amino acid acyl group; X is selected from the group consisting of a single bond, $CH_2$, O, S, N(H), and C(O); $X_1$, $X_2$, $X_3$, $X_4$ and $X_5$ are each, independently, selected from the group consisting of C, C(H), N, N(H), O and S, provided that at least one of $X_1$, $X_2$, $X_3$, $X_4$ and $X_5$ is not C or C(H); and n is 0, 1, 2 or 3. In one embodiment of Formula I, $R_1$, $R_2$, $R_3$, $R_4$, $R_5$, $R_6$ and $R_7$ are each, independently, selected from the group consisting of H, lower alkoxy, hydroxyl, phosphate and phosphoramidate. In another embodiment of Formula I, X is a single bond.

In another general aspect, the present invention provides a Combretastatin analog of the following general Formula IX:

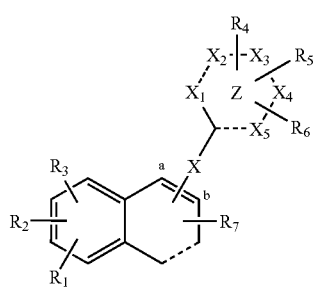

(IX)

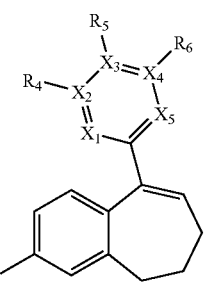

(XII)

or a pharmaceutically acceptable salt thereof, wherein the dashed line indicates a single or double bond; X is selected from the group consisting of a single bond, $CH_2$, O, S, N(H), and C(O); $X_1$, $X_2$, $X_3$, $X_4$ and $X_5$ are each, independently, selected from the group consisting of C, C(H), N, N(H), O and S, provided that at least one of $X_1$, $X_2$, $X_3$, $X_4$ and $X_5$ is not C or C(H); $R_1$, $R_2$, $R_3$, $R_4$, $R_5$, $R_6$ and $R_7$ are each, independently, selected from the group consisting of H, halogen, lower alkyl, lower alkoxy, hydroxyl, amine, phosphate, phosphoramidate, and amino acid acyl group, and ring "Z" is bonded to either carbon "a" or "b." In one embodiment of Formula III, X is a single bond, and $R_1$, $R_2$ and $R_3$, are each, independently, selected from the group consisting of H, $OCH_3$, phosphate and OH. In another embodiment of Formula III, X is a single bond, and $R_4$, $R_5$ and $R_6$, are each, independently, selected from the group consisting of H, $OCH_3$, phosphate and OH.

In another general aspect, the present invention provides a Combretastatin analog of the following general Formula X:

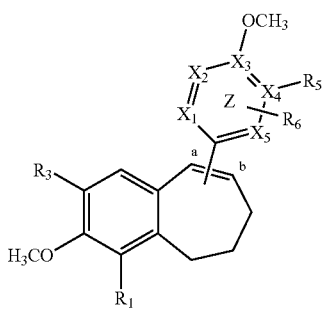

(X)

or a pharmaceutically acceptable salt thereof, wherein $R_1$, $R_3$, $R_5$ and $R_6$ are each, independently, selected from the group consisting of H, halogen, lower alkyl, lower alkoxy, hydroxyl, amine, phosphate, phosphoramidate, and amino acid acyl group; $X_1$, $X_2$, $X_3$, $X_4$ and $X_5$ are each, independently, selected from the group consisting of C, C(H) and N, provided that at least one of $X_1$, $X_2$, $X_3$, $X_4$ and $X_5$ is not C or C(H); and phenyl ring "Z" is bonded to either carbon "a" or "b." In one aspect of Formula VI, $R_1$ and $R_3$ are selected from the group consisting of H, $OCH_3$, phosphate and OH. In another aspect of Formula VI, $R_5$ and $R_6$, are each, independently, selected from the group consisting of H, $OCH_3$, phosphate and OH. In still another aspect of Formula VI, the phenyl ring "Z" is bonded to carbon "a." In another aspect of Formula VI, the phenyl ring "Z" is bonded to carbon "b."

In another general aspect, the present invention provides a Combretastatin analog of the following general Formula XI:

or a pharmaceutically acceptable salt thereof, wherein $R_1$, $R_4$, $R_5$ and $R_6$ are each, independently, selected from the group consisting of OH, phosphate, and $OCH_3$ and $X_1$, $X_2$, $X_3$, $X_4$ and $X_5$ are each, independently, selected from the group consisting of C, C(H) and N, provided that at least one of $X_1$, $X_2$, $X_3$, $X_4$ and $X_5$ is not C or C(H).

In another embodiment, the invention includes any novel compound or pharmaceutical compositions containing compounds of the invention described herein. For example, compounds and pharmaceutical compositions containing compounds set forth herein (e.g., Table I and Table II) are part of this invention, including prodrugs thereof and salts thereof, e.g., pharmaceutically acceptable salts. Like compounds of Formulas I, II, IIa, IIb, III, IV, IVa, IVb, V, VI, VII, VIII, IX, X and XII, the compounds of Table I and Table II are also considered to be "compounds of the invention."

Particular compounds of the invention also include the following compounds of Table I and Table II, each of which is considered a separate embodiment of the invention. The centroid to centroid distance is included in brackets after the name of the compound.

TABLE I

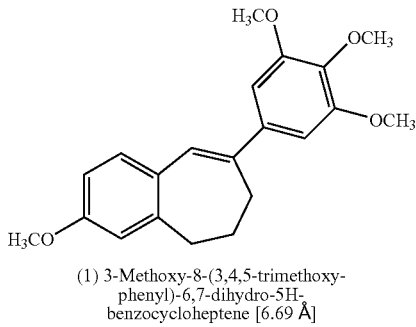

(1) 3-Methoxy-8-(3,4,5-trimethoxyphenyl)-6,7-dihydro-5H-benzocycloheptene [6.69 Å]

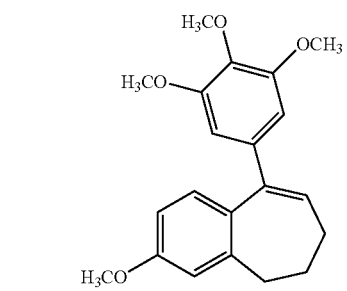

(2) 3-Methoxy-9-(3,4,5-trimethoxyphenyl)-6,7-dihydro-5H-benzocycloheptene [4.86 Å]

TABLE I-continued (3) 2-Methoxy-6-(3,4,5-trimethoxy-phenyl)-8,9-dihydro-7H-benzocyclohepten-1-ol [6.64 Å]

(4) 2-Methoxy-5-(3,4,5-trimethoxy-phenyl)-8,9-dihydro-7H-benzocyclohepten-1-ol [4.84 Å]

(5) 2-Methoxy-6-(3,4,5-trimethoxy-phenyl)-7,8,9,10-tetrahydro-benzocycloocten-1-ol [6.66 Å]

(6) 2-Methoxy-5-(3,4,5-trimethoxy-phenyl)-7,8,9,10-tetrahydro-benzocycloocten-1-ol [5.08 Å]

TABLE I-continued (7) 3-Methoxy-6-(4,5,6-trimethoxy-3H-inden-1-yl)-benzene-1,2-diol [5.28 Å]

(8) 2-Methoxy-5-(4,5,6-trimethoxy-3H-inden-1-yl)-phenol [5.29 Å]

(9) 3-Methoxy-6-(5,6,7-trimethoxy-3,4-dihydro-naphthalen-1-yl)-benzene-1,2-diol [5.06 Å]

(10) 2-Methoxy-5-(5,6,7-trimethoxy-3,4-dihydro-naphthalen-1-yl)-phenol [5.11 Å]

TABLE I-continued

(11) 3-Methoxy-6-(1,2,3-trimethoxy-8,9-dihydro-7H-benzocyclohepten-5-yl)-benzene-1,2-diol [5.10 Å]

(12) 2-Methoxy-5-(1,2,3-trimethoxy-8,9-dihydro-7H-benzocyclohepten-5-yl)-phenol [4.86 Å]

(13) 3-Methoxy-6-(1,2,3-trimethoxy-7,8,9,10-tetrahydro-benzocycloocten-5-yl)-benzene-1,2-diol [4.98 Å]

(14) 2-Methoxy-5-(1,2,3-trimethoxy-7,8,9,10-tetrahydro-benzocycloocten-5-yl)-phenol [5.02 Å]

TABLE I-continued

(27) 2-Methoxy-5-(6,7,8-trimethoxy-3,4-dihydro-naphthalen-1-yl)-phenol [6.67 Å]

(28) 2-Methoxy-5-(6,7,8-trimethoxy-3,4-dihydro-naphthalen-2-yl)-phenol [6.61 Å]

(29) 3-Methoxy-6-(6,7,8-trimethoxy-3,4-dihydro-naphthalen-1-yl)-benzene-1,2-diol [5.20 Å]

(30) 3-Methoxy-6-(6,7,8-trimethoxy-3,4-dihydro-naphthalen-2-yl)-benzene-1,2-diol [6.55 Å]

TABLE I-continued

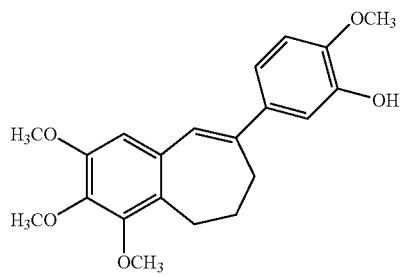

(31) 2-Methoxy-5-(1,2,3-trimethoxy-8,9-
dihydro-7H-benzocyclohepten-6-yl)-
phenol [6.67 Å]

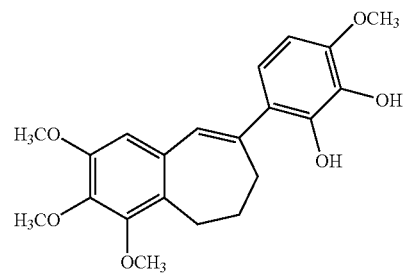

(32) 3-Methoxy-6-(1,2,3-trimethoxy-8,9-
dihydro-7H-benzocyclohepten-6-yl)-
benzene-1,2-diol [6.63 Å]

TABLE II

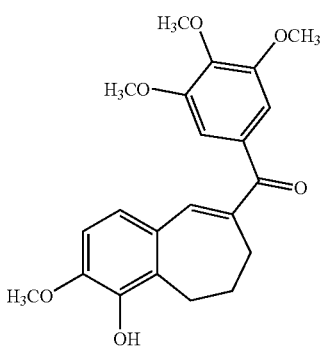

(15) (1-Hydroxy-2-methoxy-8,9-dihydro-
7H-benzocyclohepten-6-yl)-(3,4,5-
trimethoxy-phenyl)-methanone [6.71 Å]

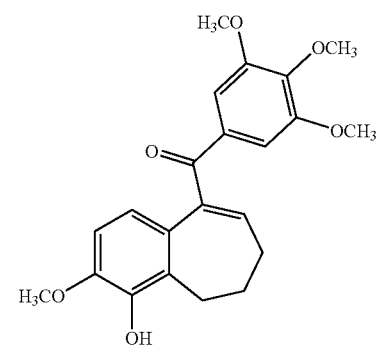

(16) (1-Hydroxy-2-methoxy-8,9-dihydro-
7H-benzocyclohepten-5-yl)-(3,4,5-
trimethoxy-phenyl)-methanone [6.64 Å]

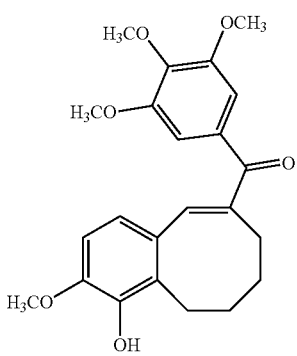

(17) (1-Hydroxy-2-methoxy-7,8,9,10-
tetrahydro-benzocycloocten-6-yl)-(3,4,5-
trimethoxy-phenyl)-methanone [6.76 Å]

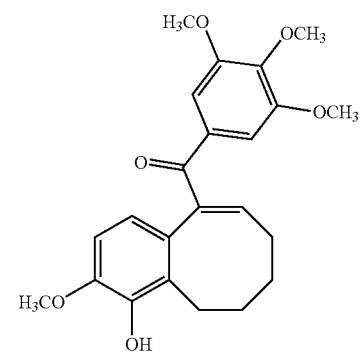

(18) (1-Hydroxy-2-methoxy-7,8,9,10-
tetrahydro-benzocycloocten-5-yl)-(3,4,5-
trimethoxy-phenyl)-methanone [10.01 Å]

TABLE II-continued

(19) (2,3-Dihydroxy-4-methoxy-phenyl)-(4,5,6-trimethoxy-3H-inden-1-yl)-methanone [5.28 Å]

(20) (3-Hydroxy-4-methoxy-phenyl)-(4,5,6-trimethoxy-3H-inden-1-yl)-methanone [5.15 Å]

(21) (2,3-Dihydroxy-4-methoxy-phenyl)-(5,6,7-trimethoxy-3,4-dihydro-naphthalen-1-yl)-methanone [5.18 Å]

(22) (3-Hydroxy-4-methoxy-phenyl)-(5,6,7-trimethoxy-3,4-dihydro-naphthalen-1-yl)-methanone [5.03 Å]

(23) (2,3-Dihydroxy-4-methoxy-phenyl)-(1,2,3-trimethoxy-8,9-dihydro-7H-benzocyclohepten-5-yl)-methanone [6.67 Å]

(24) (3-Hydroxy-4-methoxy-phenyl)-(1,2,3-trimethoxy-8,9-dihydro-7H-benzocyclohepten-5-yl)-methanone [6.67 Å]

(25) (2,3-Dihydroxy-4-methoxy-phenyl)-(1,2,3-trimethoxy-7,8,9,10-tetrahydro-benzocycloocten-5-yl)-methanone [6.69 Å]

(26) (3-Hydroxy-4-methoxy-phenyl)-(1,2,3-trimethoxy-7,8,9,10-tetrahydro-benzocycloocten-5-yl)-methanone [6.68 Å]

Compounds of the inventions can be synthesized according to standard organic synthesis procedures that are known in the art. Synthesis procedures for the compounds of the invention are also described in the Experimental section and Drawings included herewith.

Acid addition salts of the compounds of the invention are most suitably formed from pharmaceutically acceptable acids, and include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of the compounds of Formulas I, II, IIa, IIb, III, IV, IVa, IVb, V, VI, VII, VIII, IX, X and XII, and the compounds of the invention for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

In vivo hydrolyzable esters or amides of certain compounds of the invention can be formed by treating those compounds having a free hydroxy or amino functionality with the acid chloride of the desired ester in the presence of a base in an inert solvent such as methylene chloride or chloroform. Suitable bases include triethylamine or pyridine. Conversely, compounds of the invention having a free carboxy group may be esterified using standard conditions which may include activation followed by treatment with the desired alcohol in the presence of a suitable base.

III) Treatment of Cancer and Other Malignant Proliferative Disorders

The Combrestatin analogs of the present invention demonstrate remarkable cytotoxicity against a variety of human cancer cell lines. The ability of an agent to inhibit tubulin assembly and microtubule formation is an important property of many anticancer agents. Disruption of microtubules that comprise the cytoskeleton and mitotic spindle apparatus can interfere dramatically with the ability of a cell to successfully complete cell division.

The compounds of the present invention are highly cytotoxic to actively proliferating cells, inhibiting their mitotic division and often causing their selective apoptosis while leaving normal quiescent cells relatively unaffected. Accordingly, the antiproliferative or anti-mitotic properties of the compounds of the present invention can be used to directly inhibit the proliferation of, or impart direct cytotoxicity towards, the cells of malignant or neoplastic tumors or cancers including:

1) carcinomas, such as those of the bladder, breast, colon, rectum, kidney, liver, lung (including small cell lung cancer), pharynx, esophagus, gall bladder, urinary tract, ovaries, cervix, uterus, pancreas, stomach, endocrine glands (including thyroid, adrenal, and pituitary), prostate, testicles and skin, including squamous cell carcinoma;

2) hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

3) hematopoietic tumors of myeloid lineage, including acute and chronic myelogenous leukemias, myelodysplastic syndrome and promyelocytic leukemia;

4) tumors of mesenchymal origin, including fibrosarcoma and rhabdomyosarcoma;

5) tumors of the central and peripheral nervous system and meninges, including astrocytoma, neuroblastoma, glioma, schwannomas, retinoblastomas, neuroma, glioma, glioblastoma; and 6) other tumors, including melanoma, seminoma, teratocarcinoma, osteosarcoma, xenoderoma pigmentosum, keratoctanthoma, thyroid follicular cancer, anaplastic thyroid cancer and Kaposi's sarcoma.

Alternatively, the compounds of the present invention can impart indirect control of the growth and proliferation of the above tumors and cancers due to their effects on malignant proliferating vasculature, such as the endothelium, arteries, blood vessels, or neovasculature formed by a tumor. These antivascular properties include, but are not limited to, the selective destruction, damage, or occlusion, whether reversible or irreversible, partial or complete, of proliferating tumor vasculature.

The compounds of the present invention may also be useful for the treatment of the tumors and cancer described above when used either alone or in combination with radiotherapy and/or other chemotherapeutic treatments conventionally administered to patients for treating solid tumor cancers. For example, compounds of the present invention may be administered with chemotherapeutic agents selected from one of the following mechanistic classes:

1. Alkylating agents: compounds that donate an alkyl group to nucleotides. Alkylated DNA is unable to replicate itself and cell proliferation is stopped. Exemplary alkylating agents include Melphalan, Chlorambucil, cyclophosphamide, ifosfamide, busulfan, dacarbaine, methotrexate, 5-FU, cytosine arabinsoide, or 6-thioguanine.

2. Antianziozenic agents: compounds that inhibit the formation of tumor vasculature. Exemplary anti-angiogenic agents include TNP-470 or Avastin™.

3. Antitumor Antibiotics: compounds having antimicrobial and cytotoxic activity.
   Such compounds also may interfere with DNA by chemically inhibiting enzymes and mitosis or altering cellular membranes. Exemplary anti-tumor antibiotics include Actinomycin-D, bleomycin, mitomycin-C, Dactinomycin, Daunorubicin, and Doxorubicin.

4. Topoisomerase Inhibitors: agents which interfere with topoisomerase activity thereby inhibiting DNA replication. Such agents include CPT-11 and Topotecan.

5. Hormonal Therapy: includes, but is not limited to antiestrogens. An exemplary antiestrogen is Tamoxifen.

6. Antimicrotubule compounds. The compounds of the invention may be used in combination with other anti-microtubule compounds, including for example, Combretastatin A-1 Diphosphate, Combretastatin A-4 Phosphate, Vincristine, paclitaxel, taxotere, etoposide, and vinblastine.

In yet other embodiments, the compounds of the present invention may be administered with a platinum coordination compounds (e.g carboplatin, cisplatin, or oxaliplatin).

IV) Treatment of Nonmalignant Vascular Proliferative Disorders

In other embodiments, the compounds of the invention as well as analogs thereof, may be employed as vascular targeting agents (VTAs), and thus are also useful for the treatment of non-malignant vascular proliferative disorders, where the endothelium, artery, blood vessel, or neovasculature is not associated with a tumor but is nonetheless formed by undesirable or pathological angiogenesis. Such disease states include, without limitation:
1) ocular diseases such as wet or age-related macular degeneration, myopic macular degeneration, diabetic retinopathy, retinopathy of prematurity, diabetic macular edema, uveitis, neovascular glaucoma, rubeosis, retrolental fibroplasias, angioid streaks, ocular histoplasmosis, and corneal neovascularization;
2) inflammatory disorders such as endometriosis, psoriasis, rheumatoid arthritis, Osler-Webber Syndrome, wound granulation, and
3) cardiovascular diseases such as atherosclerosis, atheroma, restenosis, haemangioma, restenosis.

In one preferred embodiment, the present invention is directed to the administration of compound of the invention for the treatment of non-malignant vascular proliferative disorders in the retinal tissue of the eye. Neovascularization of retinal tissue or "retinopathy" is a pathogenic condition characterized by vascular proliferation and occurs in a variety of ocular diseases with varying degrees of vision failure. The blood-retinal barrier (BRB) is composed of specialized non-fenestrated tightly-joined endothelial cells that form a transport barrier for certain substances between the retinal capillaries and the retinal tissue. The nascent vessels of the retina associated with the retinopathies are aberrant, much like the vessels associated with solid tumors. Tubulin binding agents, inhibitors of tubulin assembly, and vascular targeting agents may be able to attack the aberrant vessels because these vessels do not share architectural similarities with the BRB. Tubulin binding agents may halt the progression of the disease much like they do with a tumor-vasculature. The administration of a VTA for the pharmacological control of the retinal neovascularization associated with retinopathies as wet macular degeneration, proliferative diabetic retinopathy or retinopathy of prematurity, would potentially benefit patients for which few therapeutic options are available.

The compounds of the present invention are also contemplated for use in the treatment of vascular disease, particularly atherosclerosis and restenosis. Atherosclerosis is the most common form of vascular disease and leads to insufficient blood supply to critical body organs, resulting in heart attack, stroke, and kidney failure. Additionally, atherosclerosis causes major complications in those suffering from hypertension and diabetes, as well as tobacco smokers. Atherosclerosis is a form of chronic vascular injury in which some of the normal vascular smooth muscle cells (VSMC) in the artery wall, which ordinarily control vascular tone, regulate blood flow, change their nature and develop "cancer-like" behavior. These VSMC become abnormally proliferative, secreting substances (growth factors, tissue-degradation enzymes and other proteins) which enable them to invade and spread into the inner vessel lining, blocking blood flow and making that vessel abnormally susceptible to being completely blocked by local blood clotting, resulting in the death of the tissue served by that artery.

Restenosis, the recurrence of stenosis or artery stricture after corrective surgery, is an accelerated form of atherosclerosis. Recent evidence has supported a unifying hypothesis of vascular injury in which coronary artery restenosis along with coronary vein graft and cardiac allograft atherosclerosis can be considered to represent a much-accelerated form of the same pathogenic process that results in spontaneous atherosclerosis. Restenosis is due to a complex series of fibroproliferative responses to vascular injury involving potent growth-regulatory molecules, including platelet-derived growth factor (PDGF) and basic fibroblast growth factor (bFGF), also common to the later stages in atherosclerotic lesions, resulting in vascular smooth muscle cell proliferation, migration and neointimal accumulation.

Restenosis occurs after coronary artery bypass surgery (CAB), endarterectomy, and heart transplantation, and particularly after heart balloon angioplasty, atherectomy, laser ablation or endovascular stenting (in each of which one-third of patients redevelop restenosis within 6 months), and is responsible for recurrence of symptoms (or death), often requiring repeat revascularization surgery. Despite over a decade of research and significant improvements in the primary success rate of the various medical and surgical treatments of atherosclerotic disease, including angioplasty, bypass grafting and endarterectomy, secondary failure due to late restenosis continues to occur in 30-50% of patients. Repeated revascularization surgery consumes time and money, is inconvenient to the patient, and can carry a significant risk of complications or death. The most effective way to prevent restenosis is at the cellular level.

V) Dosage and Administration of Compounds

A typical daily dose will contain from about 0.1 mg/kg to about 1000 mg/kg of the active compound of this invention. Preferably, daily doses will be about 10 mg/kg to about 100 mg/kg, and most preferably about 10 mg.

In effecting treatment of a patient afflicted with a condition, disease or disorder described herein, a compound of the present invention can be administered systemically in any form or mode which makes the compound bioavailable in effective amounts. Systemic administration may be accomplished by administration of a compound of the present invention into the bloodstream at a site which is separated by a measurable distance from the diseased or affected organ or tissue. For example, compounds of the present invention can be administered orally, parenterally, subcutaneously, intramuscularly, intravenously, transdermally, intranasally, rectally, buccally, and the like. Oral or intravenous administration is generally preferred for treating neoplastic disease or cancer. Alternatively, the compound may be administered non-systemically by local administration of the compound of the present invention directly at the diseased or affected organ or tissue. Treatment of ocular diseases characterized by the presence of non-malignant proliferative vasculature or neovascularization, can be achieved using non-systemic administration methods such as intravitreal injection, sub-Tenon's injection, ophthalmic drops, iontophoresis, topical formulation and implants and/or inserts. One skilled in the art of preparing formulations can readily select the proper form and mode of administration depending upon the particular characteristics of the compound selected, the disease state to be treated, the stage of the disease, and other relevant circumstances.

It will be understood by the skilled reader that all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are included in the names of them.

According to another aspect, the present invention provides a pharmaceutical composition, which comprises a compound of the present invention or a pharmaceutically acceptable salt thereof as defined hereinabove and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well know in the art.

The compositions are preferably formulated in a unit dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient.

The following formulation examples are illustrative only and are not intended to limit the scope of the invention in any way.

The compositions of the present invention may be formulated in a conventional manner using one or more pharmaceutically acceptable carriers. Thus, the active compounds of the invention may be formulated for oral, buccal, transdermal (e.g., patch), intranasal, parenteral (e.g., intravenous, intramuscular or subcutaneous) or rectal administration or in a form suitable for administration by inhalation or insufflation.

Alternatively, compounds of the present invention can be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The compositions in liposome form can contain, in addition to a compound of the present invention, stabilizers, preservatives, excipients, and the like. The preferred lipids are the phospholipids and the phosphatidylcholines (lecithins), both natural and synthetic. Methods to form liposomes are well known in the art (see for example, Prescott Ed., Methods in Cell Biology, Volume XTV, Academic Press, New York, N.Y., 1976, p 33).

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose of calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically A acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in a powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

Tablets or capsules of the compounds may be administered singly or two or more at a time as appropriate. It is also possible to administer the compounds in sustained release formulations.

The physician will determine the actual dosage which will be most suitable for an individual patient and it will vary with the age, weight and response of the particular patient. The above dosages are exemplary of the average case. There can of course, be individual instances where higher or lower dosage ranges are merited, and such are within the scope of this invention.

The compounds of the present invention can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

"Administering" means any of the standard methods of administering a compound to a subject, known to those skilled in the art. Examples include, but are not limited to intravenous, intramuscular or intraperitoneal administration.

For the purposes of this invention "pharmaceutically acceptable carriers" means any of the standard pharmaceutical carriers. Examples of suitable carriers are well known in the art and may include, but are not limited to, any of the standard pharmaceutical carriers such as a phosphate buffered saline solutions, phosphate buffered saline containing POLYSORB 80, water, emulsions such as oil/water emulsion, and various types of wetting agents. Other carriers may also include sterile solutions, tablets, coated tablets, and capsules.

Typically such carriers contain excipients such as starch, milk, sugar, certain types of clay, gelatin, stearic acid or salts thereof, magnesium or calcium stearate, talc, vegetable fats or oils, gums glycols, or other known excipients. Such carriers may also include flavor and color additives or other ingredients. Compositions comprising such carriers are formulated by well known convention methods.

Methods of determining an "effective amount" are well known to those skilled in the art and depend upon factors including, but not limited to, the size of the patient and the carrier used.

The invention is further defined by reference to the following examples and preparations which describe the manner and process of making and using the invention and are illustrative rather than limiting. It will be apparent to those skilled in the art that many modifications, both to the materials and methods, may be practiced without departing from the purpose and interest of the invention.

EXAMPLES

Materials and Methods

Chemicals were commercially obtained from the Aldrich Chemical Company, Fisher Scientific and ACROS Chemicals and used directly as purchased. Solvents such as acetone, diethylether and ethylacetate were used as purchased, and other solvents were purified by standard procedures. Tetrahydrofuran (THF) was dried over potassium metal and benzophenone and distilled freshly prior to use; methylene chloride ($CH_2Cl_2$) was dried using calcium hydride and distilled prior to use. Triethyl amine was distilled over calcium hydride and stored in a sealed bottle.

Reactions were followed by thin layer chromatography (TLC) and/or gas chromatography. Purification of products was carried out using flash column chromatography with silica gel. Silica gel plates for thin layer chromatography and silica gel (260-400 mesh) for column chromatography were obtained from Merck EM Science.

$^1H$ and $^{13}C$ NMR spectra were recorded in deuterated chloroform or deuterated methyl sulfoxide or deuterium oxide using an AMX 360 MHz (90 MHz for $^{13}C$, and 145 MHz for $^{31}P$) or a DPX Avance 300 MHz (75 MHz for $^{13}C$, and 120 MHz for $^{31}P$) Brüker NMR spectrometer. Peaks are listed as singlet (s), doublet (d), doublet of doublet (dd), triplet (t), or multiplet (m) with the coupling constant (J) expressed in Hz. High-resolution mass spectra were obtained using a VG/Fisons GC/NASS High Resolution Mass Spectrometer. Elemental analyses were obtained from Atlantic Microlab Inc., Norcross, Ga. Melting points were determined using a Thomas-Hoover melting point apparatus and are uncorrected.

In many of the reactions, particularly those using Pd, methanol may be substituted for ethanol, and vice versa. Additionally, $AlCl_3$ may be substituted for $TiCl_4$, and vice versa.

Example 1

Synthesis of Representative Combretastatin Analogs

Synthesis of 3-Methoxy-9-(3,4,5-trimethoxy-phenyl)-6,7-dihydro-5H-benzocycloheptene
(2; see FIG. 1)

6-Methoxy-1-methylene-1,2,3,4-tetrahydronaphthalene (27)

To a dry 500 mL 3-necked round bottom flask equipped with a reflux condenser and magnetic stir bar, was charged sodium hydride (3.0 g, 172.89 mmol). The reaction flask was put under nitrogen, and 35 mL of anhydrous DMSO was added. The reaction mixture was heated to 70-75° C., and stirred at that temperature until the evolution of hydrogen ceased. The reaction mixture was cooled to room temperature and additional 25 mL of DMSO was added. Methyltriphenylphosphonium iodide (46.57 g, 115.26 mmol) was added in portions over a period of 1 h. 25 mL of additional DMSO was added to facilitate easy stirring. After the completion of addition, the reaction mixture was stirred for 20 minutes. 6-methoxytetralone (10.156 g, 57.63 mmol) dissolved in 10 mL of anhydrous DMSO was added to reaction mixture. Then, the reaction mixture was heated to 60-65° C., and stirred at that temperature for 8 h. The reaction mixture was poured into a 500 mL Erlenmeyer flask containing 150 mL of crushed ice and 150 mL of hexanes. The resulting mixture was stirred vigorously for 15 min, and then extracted with hexanes. The combined organic layers were washed DMSO: Water (1:1) and then dried over anhydrous sodium sulfate, filtered and evaporated under reduced pressure. Purification by flash column chromatography (silica gel 3:97 EtOAc: Hexanes) yielded 9.42 g of 27 as white solid (94%). Rf: 0.71, (30:70, EtOAc:Hexanes).

$^1H$ NMR ($CDCl_3$, 300 MHz): δ 7.8 (d, J=8.73 Hz, 1H), δ 6.74 (dd, J=8.72 Hz, 2.74 Hz, 1 H), δ 6.62 (d, J=2.71 Hz, 1 H), δ 5.34 (s, 1H), δ 4.84 (s, 1 H), δ3.76 (s, 3H), δ 2.81 (t, J=6.27 Hz, 2 H), δ 2.53 (t, J=6.34, 2H), δ 1.87 (p, J=6.16, 2 H).

2-Methoxy-5,7,8,9-tetrahydro-benzocyclohepten-6-one (28)

2-Methoxy-5,7,8,9-tetrahydro-benzocyclohepten-6-one (28) was prepared according to the methods of Miller et al. (Miller et al. *J. Org. Chem.* 1978, 43 (8), 1569) and as outlined below.

Preparation of cyanogen azide: Finely powdered cyanogen azide (8.58 g, 132 mmol) was added rapidly to a 0° C. solution of cyanogen bromide (13.98 g, 132 mmol) in 40 mL of anhydrous acetonitrile. The reaction mixture was stirred for 4 h at 0° C. and clear supernatant solution containing cyanogen azide (7.18 g, 105.61 mmol) was filtered and used for the ring expansion reaction.

Ring expansion reaction: The exocyclic olefin 27 (4.6 g, 26.40 mmol) was charged in a 250 mL round bottom flask under nitrogen. 40 mL of anhydrous methanol:acetonitrile (1:1) was added to the reaction flask, and the reaction mixture was stirred at room temperature. To this was added freshly prepared cyanogen azide (7.18 g, 105.61 mmol) and the reaction mixture was stirred at room temperature for 48 h. 25 mL of 6 M of HCl was added and the reaction was stirred at 50° C. for 4 h. The reaction mixture was then cooled to room temperature and extracted with ether (2×200 mL). The ethereal extracts were washed with water until neutral and then dried over anhydrous sodium sulfate. The organic phase was then percolated through a column of basic alumina capped with a layer of celite to remove the explosive azides. Evaporation of the solvent followed by purification by flash column chromatography (8:92 EtOAc:Hexanes) yielded 3.33 g of 28 (off-white solid on refrigeration). Rf. 0.38 (30:70, EtOAc:Hexanes).

$^1$H NMR (CDCl$_3$, 300 MHz): δ 7.06 (d, J=7.72 Hz, 1H), δ 6.70 (m, 2 H), δ 3.79 (s, 3 H), δ 3.65 (s, 2 H), δ 2.90 (m, 2H), δ 2.55 (t, J=6.8, 2 H), δ1.98 (m, 2H).

2-Methoxy-6,7,8,9-tetrahydro-5H-benzo-cycloheptane (29)

Amalgamated zinc was prepared by shaking 4 g of Zn powder and 400 mg of mercuric chloride, 4 mL of water and 0.25 mL of con. HCl in a 100 mL round bottom flask for 10 min. The supernatant liquid was decanted and 28 (215 mg, 1.13 mmol) was added, followed by 15 mL of con. HCl. The reaction mixture was then refluxed for 3 hours. The reaction mixture was cooled and extracted with ether (20 mL×3) and the combined ethereal extracts were washed with water until neutral, then dried over anhydrous magnesium sulfate, filtered and evaporated under reduced pressure. The compound was purified by flash column chromatography on neutral alumina. Product, 29 was obtained in just hexanes (140 mg, 74%). Rf value: 0.535 (10:90, EtOAc:Hexanes).

$^1$H NMR (CDCl$_3$, 300 MHz): δ 6.99 (d, J=8.12 Hz, 1H), δ 6.67 (d, J=2.68 Hz, 1 H), δ 6.62 (dd, J=8.12 Hz, 2.74 Hz, 1 H), δ 3.76 (s, 3 H), δ 2.73 (m, 2 H), δ 1.79 (m, 2H), δ 1.62 (m, 4 H).

2-Methoxy-6,7,8,9-tetrahydro-benzocyclo-hepten-5-one (30)

29 (3.42 g, 19.4 mmol) was taken in a 500 mL round bottom flask, and to this was added 40 mL of glacial acetic acid followed by a CrO$_3$ (5.82 g, 58.21 mmol) dissolved in 5 mL of water and 20 mL of acetic acid dropwise. After the addition was completed, the reaction mixture was stirred for 24 h at room temperature. 100 mL of water was added to the reaction mixture and then extracted with ether (100×3). The combined ethereal extracts were then washed with 5% NaOH solution, until the aqueous phases were alkaline. The organic phase was washed with water until neutral and then dried over anhydrous magnesium sulfate, filtered and evaporated under reduced pressure. Purification by flash column chromatography (neutral alumina) afforded 910 mg (25%) of product as colorless oil. Product obtained in 10:90 (EtOAc:Hexanes).

$^1$H NMR (CDCl$_3$, 300 MHz): δ 7.79 (d, J=8.58 Hz, 1H), 6.81 (dd, J=8.70 Hz, 2.66 Hz, 1 H), δ 6.70 (d, J=2.68 Hz, 1 H), δ 3.84 (s, 3 H), δ 2.91(m, 2 H), δ 2.72 (m, 2H), δ 1.84 (m, 4 H).

2-Methoxy-5-(3,4,5-trimethoxyphenyl)-6,7,8,9-tet-rahydro-benzocyclohepten-5-ol (32)

200 mL of anhydrous ether was, added to 3,4,5-tri-methoxybromobenzene (1.23 g, 4.97 mmol) in a 500 mL round bottom flask under nitrogen. The temperature of the reaction mixture was brought to −78° C. n-Butyllithium (4.5 mL, 11.25 mmol) was added dropwise. The reaction mixture was then stirred until the temperature was raised gradually to −30° C. 30 (0.86 g, 4.5 mmol) dissolved in 25 mL of dry ether was added dropwise and the reaction mixture was allowed to stir until the temperature warmed up to room temperature. 25 mL of water was added and the product was extracted with ether (3×50), combined organic phases were dried over anhydrous magnesium sulfate, filtered and evaporated under reduced pressure. Purification by column chromatography (silica gel, 20:80 EtOAc:Hexanes) yielded 800 mg (49%) of 32 as pale yellow oil Rf: 0.16 (30:70, EtOAc:Hexanes).

3-Methoxy-9-(3,4,5-trimethoxy-phenyl)-6,7-dihy-dro-5H-benzocycloheptene(2)

A mixture of the 32 (800 mg, 2.23 mmol) in 20 mL of acetic acid and 100 mL of water, taken in a 250 mL round bottom flask were refluxed for 12 h. The reaction mixture was cooled and extracted with dichloromethane (3×25 mL) and the combined organic phases were dried over magnesium sulfate. The solvent evaporated and the crude product was purified by flash column chromatography (10:90 EtOAc:Hexanes), to afford 690 mg (91%) of 2 as white crystals. Rf: 0.43 (30:70, EtOAc:Hexanes).

$^1$H NMR (CDCl$_3$, 300 MHz): δ 6.97 (d, J=8.46 Hz, 1H), δ 6.83 (d, J=2.61 Hz, 1H), δ6.74 (dd, J=8.49 Hz, 2.73 Hz, 1H), δ 6.49 (s, 2H), δ 6.35 (t, J=7.32 Hz, 1H), δ 3.86 (s, 3H), δ 3.84 (s, 3H), δ 3.80 (s, 3H), δ 2.64 (t, J=6.99 Hz, 2H), δ 2.18 (p, J=7.05 Hz, 2H), δ 1.97 (m, 2H).

Synthesis of 3-Methoxy-8-(3,4,5-trimethoxy-phe-nyl)-6,7-dihydro-5H-benzocycloheptene
(1; see FIG. 1)

2-hydroxy-7-methoxy-2-(3,4,5-trimethoxyphenyl) benzosuberan (31)

3,4,5-trimethoxybromobenzene (0.91 g, 3.68 mmol) was charged in a 500 mL round bottom flask and put under nitrogen. 70 mL of anhydrous ether was added and the temperature was brought to −78° C. n-butyllithium (2.94 mL, 7.36 mmol) was added dropwise. The reaction mixture was then stirred until the temperature was raised gradually to −30° C. 28 (0.7 g, 3.68 mmol) dissolved in 20 mL of dry ether was added dropwise and the reaction mixture was allowed to stir until the temperature warmed up to room temperature. 25 mL of water was added to the reaction mixture and extracted with ether (3×30 mL), combined organic phases were dried over anhydrous Na$_2$SO$_4$, filtered and concentrated under reduced pressure. Purification by column chromatography (silica gel, 20:80, EtOAc:Hexanes) yielded 500 mg (29%) of 31 as pale yellow oil.

3-Methoxy-8-(3,4,5-trimethoxy-phenyl)-6,7-dihy-dro-5H-benzocycloheptene(1)

A mixture of the 31 (500 mg, 1.4 mmol) in 12 mL of acetic acid and 60 mL of water, taken in a 250 mL round bottom flask were refluxed for 12 h. The reaction mixture was cooled and extracted with dichloromethane (3×20 mL) and the combined organic phases were dried over magnesium sulfate. The solvent evaporated and the crude product was purified by flash column chromatography (10:90 EtOAc:Hexanes), to afford 60 mg (13%) of 1 as white crystals.

NMR data: $^1$H (CDCl$_3$, 300 MHz): δ 7.17 (d, J=7.87 Hz, 1H), δ 6.73 (m, 4H), δ 3.90 (s, 6H), δ 3.87 (s, 3H), δ 3.82 (s, 3H), δ 2.81 (t, J=6.21 Hz, 2H), δ 2.64 (t, J=6.60 Hz, 2H), δ 2.20 (p, J=6.16 Hz, 2H).

Synthesis of 2-Methoxy-6-(3,4,5-trimethoxy-phenyl)-8,9-dihydro-7H-benzocyclohepten-1-ol (3; see FIG. 1)

2-Methoxy-5,6,7,8-tetrahydro-naphthalen-1-ol (33)

2-Methoxy-5,6,7,8-tetrahydro-naphthalen-1-ol (33) was prepared according to the methods of Ghatak et al., (Ghatak, et al., *Tet. Lett.* (2003), 44: 4145) and as outlined below.

To a well-stirred solution of 6-methoxy-1,2,3,4-tetrahydronapthalene (14.05 g, 86.67 mmol) in sec-butyllithium (100 mL, 110 mmol) at 0° C., under nitrogen, was added freshly distilled N,N,N',N'-tetramethylethylenediamiene (13.61 mL) dropwise. After the addition was complete, the reaction mixture was stirred at room temperature for 1 h. Then, the reaction mixture was cooled again to 0° C. and trimethyl borate (12.55 mL, 110 mmol) was added dropwise and the reaction mixture was stirred for 1 h at room temperature. The reaction mixture was cooled back to 0° C. and 7 mL of glacial acetic acid was added dropwise, the reaction mixture was let to cool to 0° C. and then 35% wt. hydrogen peroxide in water (15 mL) was added dropwise. The reaction mixture was then allowed to stir at room temperature for 12 h. Saturated ammonium chloride (100 mL) was added. The organic phase was separated and collected, and the aqueous phase was extracted with ether. The combined organic phases were washed with brine (if necessary) and dried over anhydrous sodium sulfate, filtered, concentrated in vacuo. Purification by flash column chromatography (silica gel, 2:98 EtOAc:Hexanes) yielded 3.5 g (23%) of 33 along with 9.7 g (63.1%) of 7-hydroxy-6-methoxy-(1,2,3,4-tetrahydro)naphthalene (obtained in 5:95 EtOAc:Hexanes). Rf value for 33 is 0.48 (15:85 EtOAc:Hexanes), for 7-hydroxy-6-methoxy-1-tetrahydronapthalene 0.37.

$^1$H NMR (CDCl$_3$, 300 MHz): δ 6.67 (d, J=8.28 Hz, 1H), δ 6.58 (d, J=8.79 Hz, 1 H), δ 5.64 (s, 1H), δ 3.85 (s, 3H), δ 2.71 (t, J=3.03, 4H), δ 1.76 (m, 4H).

5-Isopropoxy-6-methoxy-1,2,3,4-tetrahydro-naphthalene (34)

5-Isopropoxy-6-methoxy-1,2,3,4-tetrahydro-naphthalene (34) was prepared according to the methods of Bringmann et al. (Bringmann et al., *J. Org. Chem.* (2002), 67 (16), 5595) and according to the methods outlined below.

33 (4.55 g, 25.5 mmol) was charged in a 250 mL round bottom flask, equipped with a reflux condenser, under nitrogen gas. 50 mL of anhydrous acetone was added followed by cesium carbonate (66.55 g, 204.3 mmol). 2-bromopropane (23.94 mL, 255.0 mmol) was added and the reaction mixture was refluxed for 12 h. The solvent was filtered and evaporated in vacuo and purified by flash column chromatography (slilica gel, 1:99 EtOAc:Hexanes) to afford 5.2 g (93%) of 5-isopropoxy-6-methoxy-1,2,3,4-tetrahydronaphtalene (34). Rf value: 0.615 (15:85 EtOAc:Hexanes).

$^1$H NMR (CDCl$_3$, 300 MHz): δ 6.75d, J=8.34 Hz, 1H), δ 6.69 (s, J=8.37 Hz, 1H), δ 4.46 (septet, J=6.18 Hz, 1H), δ 3.80 (s, 3H), δ 2.71 (m, 4H), δ 1.74 (m, 4H), δ 1.27 J=6.18)

5-Isopropoxy-6-methoxy-3,4-dihydro-2H-naphthalen-1-one (35)

34 (120 mg, 0.55 mmol) was weighed in a 100 mL round bottom flask and a solution of 5 mL of water:dioxane (5:95) was added and the reaction was set up under nitrogen. A solution of 2,4-dichloro-5,6-dicyanobenzoquinone (0.25 g, 1.09 mmol) dissolved in 5 mL of dioxane was added dropwise to the reaction mixture. The reaction mixture was stirred for 12 h. The solid separated was filtered and washed with ethylacetate. The filtrate was concentrated under reduced pressure and 10 mL of saturated sodium bicarbonate solution was added and the resulting reaction mixture was extracted with ether (3×20 mL) and the combined organic phases dried over anhydrous sodium sulfate, filtered and evaporated in vacuo. Purification by flash column chromatography (silica gel, 30:70 EtOAc:Hexanes) yielded 90 mg (71%) of 35. Rf value: 0.458 (40:60 EtOAc:Hexanes).

$^1$H NMR (CDCl$_3$, 300 MHz): δ 7.84 (d, J=8.73 Hz, 1H), δ 6.86 (d, J=8.73 Hz, 1H) δ 4.45 (septet, J=6.18 Hz, 1H), δ 3.89 (s, 3H), δ 2.95 (t, J=6.00 Hz, 2H), δ 2.59 (t, J=6.18 Hz, 2H), δ 2.06 (p, J=6.57 Hz, 2H) δ 1.28 (d, J=6.18 Hz, 6H).

5-Isopropoxy-6-methoxy-1-methylene-1,2,3,4-tetrahydro-naphthalene (36)

To a dry 250 mL 3-necked round bottom flask equipped with a reflux condenser and magnetic stir bar was added sodium hydride (1.09 g, 47.4 mmol) under nitrogen. 20 mL of anhydrous dimethylsulfoxide was added and the reaction mixture was heated to 70-75° C. for 30 min, until the evolution of hydrogen ceased. The reaction mixture turned green in color at this point, and then, the reaction mixture was cooled to room temperature and additional 15 mL of DMSO was added. Methyltriphenylphosphonium iodide (12.76 g, 31.57 mmol) was added in portions over a period of 30 min. 15 mL of additional DMSO was added and the reaction mixture was stirred for 20 minutes at room temperature. 35 (3.73 g, 15.8 mmol) dissolved in 5 mL of anhydrous DMSO was added to reaction mixture and the temperature was raised to 60-65° C., and stirred at that temperature for 8 h. The reaction mixture was poured into a 250 mL Erlenmeyer flask containing 75 mL ice and 75 mL of hexanes. The resulting mixture was stirred vigorously for 15 min, and then extracted with hexanes. The combined organic layers were washed DMSO:Water (1:1) and then dried over anhydrous sodium sulfate, filtered and evaporated under reduced pressure. Purification by flash column chromatography (silica gel 5:95, EtOAc:Hexanes) yielded 320 mg of 36 (10%). Rf −0.632, (30% ethylacetate in hexanes).

$^1$H NMR (CDCl$_3$, 300 MHz): δ 7.37 (d, J=8.70 Hz, 1H), δ 6.75 (d, J=8.70 Hz, 1H), δ 5.35 (s, 1H), δ 4.85 (s, 1H), δ 4.46 (septet, J=6.18 Hz, 1H), δ 3.83 (s, 3H), δ 2.82 (t, J=6.27 Hz, 2H), δ 2.48 (t, J=6.00 Hz, 2H), δ 1.83 (p, J=6.33 Hz, 2H), δ 1.27 (d, J=6.18 Hz, 6H).

1-Isopropoxy-2-methoxy-5,7,8,9-tetrahydro-benzocyclohepten-6-one (37)

1-Isopropoxy-2-methoxy-5,7,8,9-tetrahydro-benzocyclohepten-6-one (37) was prepared according to the methods of McMurry et al. (McMurry et al., *J. Org. Chem.* (1973), 38 (16), 2821) and as outlined below.

Preparation of cyanogen azide: Finely powedered cyanogen azide (0.51 g, 7.8 mmol) was added rapidly to a 0° C. solution of cynaogen bromide (0.83 g, 7.8 mmol) in 5 mL of anhydrous aceotnitrile. The reaction mixture was stirred for 4 h at 0° C. and clear supernatant solution containing cyanogen azide (0.53 g, 7.8 mmol) was drawn into a syringe to be used for the ring expansion reaction.

Ring expansion reaction: The exocyclic olefin (320 mg, 1.3 mmol) was charged in a 50 mL round bottom flask, and put under nitrogen. 5 mL of methanol:acetonitrile (1:1) was added to the reaction flask, and the reaction mixture was stirred at room temperature. To this was added freshly prepared cyanogen azide (0.53 g, 7.8 mmol) and the reaction mixture was stirred at room temperature for 48 h. 5 mL of 6 M of HCl was added and the reaction was stirred at 50° C. for 4 h. The reaction mixture was then cooled to room temperature, extracted with ether (2×30 mL). The ethereal extracts were washed with water until neutral and then dried over anhydrous sodium sulfate. The organic phase was then percolated through a column of basic alumina capped with a layer of celite to remove the explosive azides. Evaporation of the solvent followed by purification by flash column chromatography (8:92 EtOAc:Hexanes) yielded 110 mg (33%) of 37 (off-white solid). Rf: 0.476 (70:30 hexanes:ethylacetate).

$^1$H NMR (CDCl$_3$, 300 MHz): δ 6.83 (d, J=8.28 Hz, 1H), δ 6.71 (d, J=8.25 Hz, 1H), δ 4.43 (septet, J=6.14 Hz, 1H), δ 3.82 (s, 3H), δ 3.64 (s, 2H), δ 3.04 (t, J=6.36 Hz, 2H), δ 2.51 (t, J=6.90 Hz), δ 1.94 (p, J=6.90 Hz, 2H), δ 1.28 (d, J=6.15 Hz, 6H). $^{13}$C NMR (CDCl$_3$, 75 MHz): δ 209.58, 152.24, 144.47, 134.63, 126.91, 124.28, 109.98, 74.80, 55.67, 49.73, 43.27, 25.37, 24.46, 22.58.

1-Isopropoxy-2-methoxy-6-(3,4,5-trimethoxy-phenyl)-6,7,8,9-tetrahydro-5H-benzocyclohepten-6-ol (40)

3,4,5-trimethoxybromobenzene (1.49 g, 6.05 mmol) was dissolved in 200 mL of dry ether under nitrogen and the reaction mixture was cooled to −78° C. n-butyllithium (3.2 mL, 8.06 mmol) was added dropwise. The reaction mixture was then stirred until the temperature was raised gradually to −30° C. 37 (1 g, 4.03 mmol) dissolved in 25 mL of dry ether was added dropwise and the reaction mixture was allowed to stir until the temperature warmed up to room temperature. 30 mL of water was added and the organic phase was separated. The aqueous layer was then extracted with ether (2×50), and the combined organic phases were dried over anhydrous magnesium sulfate, filtered and evaporated under reduced pressure. Purification of the crude product by column chromatography (silica gel, 30:70 EtOAc:Hexanes) yielded 1.1 g (66%) of 40 as white crystals. Rf: 0.15 (70:30, Hex:EA).

4-Isopropoxy-3-methoxy-8-(3,4,5-trimethoxy-phenyl)-6,7-dihydro-5H-benzocycloheptene (41)

A mixture of the SM (40) (1.1 g, 2.64 mmol) in 30 mL of acetic acid and 100 mL of water, taken in a 250 mL round bottom flask were refluxed for 12 h. The reaction mixture was cooled and extracted with dichloromethane (3×25 mL) and the combined organic phases were dried over magnesium sulfate. The solvent evaporated and the crude product was purified by flash column chromatography (10:90 ethylacetate:hexanes), to afford 1 g (95%) of 4-Isopropoxy-3-methoxy-8-(3,4,5-trimethoxy-phenyl)-6,7-dihydro-5H-benzocycloheptene as white crystals. Rf:56 (60:40, Hex:EA)

$^1$H NMR (CDCl$_3$, 300 MHz): δ 6.93 (d, J=8.46 Hz, 1H), δ 6.74 (d, J=8.49 Hz, 1H), δ 6.71 (s, 1H), δ 6.70 (s, 2H), δ 4.40 (septet, J=6.18 Hz, 1H), δ 3.90 (s, 6H), δ 3.87 (s, 3H), δ 3.84 (s, 3H), δ 2.91 (t, J=6.06 Hz, 2 H), δ 2.60 (t, J=6.78 Hz, 2H), δ 2.16 (p, J=6.54 Hz, 2H), δ 1.27 (d, J=6.18 Hz, 6H).

2-Methoxy-6-(3,4,5-trimethoxy-phenyl)-8,9-dihydro-7H-benzocyclohepten-1-ol (3)

41 (220 mg, 0.55 mmol) was dissolved in 15 mL of anhydrous dichlromethane under nitrogen at room temperature. Aluminium chloride (147 mg, 1.1 mmol) was added and the reaction mixture was stirred for 10 minutes. 10 mL of water was added and the product was extracted in dichloromethane (2×20 mL) and the combined organic phases were dried over anhydrous sodium sulfate, evaporated under reduced pressure purified by column chromatography. The product 3, 81 mg (41% yield) was obtained in 10% ethylacetate in hexanes. Rf. 0.54 (60:40 Hex:EA).

$^1$H NMR (CDCl$_3$, 300 MHz): δ 6.76 (d, J=8.37 Hz, 1H), δ 6.71 (d, J=8.31 Hz, 1 H), δ 6.70 (s, 3H), δ 5.71 (s, 1H), δ 3.91 (s, 3H), δ 3.90 (s, 3H), δ 3.87 (s, 3H), δ 2.92 (t, J=6.12 Hz, 2H), δ 2.61 (t, J=6.12 Hz, 2H), δ 2.19 (p, J=6.60 Hz, 2H). $^{13}$C NMR (CDCl$_3$, 75 MHz): δ 152.89, 145.03, 142.49, 141.26, 140.24, 137.26, 131.69, 128.13, 126.83, 121.75, 107.68, 103.52, 60.85, 56.11, 32.85, 29.80, 24.89

Example 2

Synthesis of Optional Linkers

The compounds of the invention may further comprise a benzoyl substituent in which a carbonyl group is introduced between the core suberene (or dihydronapthalene) ring and the pendant aryl ring. Furthermore, the carbonyl group of the benzoyl substituent can be replaced with an oxygen to generate a new compound which maintains the same or similar biological efficacy with tubulin. These compounds may be prepared by an addition elimination reaction utilizing the trimethoxyphenolic anion as a nucleophile. Other linkage atoms between the aryl-aryl rings are conceivable as well, including thioethers (—S—), secondary alcohols (—CH(OH)—, and methylenes (—CH2-). These compounds are intended to form a one-atom bridge between the substituted aryl and the chromene ring. For example, the secondary alcohols can be created by reduction of corresponding ketones (—C=O)— with sodium borohydride, and methylenes can be created by reduction with trifluoroacetic acid. Alternatively, a single covalent bond can substitute for the 1-atom linker.

Figure 9:
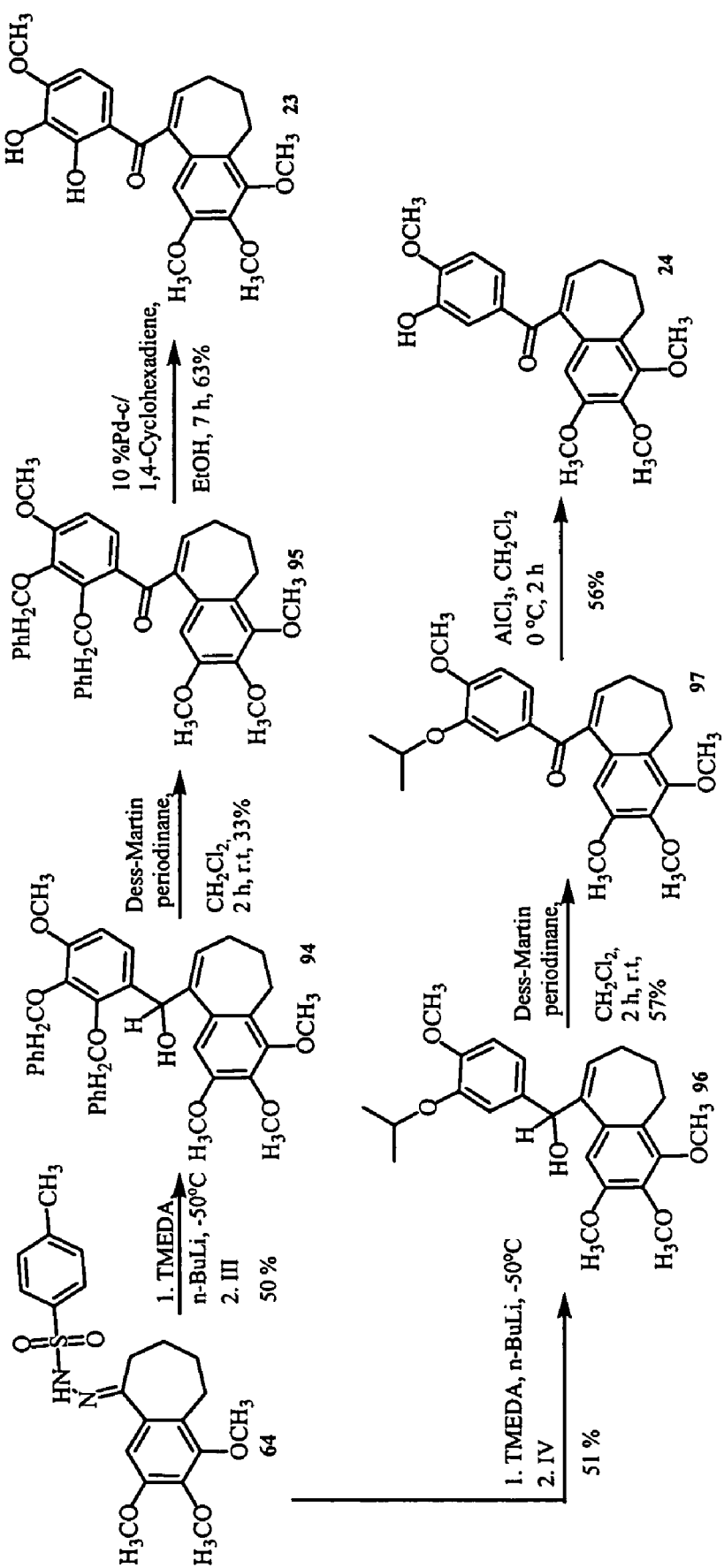
FIG. 9 depicts a route for the synthesis of Compounds 23 and 24, exemplary compounds of the invention.
Figure 10:
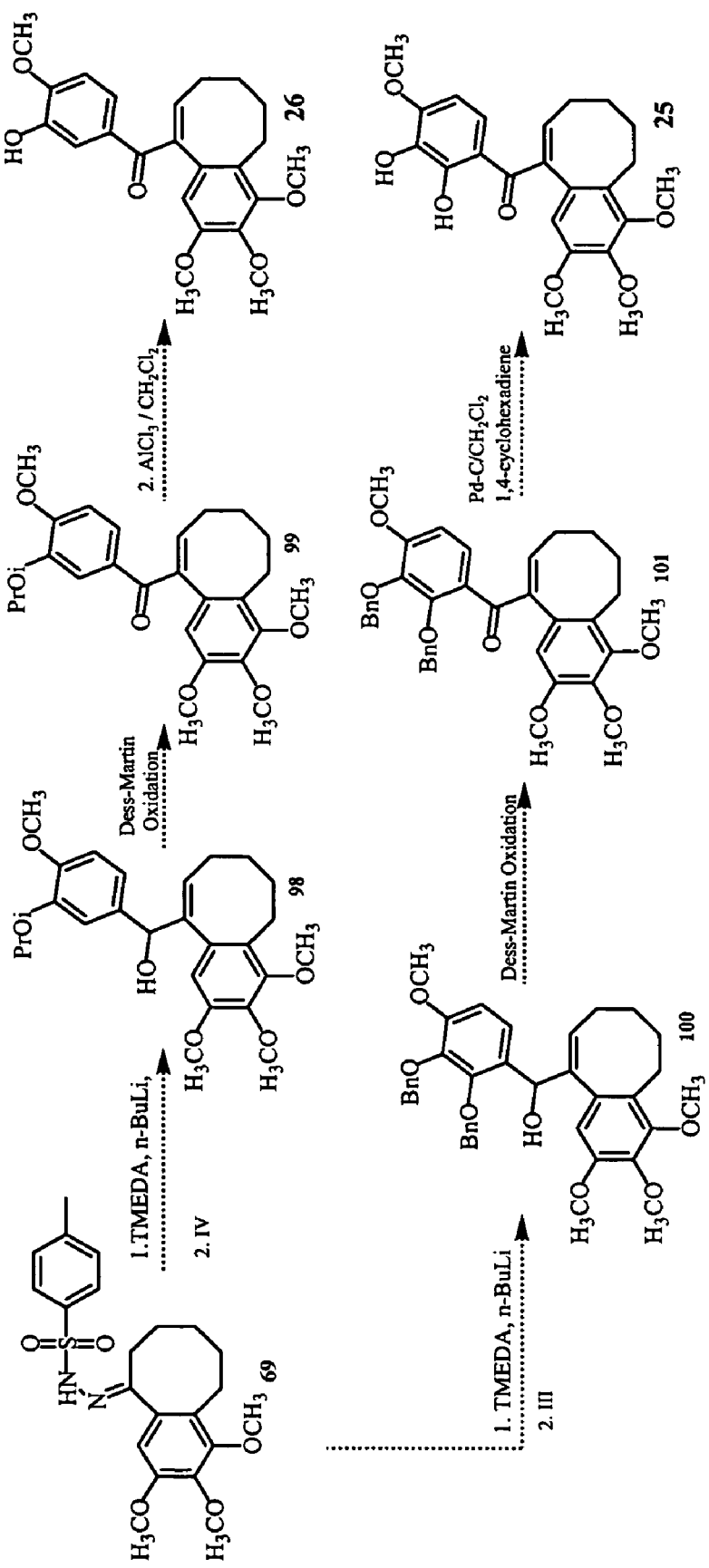
FIG. 10 depicts a route for the synthesis of Compounds 25 and 26, exemplary compounds of the invention.

Synthesis of (2,3-Dihydroxy-4-methoxy-phenyl)-(1,2,3-trimethoxy-8,9-dihydro-7H-benzocyclohepten-5-yl)-methanone (23; see FIG. 9)

(2,3-Dihydroxy-4-methoxy-phenyl)-(1,2,3-trimethoxy-8,9-dihydro-7H-benzocyclohepten-5-yl)-methanone (23) was prepared using methods known in the art (Atmaram et al, *Bioorg. Med. Chem. Lett.* (1999), 9, 2119; Koo, *JACS.* (1953), 75 (18), 1891; Pettit et al., *J. Med. Chem.* (2000), 43, 2731; Uffe et al., *Tet Lett.* (2005), 46, 4261) and as outlined below.

5-Oxo-5-(2,3,4-trimethoxy-phenyl)-pentanoic acid methyl ester (60)

75 g of polyphosphoric acid (Acros) was charged in a 250 mL round bottom flask, followed by addition of 1,2,3-trimethoxybenzene (5.0 g, 29.73 mmol), and mono-methylglutarate (6.516 g, 44.60 mmol). The reaction mixture was stirred mechanically for 2.5 h at 45° C. The reaction mixture was then poured into a 1000 mL beaker containing around 250 mL of ice, and stirred well until all the product precipitated out. The tan colored product was then filtered and washed with water and dried under vacuum. No, purification required at this stage. 6.78 g (77%) of product was obtained, which was pure by NMR.

$^1$H NMR (CDCl, 300 MHz): δ 7.48 (d, J=8.86 Hz, 1H), δ 6.71 (d, J=8.98 Hz, 1 H), δ 3.96 (s, 3H), δ 3.91 (s, 3H), δ 3.87 (s, 3H), δ 3.67 (s, 3H), δ 3.02 (t, J=7.14, 2H), δ 2.41 (t, J=7.40 Hz, 2H), δ 2.03 (p, J=7.16 Hz, 2H).

5-Oxo-5-(2,3,4-trimethoxy-phenyl)-pentanoic acid (61)

6.78 g of sodium hydroxide was dissolved in 25 mL of methanol in a 100 mL round bottom flask. The reaction mixture was cooled to room temperature and 60 (6.78 g, 22.90 mmol) was added followed by 5 mL of water and the reaction mixture was refluxed for 30 min. The solvent was evaporated under reduced pressure and the reaction mixture was neutralized with dilute hydrochloric acid and the reaction mixture was extracted with ether (100×3) and the combined organic phases were washed with water and dried over sodium sulfate and solvent evaporated under reduced pressure. The crude product was purified by column chromatography (20:80 EA:Hex) to yield 7.05 g of 61 (quantitative yield).

$^1$H NMR (CDCl$_3$, 300 MHz): δ 7.50 (d, J=8.88 Hz, 1H), δ 6.70 (d, J=8.91 Hz, 1 H), δ 3.96 (s, 3H), δ 3.91 (s, 3H), δ 3.87 (s, 3H), δ 3.05 (t, J=7.08, 2H), δ 2.50 (t, J=7.68 Hz, 2H), δ 2.04 (p, J=6.95 Hz, 2H).

5-(2,3,4-Trimethoxy-phenyl)-pentanoic acid (62)

5-Oxo-5-(2,3,4-trimethoxy-phenyl)-pentanoic acid (7.05 g 24.97 mmol) was dissolved in 100 mL of anhydrous ethanol under inert atmosphere and 2.0 g of Pd—C was added. The nitrogen gas was removed by vacuum, and hydrogen gas was passed into the flask. The reaction mixture was stirred for 1 h. The completion of the reaction was confirmed by TLC. The reaction mixture was filtered through celite. The solvent was evaporated under reduced pressure to obtain 6.48 g (97.74%) of 62 (colorless oil) which was pure by NMR.

$^1$H NMR (CDCl$_3$, 300 MHz): δ 6.81 (d, J=8.48 Hz, 1H), δ 6.60 (d, J=8.50 Hz, 1 H), δ 3.87 (s, 3H), δ 3.86 (s, 3H), δ 3.84 (s, 3H), δ 2.60 (t, J=7.65, 2H), δ 2.39 (t, J=7.42 Hz, 2H), δ 1.66 (m, 4H).

1,2,3-Trimethoxy-6,7,8,9-tetrahydro-benzocyclohepten-5-one (63)

60 (6.48 g, 24.19 mmol) was weighed in a 250 mL round bottom flask, followed by addition of 75 g of polyphosphoricacid. The reaction mixture was stirred mechanically for 2.5 h at 45° C. The reaction mixture was poured into 250 mL of ice and stirred until the entire polyphoshoric acid dissolved. The resultant solution was extracted with dichloromethane (100×3), and the combined organic phases were dried over anhydrous Na$_2$SO$_4$, filtered and evaporated under reduced pressure. Purification by column chromatography (92:8 Hexanes:Ethylacetate), yielded 3.0 g (50%) of 63. The product was pure by NMR.

$^1$H NMR (CDCl$_3$, 300 MHz): δ 7.13 (s, 1H), δ 3.93 (s, 3H), δ 3.88 (s, 3H), δ 3.84 (s, 3H), δ 2.94 (t, 2H), δ 2.73 (m, 2H), δ 1.81 (m, 4H)

$^{13}$C NMR (CDCl$_3$, 75 MHz): δ 204.93, 151.53, 150.95, 145.86, 134.37, 128.86, 107.44, 61.37, 60.84, 55.95, 40.75, 24.98, 22.93, 20.91.

(1,2,3-trimethoxy-6,7,8,9-tetrahydrobenzoheptene)-5-p-toluenesulfonylhydrazone (64)

(1,2,3-trimethoxy-6,7,8,9-tetrahydrobenzoheptene)-5-p-toluenesulfonylhydrazone (64) was prepared according to the methods of Pinney et al. (Pinney et al., *Steroids*. (1992), 57 (5), 222) and as outlined below.

64 (8.21 g, 32.81 mmol) was dissolved in 150 mL of absolute ethanol followed by p-toluenesulfonylhydrazide (6.11 g. 32.81 mmol) under nitrogen. The reaction mixture was stirred for five minutes at room temperature until the solid dissolved. P-toluenesulfonic acid monohydrate (0.28 g, 0.05 mmol) was added and the reaction mixture was allowed to stir for 12 h. The product precipitated out as white solid, which was then filtered and washed with ice-cold ethanol and dried (13.50 g, 98% yield). Rf: 0.325 (60:40 Hex:EA).

$^1$H NMR (DMSO-d6, 300 MHz): δ 10.33 (s, 1H), δ 7.83 (s-broad, 2H), δ 7.51 (s-broad, 2H), δ 6.38 (s, 1H), δ 3.73 (s, 3H), δ 3.69 (s, 6H), δ 2.73 (m, 7H), δ 1.60 (s, 2H), δ 1.47 (s, 2H).

(2,3-Bis-benzyloxy-4-methoxy-phenyl)-(1,2,3-trimethoxy-8,9-dihydro-7H-benzocyclohepten-5-yl)-methanol (94)

36 mL of freshly distilled TMEDA was charged in a 250 mL round bottom flask under nitrogen. n-BuLi (5.89 mL, 14.72 mmol) was added and the reaction mixture was cooled to −50° C. 64 (1.54 g, 3.68 mmol) was added and the reaction mixture was then stirred to warm up to room temperature, which took approximately about 7 h. 2,3-dibenzlyoxy-4-methoxybenzaldehyde (5.13 g, 14.72 mmol) was then added and the reaction mixture was stirred for 1 h. 25 mL of water was added and the product was extracted with ethyl acetate (2×100 mL). The combined organic phases were washed with aqueous CuSO$_4$, followed by brine, dried over anhydrous sodium sulfate, filtered and evaporated under reduced pressure. Purification of the crude by column chromatography (16:84, EA:Hex) yielded 1.02 g (48% yield) of product (94) as pale yellow oil. Rf: 0.56 (60:40 Hex:EA).

$^1$H NMR (CDCl$_3$, 300 MHz): δ 7.35 (m, 10H), δ 7.11 (d, J=8.66 Hz, 1H), δ 6.67 (d, J=8.68 Hz, 1H), δ 6.63 (s, 1H), δ 6.06 (t, J=7.11 Hz, 1H), δ 5.85 (d, J=4.27 Hz, 1H), δ 5.13 (d, J=10.90 Hz, 1H), δ 5.03 (d, J=10.90 Hz, 1H), δ 5.00 (s, 2H), δ 3.85 (s, 3H), δ 3.82 (s, 6H), δ 3.63 (s, 3H), δ 2.50 (t, J=7.07, 2H), δ 2.04 (t, J=6.97, 2H), δ 1.84 (m, 2H).

(2,3-Bis-benzyloxy-4-methoxy-phenyl)-(1,2,3-trimethoxy-8,9-dihydro-7H-benzocyclohepten-5-yl)-methanone (95)

94 (0.94 g, 1.62 mmol) was dissolved in 20 mL of dry dichloromethane and was added to a solution of Dess-Martin periodinane (2.7 g, 6.5 mmol) in dry dichloromethane under nitrogen. The reaction mixture was stirred for 1.30 h and then water (30 mL) was added, followed by 1.3 M NaOH solution (50 mL) and 50 mL of dichloromethane. The organic layer was washed with 1.3 M NaOH solution (50 mL), followed by 100 mL of water. The organic phase was dried over anhydrous sodium sulfate, filtered and then the solvent was removed under reduced pressure. The crude was purified by column chromatography (10:90, EtOAc:Hexanes) to yield a pale yellow oil (0.69 g, 73% yield) as product. Rf: 0.43 (60:40 Hex: EA).

NMR data: $^1$H(CDCl$_3$, 300 MHz): δ 7.40 (m, 10H), δ 7.11 (d, J=8.47 Hz, 1H), δ 6.78 (t, J=7.30 Hz, 1H), δ 6.72 (d, J=8.54 Hz, 1H), δ 6.61 (s, 1H), δ 5.09 (s, 2H), δ 5.02 (s, 2H), δ 3.90 (s, 3H), δ 3.89 (s, 3H), δ 3.85 (s, 3H), δ 3.70 (s, 3H), δ 2.51 (t, J=6.50, 3H), δ 2.04 (m, 4H).

(2,3-Dihydroxy-4-methoxy-phenyl)-(1,2,3-trimethoxy-8,9-dihydro-7H-benzocyclohepten-5-yl)-methanone (23)

(2,3-Dihydroxy-4-methoxy-phenyl)-(1,2,3-trimethoxy-8,9-dihydro-7H-benzocyclohepten-5-yl)-methanone (23) was prepared according to the methods of Felix et al. (Felix, et al., J. Org. Chem. (1978), 43 (21), 4194) and as outlined below.

95 (0.69 g, 1.19 mmol) was dissolved in 20 mL of anhydrous EtOH under nitrogen and the reaction mixture was immersed in a water bath to maintain a temperature of 25° C. 1.2 g of Pd—C was added followed by 1,4-cyclohexadiene (1.13 mL, 11.90 mmol) and the reaction mixture was stirred for 7 h. The reaction mixture was monitored for completion by TLC (Rf: 0.32, 60:40 Hex:EA). The reaction mixture was filtered through celite, washed with ethylacetate, rotavaped and purified by column chromatography (20:80 EtOAc:Hexanes) to obtain 0.3 g (63%) of 23 as yellow oil.

NMR data: $^1$H (CDCl$_3$, 300 MHz): δ 12.49 (s, 1H), δ 7.05 (d, J=9.03 Hz, 1H), δ 6.66 (t, J=6.84 Hz, 1H), δ 6.41 (s, 1H), δ 6.37 (d, J=9.06 Hz, 1H), δ 5.69 (s, 1H), δ 3.90 (s, 3H), δ 3.88 (2s, 6H), δ 3.69 (s, 3H), δ 2.73 (t, J=6.52 Hz, 2H), δ 2.16 (m, 4H).

$^{13}$C (CDCl$_3$, 75 MHz): δ 200.76, 151.99, 151.37, 151.07, 141.81, 141.45, 139.10, 133.325, 132.38, 127.24, 125.16, 115.99, 114.33, 107.84, 102.54, 61.55, 60.79, 56.11, 55.98, 33.87, 26.00, 23.82.

Synthesis of (3-Hydroxy-4-methoxy-phenyl)-(1,2,3-trimethoxy-8,9-dihydro-7H-benzocyclohepten-5-yl)-methanone (24; see FIG. 9)

(3-Isopropoxy-4-methoxy-phenyl)-(1,2,3-trimethoxy-8,9-dihydro-7H-benzocyclohepten-5-yl)-methanol (96)

20 mL of freshly distilled TMEDA was charged in a 250 mL round bottom flask under nitrogen. n-BuLi (4.8 mL, 9.60 mmol) was added and the reaction mixture was cooled to −50° C. 68 (1.0 g, 2.40 mmol) was added and the reaction mixture was then stirred to warm up to room temperature, which took approximately about 7 h. 3-isopropoxy-4-methoxybenzaldehyde (1.9 g, 9.60 mmol) was then added and the reaction mixture was stirred for 1 h. 25 mL of water was added and the product was extracted with ethyl acetate (2×50 mL). The combined organic phases were washed with aqueous CuSO$_4$, followed by brine, dried over anhydrous sodium sulfate, filtered and evaporated under reduced pressure. Purification of the crude by column chromatography (16:84, EA:Hex) yielded 0.3 g (29% yield) of 96 as pale yellow oil. Rf: 0.30 (60:40 Hex:EA).

$^1$H NMR (CDCl$_6$, 300 MHz): δ 6.91 (m, 2H), δ 6.79 (d, J=8.22 Hz, 1H), δ 6.65 (s, 1H), δ 6.27 (t, J=8.00 Hz, 1H), δ 5.53 (s, 1H), δ 4.43 (sep, J=6.09 Hz, 1H), δ 3.85 (s, 3H), δ 3.80 (2s, 6H), δ 3.71 (s, 3H), δ 2.42 (m, 2H), δ 2.03 (m, 2H), δ 1.87 (m, 2H), δ 1.28 (d, J=6.02 Hz, 6H).

(3-Isopropoxy-4-methoxy-phenyl)-(1,2,3-trimethoxy-8,9-dihydro-7H-benzocyclohepten-5-yl)-methanone (97)

96 (0.30 g, 0.70 mmol) dissolved in 20 mL of dry dichloromethane was added to a solution of Dess-Martin periodinane (1.48 g, 3.50 mmol) in dry dichloromethane under nitrogen. The reaction mixture was stirred for 1.30 h at room temperature and then water (30 mL) was added, followed by 1.3 M NaOH solution (50 mL) and 50 mL of dichloromethane. The organic layer was washed with 1.3 M NaOH solution (50 mL), followed by 100 mL of water. The organic phase was dried over anhydrous sodium sulfate, filtered and then the solvent was removed under reduced pressure. The crude was purified by column chromatography (10:90, EtOAc:Hexanes) to yield a pale yellow oil (0.170 g, 57% yield) as product 97. Rf: 0.62 (40:60 Hex:EA).

$^1$H NMR (CDCl$_3$, 300 MHz): δ 7.40 (dd, J=8.40 Hz, 2.03 Hz, H), δ 7.31 (d, J=2.00 Hz, 1H), δ 6.80 (m, 2H), δ 6.47 (s, 1H), δ 4.47 (sep, J=6.12 Hz, 1H), δ 3.90 (s, 3H), δ 3.88 (2s, 6H), δ 3.69 (s, 3H), δ 2.75 (t, J=6.68 Hz, 2H), δ 2.15 (m, 4H), δ 1.31 (d, J=6.07 Hz, 6H).

(3-Hydroxy-4-methoxy-phenyl)-(1,2,3-trimethoxy-8,9-dihydro-7H-benzocyclohepten-5-yl)-methanone (24)

97 (0.07 g, 0.16 mmol) was dissolved in 10 mL of anhydrous CH$_2$Cl$_2$ under nitrogen at 0° C. Anhydrous AlCl$_3$ (44 mg, 0.33 mmol) was added and the reaction mixture was stirred for 2 h at 0° C. Saturated NH$_4$Cl (5 mL) was added and the organic phase was separated. The aqueous layer was extracted with CH$_2$Cl$_2$ (10 mL) and the combined organic phases were dried over Na$_2$SO$_4$, filtered, solvents evaporated under reduced pressure. The crude product was purified by column chromatography (30:70 EtOAc:Hexanes) to yield tan colored oil as product 24 (35 mg, 56% yield). Rf: 0.23 (60:40 Hex:EA).

$^1$H NMR (CDCl$_3$, 300 MHz): δ 7.41 (d, J=2.06 Hz, 1H), δ 7.34 (dd, J=8.36 Hz, 2.08 Hz, H), δ 6.84 (d, J=8.41 Hz, 1H), δ 6.79 (t, J=6.95 Hz, 1H), δ 6.53 (s, 1H), δ 3.96 (s, 3H), δ 3.90 (s, 3H), δ 3.88 (s, 3H), δ 3.72 (s, 3H), δ 2.72 (t, J=6.62 Hz, 2H), δ 2.14 (m, 4H).

$^{13}$C NMR (CDCl$_3$, 75 MHz): δ 195.77, 151.19, 150.15, 145.16, 142.23, 141.62, 141.21, 132.50, 131.65, 127.34, 132.43, 115.90, 109.67, 108.46, 61.53, 60.80, 56.02, 55.93, 33.82, 26.04, 23.75.

Figure 8:
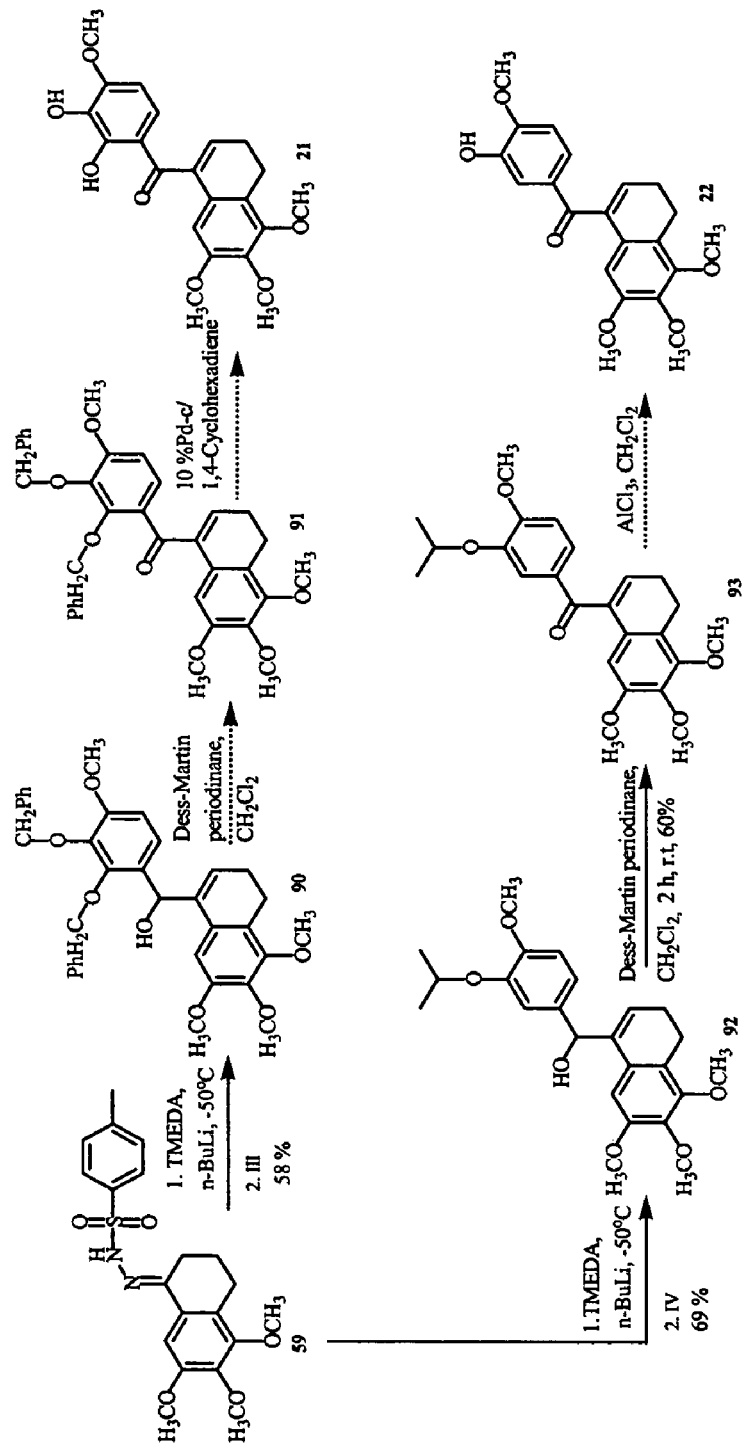
FIG. 8 depicts a route for the synthesis of Compounds 21 and 22, exemplary compounds of the invention.

Synthesis of (3-Hydroxy-4-methoxy-phenyl)-(5,6,7-trimethoxy-3,4-dihydro-naphthalen-1-yl)-methanone (22; see FIG. 8)

4-Oxo-4-(2,3,4-trimethoxy-phenyl)-butyric acid methyl ester (55)

A mixture of 75 g of polyphosphoric acid (Acros), 1,2,3-trimethoxybenzene (5.0 g, 29.73 mmol), and mono-methyl succinate (5.9 g, 44.59 mmol) were mechanically stirred at 45° C. for 2.5 h. The reaction mixture was then poured into a 1000 mL beaker containing round 250 mL of ice, and stirred well until all the product was precipitated out. The tan colored product was then filtered and washed with water and dried under vacuum. 6.1 g (72%) of 55 was obtained, which was pure by NMR.

$^1$H NMR (CDCl$_3$, 300 MHz): δ 7.56 (d, J=8.89 Hz, 1H), δ 6.72 (d, J=8.91 Hz, 1 H), δ 3.99 (s, 3H), δ 3.91 (s, 3H), δ 3.87 (s, 3H), δ 3.70 (s, 3H), δ 3.31 (t, J=6.57 Hz, 2H), δ 2.71 (t, J=6.57 Hz, 2H).

4-Oxo-4-(2,3,4-trimethoxy-phenyl)-butyric acid (56)

5.95 g of sodium hydroxide was dissolved in 200 mL of methanol in a 500 mL round bottom flask. The reaction mixture was cooled to room temperature and 55 (6.78 g, 22.90 mmol) was added followed by 20 mL of water and 100 mL of methanol and the reaction mixture was refluxed for 30 min. The solvent was evaporated under reduced pressure and the reaction mixture was neutralized with dilute hydrochloric acid and the reaction mixture was extracted with ether (100× 3) and the combined organic phases were washed with water and dried over sodium sulfate and solvent evaporated under reduced pressure. The crude product was purified by column chromatography (20:80 EtOAc:Hexanes) to yield 5.43 g of 56 as tan colored solid (94%).

¹H NMR (CDCl₃, 300 MHz): δ 7.55 (d, J=8.87 Hz, 1H), δ 6.72 (d, J=8.90 Hz, 1 H), δ 3.99 (s, 3H), δ 3.91 (s, 3H), δ 3.87 (s, 3H), δ 3.33 (t, J=6.60, 2H), δ 2.74 (t, J=6.50 Hz, 2H).

4-(2,3,4-Trimethoxy-phenyl)-butyric acid (57)

56 (5.43 g 20.24 mmol) was charged in a 250 mL round bottom flask, and 100 mL of anhydrous ethanol was added followed by addition of 1.0 g of Pd—C, and the reaction flask was put under vacuum, until all the air in the reaction flask was evacuated. Then, hydrogen gas was passed into the flask using a balloon filled with hydrogen gas. The reaction mixture was stirred for 1 h. The completion of the reaction was confirmed by TLC. The reaction mixture was filtered through celite. The solvent was evaporated under reduced pressure to obtain 5.42 g (quantitative) of 57 as colorless oil Rf: 0.45 (70:30 Hex:EA).
¹H NMR (CDCl₃, 300 MHz): δ 6.82 (d, J=8.40 Hz, 1H), δ 6.60 (d, J=8.47 Hz, 1 H), δ 3.87(2s, 6H), δ 3.84 (s, 3H), δ 2.59 (t, J=7.19, 2H), δ 2.33 (t, J=7.36 Hz, 2H), δ 1.89 (p, J=7.41 Hz, 2H).

5,6,7-Trimethoxy-3,4-dihydro-2H-naphthalen-1-one (58)

59 (4.44 g, 17.46 mmol) was charged in a 250 mL round bottom flask, followed by addition of 80 g of polyphosphoricacid. The reaction was stirred mechanically for 4 h at 70° C. The reaction mixture was poured into 250 mL of ice and the product precipitated out as tan colored solid, which was filtered and dried under high vacuum to yield 2.96 g of product (72%). Rf: 0.36 (70:30 Hex:EA)
¹H NMR (CDCl₃, 300 MHz): δ 7.39 (s, 1H), δ 3.94 (s, 3H), δ 3.89 (s, 3H), δ 3.86 (s, 3H) δ 2.88 (t, J=5.92, 2H), δ 2.60 (t, J=5.97 Hz, 2H), δ 2.08 (p, J=6.10 Hz, 2H).

(5,6,7-trimethoxy-3,4-dihydro-2H-napthalene)-1-p-toluenesulfonylhydrazone (59)

(5,6,7-trimethoxy-3,4-dihydro-2H-napthalene)-1-p-toluenesulfonylhydrazone (59) was prepared according to the methods of Pinney et al. (Pinney et al., *Steroids.* (1992), 57 (5), 222) and as outlined below.

63 (2.96 g g, 12.53 mmol) was dissolved in 150 mL of absolute ethanol followed by p-toluenesulfonylhydrazide (2.33 g. 12.53 mmol) under nitrogen. The reaction mixture was stirred for five minutes at room temperature until the solid dissolved. p-Toluenesulfonic acid monohydrate (0.11 g, 0.63 mmol) was added and the reaction mixture was allowed to stir for 12 h. The product precipitated out as white solid, which was then filtered and washed with ice-cold ethanol and dried (4.65 g, 92% yield).

(3-Isopropoxy-4-methoxy-phenyl)-(5,6,7-trimethoxy-3,4-dihydro-naphthalen-1-yl)-methanol (92)

25 mL of freshly distilled TMEDA was charged in a 100 mL round bottom flask under nitrogen. n-BuLi (4.65 mL, 9.89 mmol) was added and the reaction mixture was cooled to −50° C. 59 (1.0 g, 2.47 mmol) was added and the reaction mixture was then stirred to warm up to room temperature, which took approximately about 7 h. 3-isopropoxy-4-methoxybenzaldehyde (1.92 g, 9.89 mmol) was then added and the reaction mixture was stirred for 1 h. 25 mL of water was added and the product was extracted with ethyl acetate (2×100 mL). The combined organic phases were washed with aqueous CuSO₄, followed by brine, dried over anhydrous sodium sulfate, filtered and evaporated under reduced pressure. Purification of the crude by column chromatography (16:84, EA:Hex) yielded 0.70 g (69% yield) of product as pale yellow oil. Rf: 0.31 (40:60 EtOAc:Hexanes).
NMR data: ¹H (CDCl₃, 300 MHz): δ 6.98 (m, 2H), δ 6.66 (s, 1H), δ 6.16 (t, J=4.57 Hz, 1H), δ 5.64 (s, 1H), δ 4.49 (sep, J=6.09 Hz, 1H), δ 3.84 (s, 6H), δ 3.81 (s, 3H), δ 3.66 (s, 3H), δ 2.73 (t, J=7.80 Hz, 2H), δ 2.31 (m, 2H), δ 1.31 (dd, J=6.09 Hz, 6H).

(3-Isopropoxy-4-methoxy-phenyl)-(5,6,7-trimethoxy-3,4-dihydro-naphthalen-1-yl)-methanone (93)

SM (92) (0.94 g, 1.62 mmol) was dissolved in 20 mL of dry dichloromethane and was added to a solution of Dess-Martin periodinane (2.7 g, 6.5 mmol) in dry dichloromethane under nitrogen. The reaction mixture was stirred for 1.30 h and then water (30 mL) was added, followed by 1.3 M NaOH solution (50 mL) and 50 mL of dichloromethane. The organic layer was washed with 1.3 M NaOH solution (50 mL), followed by 100 mL of water. The organic phase was dried over anhydrous sodium sulfate, filtered and then the solvent was removed under reduced pressure. The crude was purified by column chromatography (10:90, EtOAc:Hexanes) to yield a pale yellow oil (0.69 g, 73% yield) as product. Rf: 0.43 (40:60 EtOAc: Hexanes).
NMR data: ¹H (CDCl₃, 300 MHz): δ 7.49 (m, 2H), δ 6.87 (d, J=8.30 Hz, 1H), δ 6.69 (s, 1H), δ 6.40 (t, J=4.70 Hz, 1H), δ 4.61 (sep, J=6.08 Hz, 1H), δ 3.92 (s, 3H), δ 3.88 (s, 3H), δ 3.87 (s, 3H), δ 3.73 (s, 3H), δ 2.84 (t, J=7.85 Hz, 2H), δ 2.44 (m, 2H), δ 1.37 (dd, J=6.09 Hz, 6H).

Figure 4:
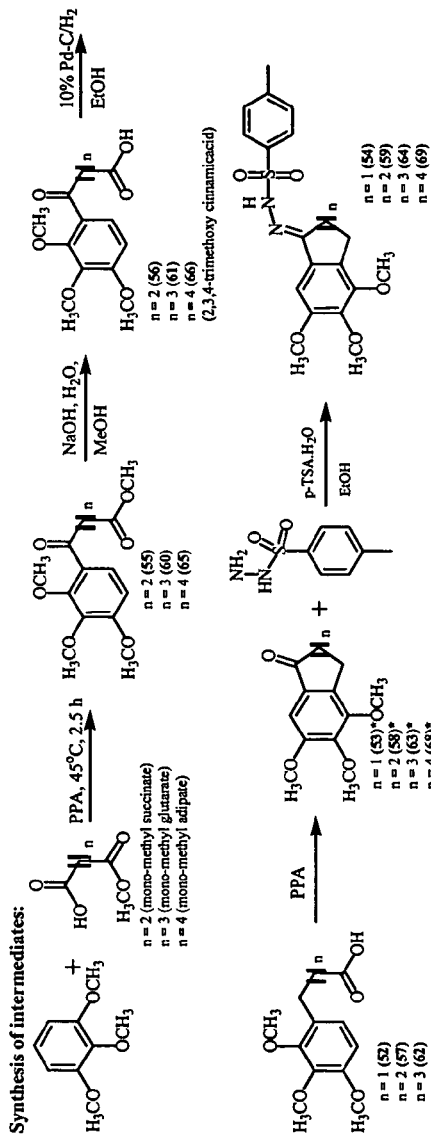
FIG. 4 depicts a route for the synthesis of various intermediates used in the synthesis of the compounds of the invention, including a listing of literature references describing the synthesis of intermediates I, II, III and IV.
Figure 4:
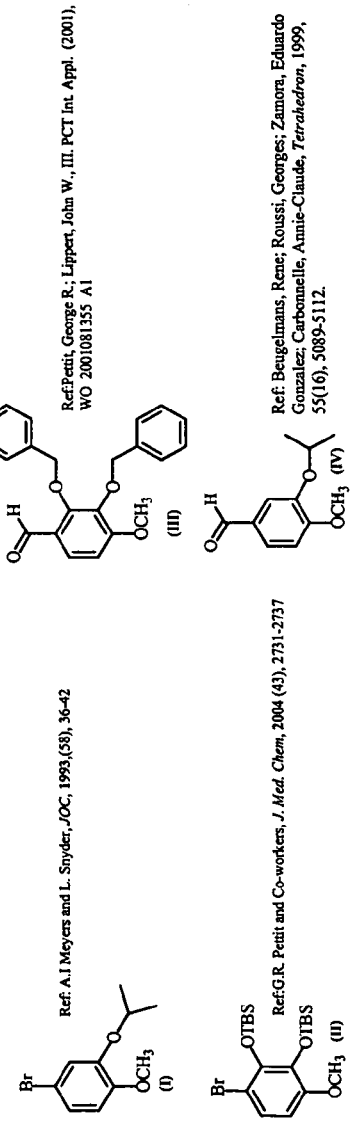

Synthesis of (7,8,9-trimethoxy-3,4,5,6-tetrahydro-2H-napthalene)-1-p-toluenesulfonylhydrazone (69; see FIG. 4)

6-Oxo-6-(2,3,4-trimethoxy-phenyl)-hexanoic acid methyl ester (65)

150 g of polyphosphoric acid (Acros) was added to a mixture of 1,2,3-trimethoxybenzene (10.0 g, 59.47 mmol), and mono-methyl adipate (13.04 mL g, 89.20 mmol) in a 250 mL round bottom flask equipped with a mechanical stirrer. The reaction mixture was stirred for 2.5 h at 45° C. The reaction mixture was then poured into a 1000 mL beaker containing around 500 mL of ice, and stirred well. Tan colored product precipitated out which was then filtered and washed with water and dried under vacuum. 17.18 g (93%) of 65 was obtained, which was pure by NMR. Rf: 0.42 (40:60 EtOAc: Hexanes)
¹H NMR (CDCl₃, 300 MHz): δ 7.44 (d, J=8.84 Hz, 1H), δ 6.68 (d, J=8.88 Hz, 1 H), δ 3.94 (s, 3H), δ 3.88 (s, 3H), δ 3.85 (s, 3H), δ 3.64 (s, 3H), δ 2.95 (t, J=6.96, 2H), δ 2.34 (t, J=7.02 Hz, 2H), δ 1.68 (m, 4H).

6-Oxo-6-(2,3,4-trimethoxy-phenyl)-hexanoic acid (66)

17 g of sodium hydroxide was dissolved in 200 mL of methanol in a 1000 mL round bottom flask. The reaction mixture was cooled to room temperature and 66 (6.78 g, 22.90 mmol) was added followed by 60 mL of water and 300 mL of anhydrous methanol, and the reaction mixture was refluxed for 30 min. The solvent was evaporated under reduced pressure and the reaction mixture was neutralized with dilute hydrochloric acid and the reaction mixture was extracted with ether (200×3) and the combined organic phases were washed with water and dried over sodium sulfate and solvent evaporated under reduced pressure. The crude product was purified by column chromatography (30:70 EA:Hex) to yield 12.86 g of 57 as pale yellow colored oil (78%). Rf: 0.15 (40:60 EtOAc:Hexanes).

$^1$H NMR (CDCl$_3$, 300 MHz): δ 7.47 (d, J=8.85 Hz, 1H), δ 6.70 (d, J=8.89 Hz, 1 H), δ 3.96 (s, 3H), δ 3.90 (s, 3H), δ 3.87 (s, 3H), δ 2.98 (t, J=6.78, 2H), δ 2.41 (t, J=7.07 Hz, 2H), δ 1.72 (m, 4H).

6-(2,3,4-Trimethoxy-phenyl)-hexanoic acid (67)

57 (12.86 g 43.40 mmol) was charged in a 250 mL round bottom flask, and 300 mL of anhydrous ethanol was added followed by addition of 4.0 g of 10% wt. Pd—C, and the reaction flask was put under vacuum, until all the air in the reaction flask was evacuated. Then, hydrogen gas was passed into the flask using a balloon filled with hydrogen gas. The reaction mixture was stirred for 12 h. The completion of the reaction was confirmed by TLC. The reaction mixture was filtered through celite. The solvent was evaporated under reduced pressure to obtain 11.7 g (96%) of 67 as colorless oil Rf: 0.49 (50:50 Hex:EA).

$^1$H NMR (CDCl$_3$, 300 MHz): δ 6.80 (d, J=8.48 Hz, 1H), δ 6.59 (d, J=8.47 Hz, 1 H), δ 3.86 (s, 6H), δ 3.83 (s, 3H), δ 2.53 (t, J=7.46, 2H), δ 2.33 (t, J=7.41 Hz, 2H), δ 1.64 (m, 4H) δ 1.37 (m, 2H).

1,2,3-Trimethoxy-7,8,9,10-tetrahydro-6H-benzocyclooctan-5-one (68)

A mixture of 61 (2.0 g, 7.06 mmol) and 40 g of polyphosphoricacid were stirred mechanically for 4 h at 45° C. The reaction mixture was poured into 100 mL of ice and the resultant aqueous solution was extracted with DCM (2×100 mL). The combined organic phases were washed with water, followed by brine, dried over anhydrous Na$_2$SO$_4$, filtered and evaporated. The crude product was then purified by column chromatography (7:93 EtOAc:Hexanes), to obtain 1.32 g of 65 as colorless oil (71%). Rf: 0.38 (75:25 Hexanes:EtOAc)

$^1$H NMR (CDCl$_3$, 300 MHz): δ 6.99 (s, 1H), δ 3.91 (s, 3H), δ 3.90 (s, 3H), δ 3.89 (s, 3H) δ 2.90 (t, J=5.95, 2H), δ 2.57 (t, J=6.86 Hz, 2H), δ 1.82 (m, 2H), δ 1.52 (m, 2H), δ 1.27 (m, 2H).

(5,6,7-trimethoxy-3,4-dihydro-2H-napthalene)-1-p-toluenesulfonylhydrazone (69)

68 (1.32 g g, 4.99 mmol) was dissolved in 30 mL of absolute ethanol followed by p-toluenesulfonylhydrazide (0.93 g. 4.99 mmol) under nitrogen. The reaction mixture was stirred for five minutes at room temperature until the solid dissolved. p-Toluenesulfonic acid monohydrate (0.043 g, 0.25 mmol) was added and the reaction mixture was allowed to stir for 12 h. The product precipitated out as white solid, which was then filtered and washed with ice-cold ethanol and dried (1.27 g, 59% yield).

$^1$H NMR (DMSO-d$_6$, 300 MHz): δ 10.60 (s, 1H), δ 7.72 (d, J=8.08 Hz, 2H), δ 7.36 (d, J=8.18 Hz, 2H), δ 6.41 (s, 1H), δ 3.73 (s, 6H), δ 3.41 (s, 3H), δ 3.33 (s, 3H) δ 2.55 (m, 4H), δ 1.23 (m, 4H), δ 1.03 (m, 4H).

Figure 5:
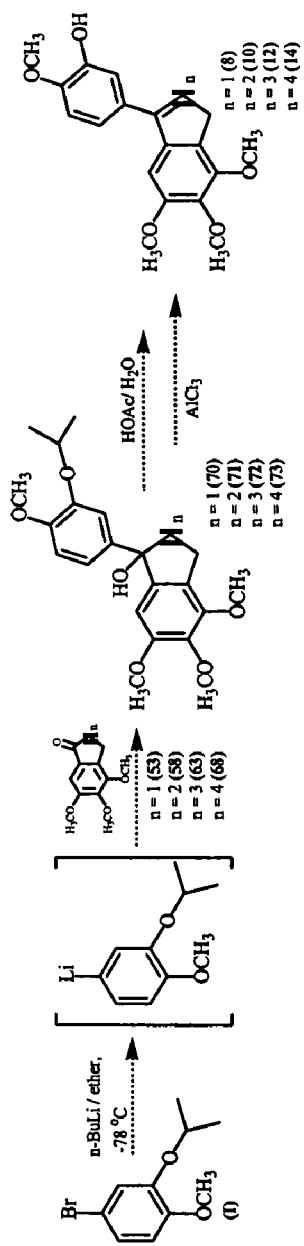
FIG. 5 depicts a route for the synthesis of Compounds 7, 8, 9, 10, 11, 12, 13 and 14, exemplary compounds of the invention.
Figure 5:
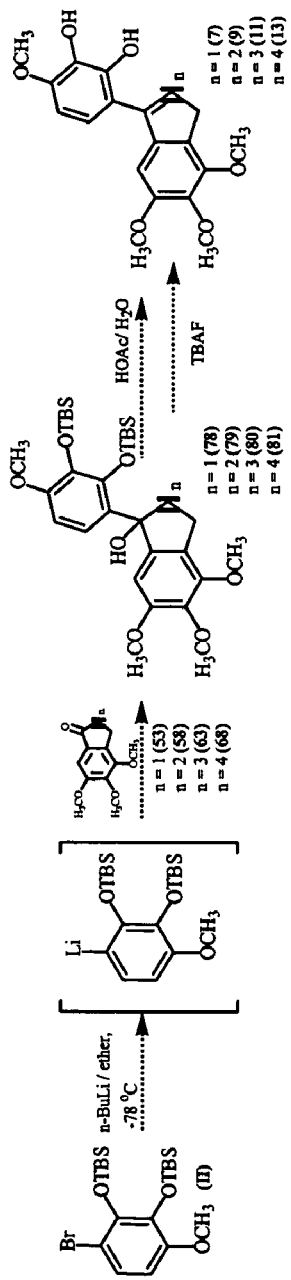
Figure 6:
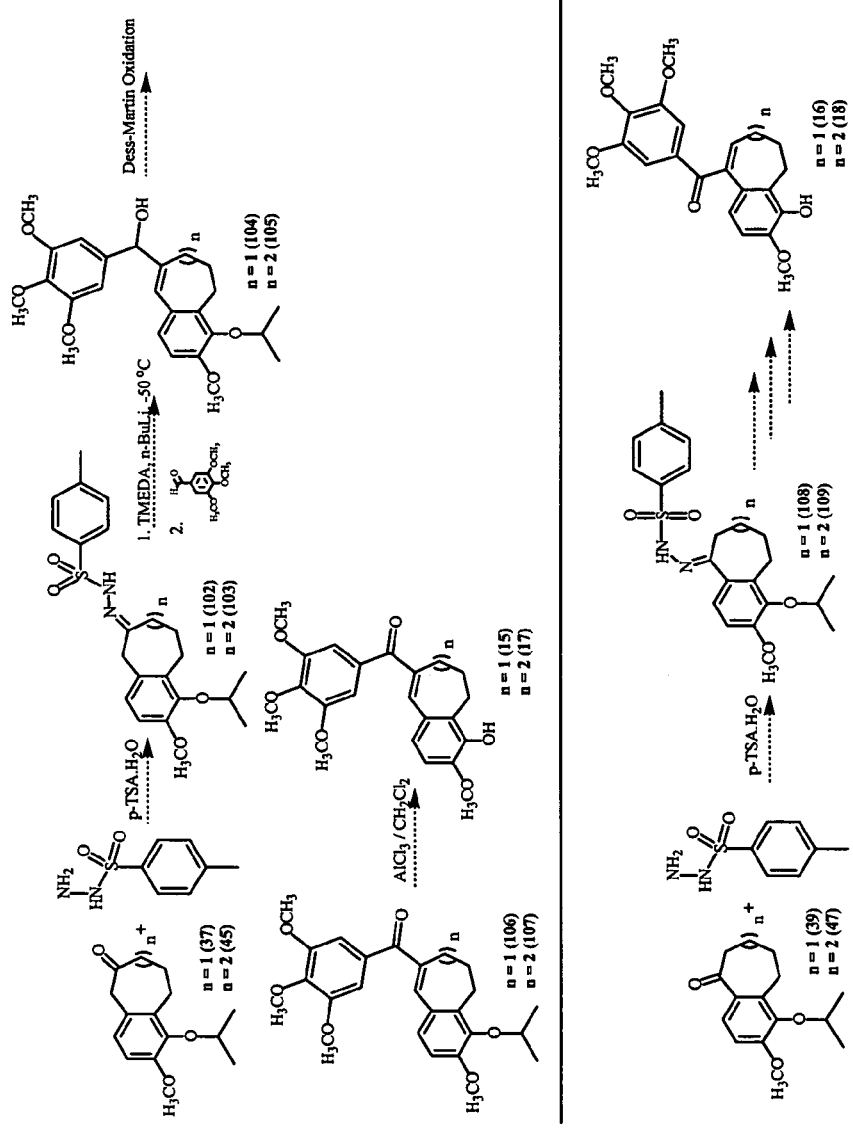
FIG. 6 depicts a route for the synthesis of Compounds 15, 16, 17 and 18, exemplary compounds of the invention.
Figure 7:
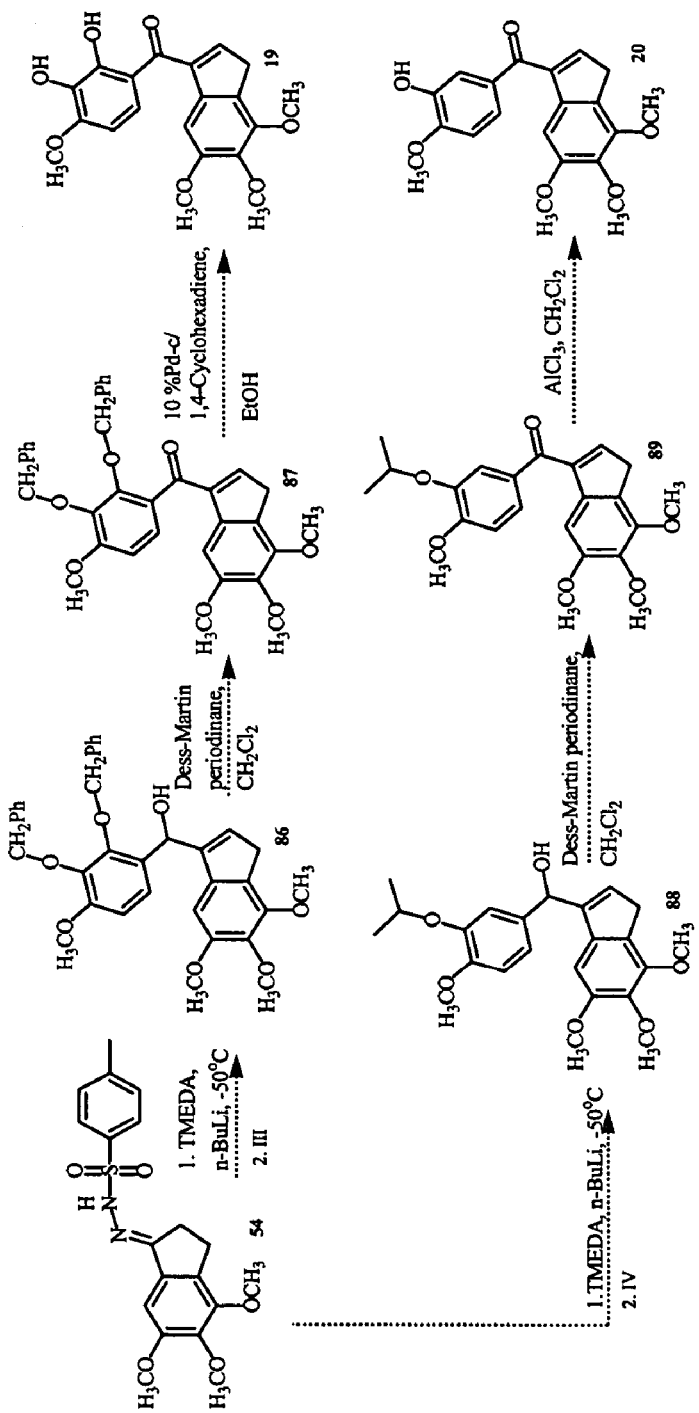
FIG. 7 depicts a route for the synthesis of Compounds 19 and 20, exemplary compounds of the invention.

FIG. 5 (lower panel) depicts a route for the synthesis of Compound 9.

Figure 3:
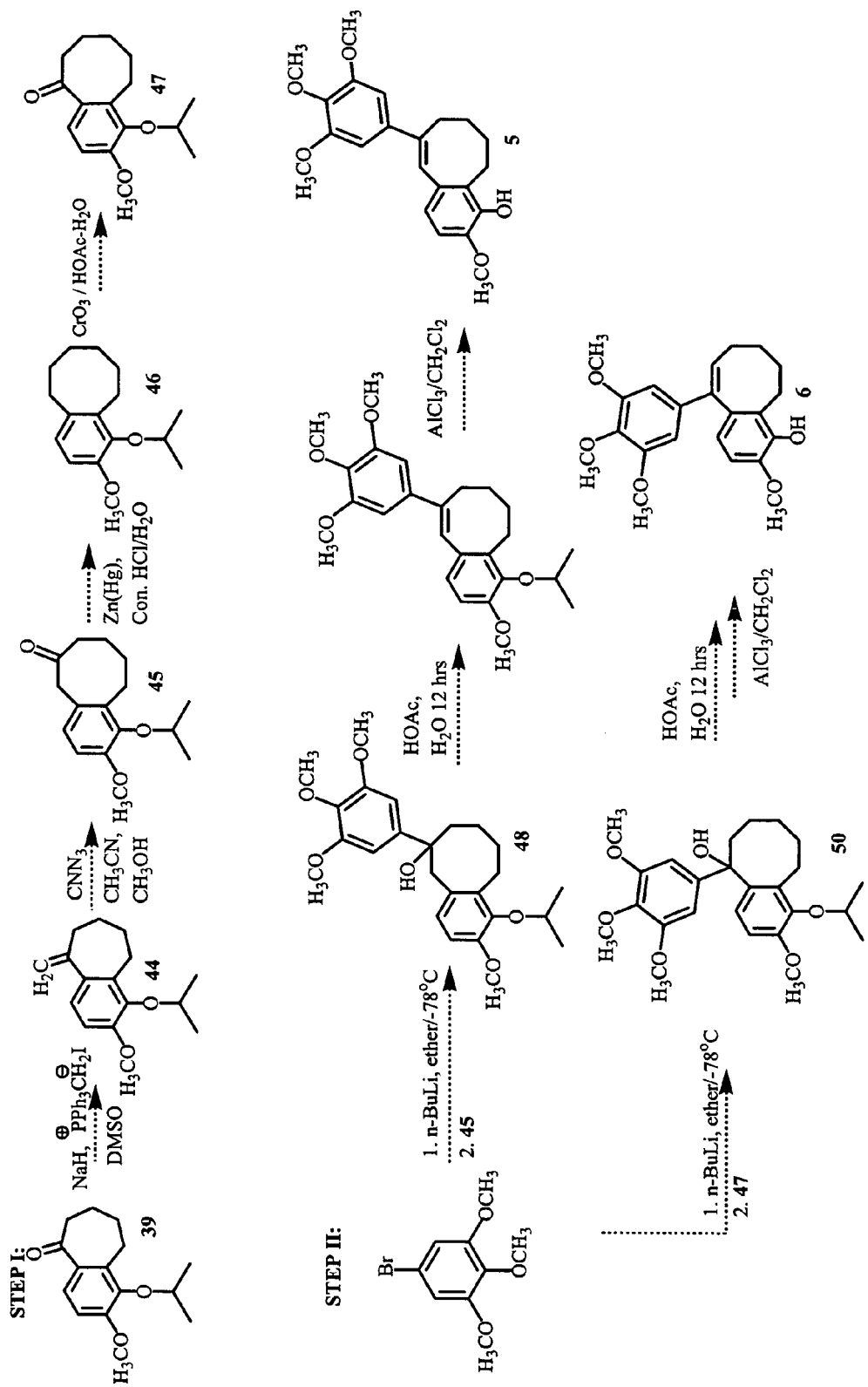
FIG. 3 depicts a route for the synthesis of Compounds 5 and 6, exemplary compounds of the invention.

FIG. 3 depicts a route for the synthesis of Compound 5.

FIG. 5 (upper panel) depicts a route for the synthesis of Compound 10.

Example 3

Figure 11:
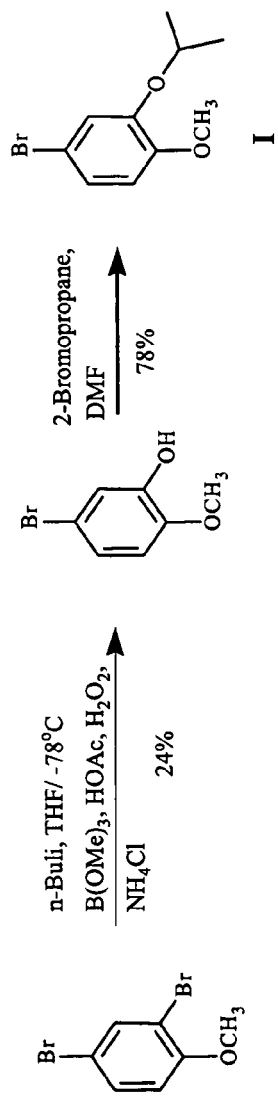
FIG. 11 depicts a route for the synthesis of intermediate I, an intermediate used in the preparation of some of compounds of the invention.
Figure 12:
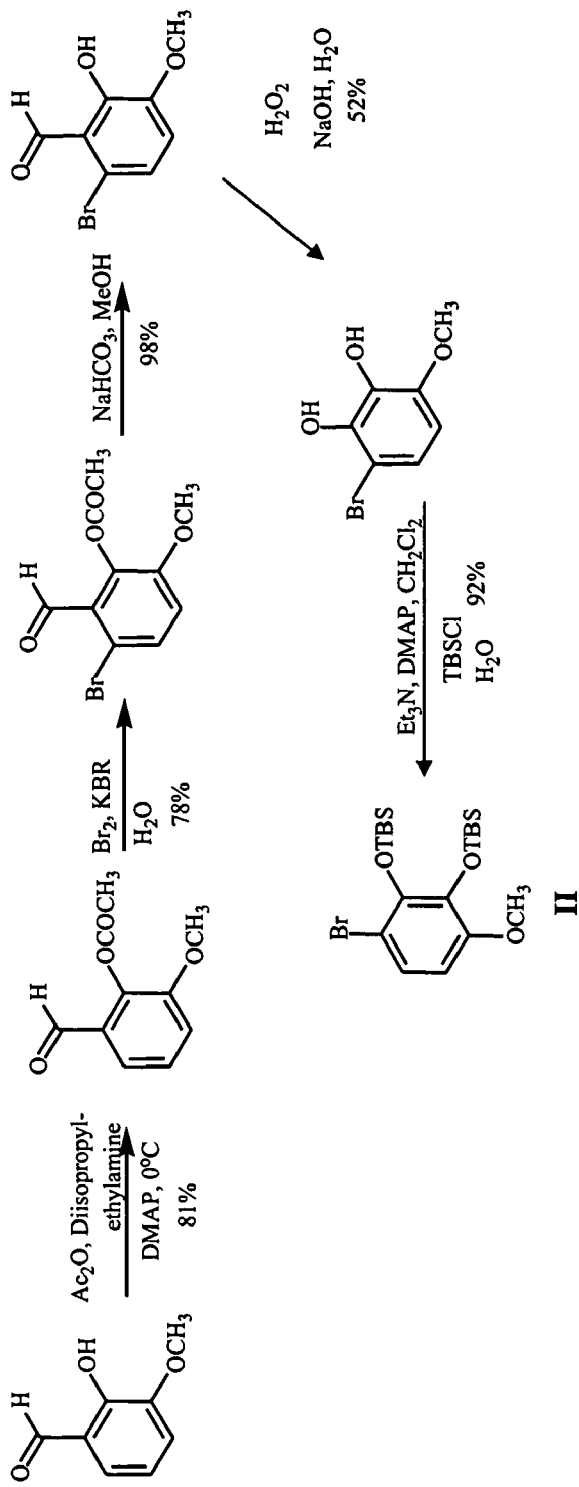
FIG. 12 depicts a route for the synthesis of intermediate II, an intermediate used in the preparation of some of compounds of the invention.
Figure 13:
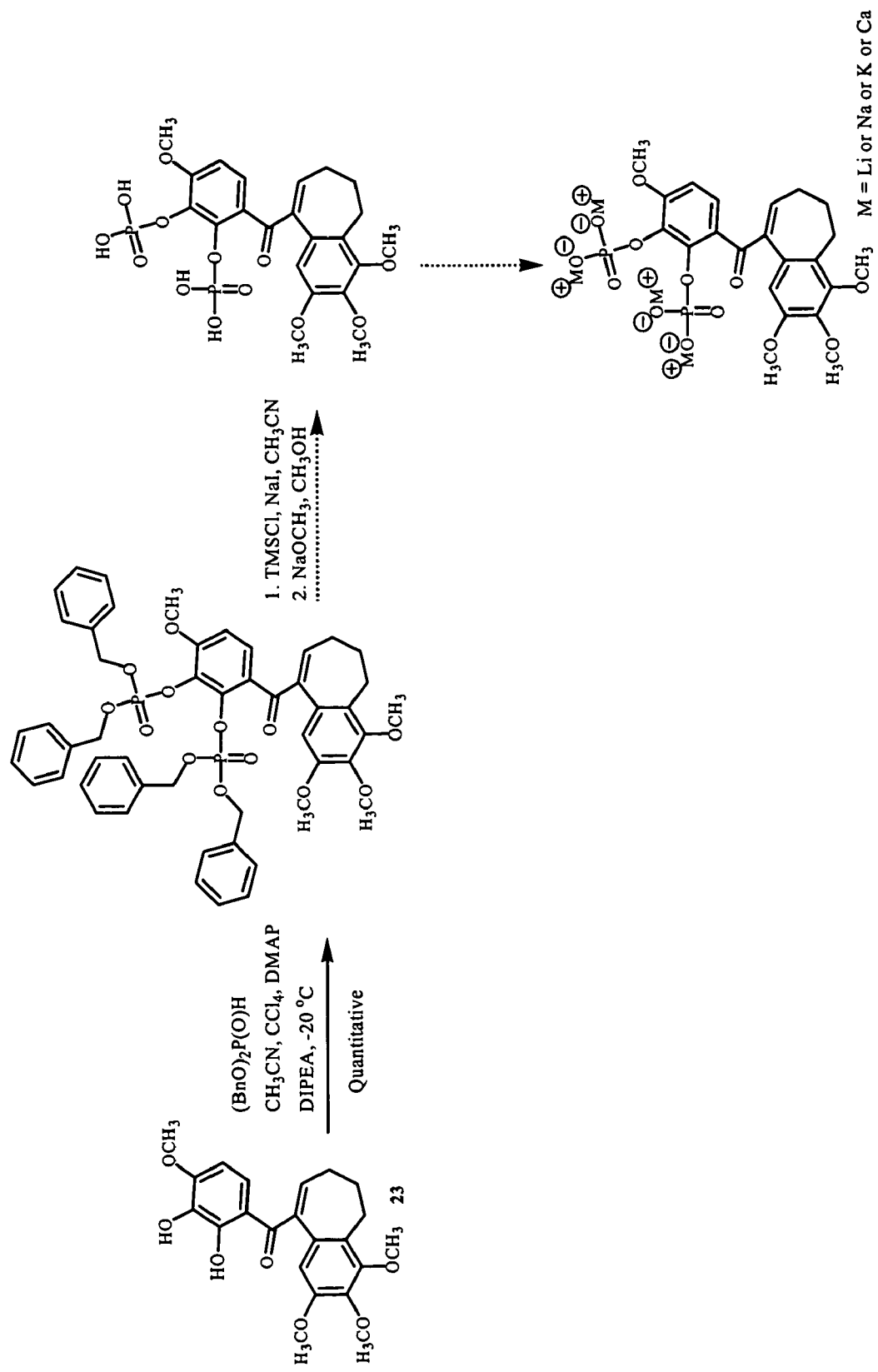
FIG. 13 depicts a route for the synthesis of an exemplary phosphate prodrug of the invention and pharmaceutically acceptable salts thereof.

Synthesis of Intermediate I (FIG. 11)

3-hydroxy,4-methoxybromobenzene

In a 500 mL round bottom flask was charged 2,4-dibromoanisole (5.0 g, 18.8 mmol) followed by 200 mL of dry tetrahydrofuran under nitrogen. The reaction mixture was then cooled to −78° C., and n-butyllithium (16.11 mL, 22.56 mmol) was added dropwise. The reaction mixture was stirred for 30 min at −78° C. The reaction mixture was then warmed to 0° C. and trimethylborate (2.57 mL, 22.56 mmol) was added dropwise. The reaction mixture was stirred at room temperature for 30 min. 5 mL of glacial acetic acid was added followed by 10 mL of 35% wt. hydrogen peroxide in a drop wise fashion. The reaction was allowed to stir 12 h at room temperature. The reaction was quenched with 1 N HCl, extracted with ethylacetate (100×3) and the combined organic phases were dried over Na$_2$SO$_4$, filtered and evaporated under reduced pressure. Purification by column chromatography yielded 1 g (26%) of 3-hydroxy, 4-methoxybromobenzene (white crystals). (96:4 Hexanes:ethylacetate).

Example 4

Inhibition of Tubulin Polymerization

IC$_{50}$ values for tubulin polymerization were determined according to a previously described procedure (Bai et al., Cancer Research, 1996) and are summarized in Table 3 below. Purified tubulin is obtained from bovine brain cells as previously described (Hamel and Lin, Biochemistry, 1984). Various amounts of inhibitor were preincubated for 15 minutes at 37° C. with purified tubulin. After the incubation period, the reaction was cooled and GTP was added to induce tubulin polymerization. Polymerization was then monitored in a Gilford spectrophotometer at 350 nm. The final reaction mixtures (0.25 ml) contained 1.5 mg/ml tubulin, 0.6 mg/ml microtubule-associated proteins (MAPs), 0.5 mM GTP, 0.5 mlM MgCl$_2$, 4% DMSO and 0.1M 4-morpholineethanesulfonate buffer (MES, pH 6.4). IC50 is the amount of inhibitor needed to inhibit tubulin polymerization 50% with respect to the amount of inhibition that occurs in the absence of inhibitor.

TABLE 3

| In vitro inhibition of tubulin polymerization: | |
|---|---|
| Compound | IC50 (μM) |
| CA-4 | 0.73 |
| 1 | ~40 |
| 2 | 1.4 ± 0.2 |
| 3 | ~40 |
| 23 | ~40 |
| 24 | ~40 |

Example 5

In vitro Cytotoxicity Activity Against Cancer Cell Lines

Newly prepared compounds were evaluated for cytotoxic activity against a variety of cell lines derived from human tumors using an assay system similar to the National Cancer Institute procedure previously described (Monks et al., J. Natl. Cancer Inst., 1991). Briefly, the cell suspensions, diluted according to the particular cell type and the expected target cell density (5,000-40,000 cells per well based on cell growth characteristics), were added by pipet (100 ul) to 96-well microtiter plates. Inoculates were allowed a preincubation time of 24-28 hours at 37 C for stabilization. Incubation with the inhibitor compounds lasted for 48 hours in 5% $CO_2$ atmosphere and 100% humidity. Determination of cell growth was performed by in situ fixation of cells, followed by staining with a protein-binding dye sulforhodamine B (SRB), which binds to the basic amino acids of cellular macromolecules. The solubilized stain was measured spectrophotometrically.

Several compounds were evaluated for cytotoxic activity against human P388 leukemia cell lines. The effective dose or ED50 value (defined as the effective dosage required for inhibition of 50% of cell growth) was measured. These and additional compounds were evaluated in terms of growth inhibitory activity against several other human cancer cell lines including: central nervous system ("CNS", SF-268), pancreas (BXPC-3), non-small cell lung cancer ("lung-NSC", NCI-H460), breast (MCF-7), colon (KM20L2), ovarian (OVCAR-3), and prostate (DU-145). The results are described in Table 4 below. The growth inhibition GI50 (defined as the dosage required for inhibition of tumor cell growth by 50%) is listed for each cell line.

vascular shutdown is expressed as vessel area ($mm^2$) per tumor tissue area ($mm^2$) as a percentage of the control ("% VAPM").

Example 7

Evaluation of Tumor Growth Control in vivo by Hollow Fiber Assay

Human tumor cells are grown in polyvinylidene fluoride (PVDF) hollow fibers and each cell line is injected into the mice intraperitoneal (IP) and subcutaneous (SC) membrane compartments. Mice are injected intraperitoneally with two different test doses of compound. Control animals are injected with the diluent. A formazan dye (MTT) conversion assay is used to determine viable cell mass for the assessment of the anti-cancer effects of the ligand. The % T/C is calculated using average optical density of the compound treated sample divided by the average optical density of the control animals.

Alternative Embodiments

All of the compositions and methods disclosed and claimed herein can be made and executed without undue experimentation in light of the present disclosure. While the compositions and methods of this invention have been described in terms of preferred embodiments, it will be appar-

TABLE 4

In vitro Cytotoxicity against Human Cancer Cell Lines

| Compound | ED50 (μM/mL) for cell line | GI50 (μM/mL) for Cell Line | | | | | |
|---|---|---|---|---|---|---|---|
| | P388 | SF-268 | BXP-3 | NCI-H460 | MCF-7 | KM20L2 | DU-145 |
| 1 | 0.51 | 0.28 | 0.40 | 0.23 | 0.32 | 0.20 | 0.33 |
| 2 | 7.4 | >10 | >10 | >10 | >10 | >10 | >10 |
| 23 | 0.029 | 0.0090 | 0.017 | 0.023 | 0.0059 | 0.031 | 0.026 |

Example 6

Inhibition of Tumor Blood Flow

The antivascular effects of the compounds of the invention are assessed in tumor-bearing mice using a Fluorescent Bead Assay. A MHEC-5T hemangioendothelioma tumor model is established by subcutaneous injection of 0.5×106 cultured transformed cell murine myocardial vascular endothelial cell line ("MHEC5-T") cells into the right flank of Fox Chase CB-17 Severe Combined Immunodeficient ("SCID") mice. When transplanted tumors reach a size of 500 $mm^3$ (a size without development of necrosis), the mice receive a single intraperitoneal (i.p.) injection of saline control or compound at doses ranging from 0.1 to 50 mg/kg. At 24 hours post-treatment, mice are injected intravenously with 0.25 ml of diluted FluoSphere beads (1:6 in physiological saline) in the tail vein, sacrificed after 3 minutes, and tumor is excised for cryosectioning. Tumor cryosections at a thickness of 8 um is directly examined using quantitative fluorescent microscopy. Blood vessels are indicated by blue fluorescence from injected beads. For quantification, image analysis of 3 sections from three tumors treated in each group is examined and ent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

It should be readily apparent to any practitioner skilled in the art that there are various ways of appending trimethoxyaryl and trimethoxyaroyl groups around a Combrestatin analog molecular scaffold in a manner which will result in a similar molecular conformation capable of undergoing pseudo pi-pi stacking. In addition, although the trimethoxyaryl motif seems optimal for enhanced tubulin binding, it is also very possible that another combination of alkoxy substituents (such as ethoxy, propoxy, isopropoxy, allyloxy, etc.) either as a trisubstituted pattern or as disubstituted (with one type of alkoxy moiety) and monosubstituted (with a different alkoxy moiety), or with three distinct types of alkoxy moieties may also have good tubulin binding characteristics. It is also conceivable that instead of having aryl alkoxy groups, it may be possible to substitute simply aryl-alkyl and aryl-alkenyl moieties and still maintain the enhanced cytotoxicity profile. Phenolic groups may also have activity on these described chromene ligands. The synthesis of any of these modified chromene-ligands will be very straight-forward for anyone skilled in the art, and often will only involve a different choice of initial starting materials. To prepare these alternative ligands, the same synthetic schemes as disclosed herein or similar schemes with only slight modifications may be employed.

What is claimed is:

1. A compound of the Formula IV:

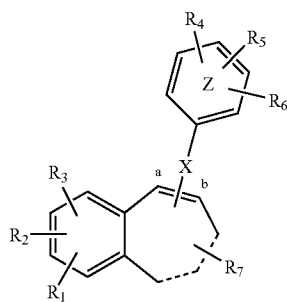

(IV)

or a pharmaceutically acceptable salt thereof, wherein
the dashed lines independently indicate a single or double bond;
X is C(O);
$R_1$, $R_2$, $R_3$, $R_4$, $R_5$, $R_6$ and $R_7$ are each, independently, selected from the group consisting of H, halogen, lower alkyl, lower alkoxy, hydroxyl, amine, phosphate, phosphoramidate, and amino acid acyl group; and
phenyl ring "Z" is bonded to either carbon "a" or "b."

2. The compound of claim 1, wherein the compound of Formula IV is selected from the group consisting of (15) (1-Hydroxy-2-methoxy-8,9-dihydro-7H-benzocyclohepten-6-yl)-(3,4,5-trimethoxy-phenyl)-methanone; (16) (1-Hydroxy-2-methoxy-8,9-dihydro-7H-benzocyclohepten-5-yl)-(3,4,5trimethoxy-phenyl)-methanone; (23) (2,3-Dihydroxy-4-methoxy-phenyl)-(1,2,3-trimethoxy-8,9-dihydro-7H-benzocyclohepten-5-yl)-methanone, and (24) (3-Hydroxy-4-methoxy-phenyl)-(1,2,3-trimethoxy-8,9-dihydro-7Hbenzocyclohepten-5-yl)-methanone.

3. A compound of the Formula I:

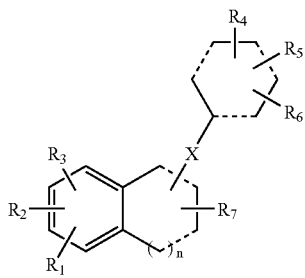

(I)

or a pharmaceutically acceptable salt thereof,
wherein
the dashed lines indicate a single or double bond;
$R_1$, $R_2$, $R_3$, $R_4$, $R_5$, $R_6$ and $R_7$ are each, independently, selected from the group consisting of H, halogen, lower alkyl, lower alkoxy, hydroxyl, amine, phosphate, phosphoramidate, and amino acid acyl group;
X is C(O); and
n is 2.

4. The compound of claim 3, wherein the ring-substituted bicyclic fused ring system is represented by a compound of the Formula II:

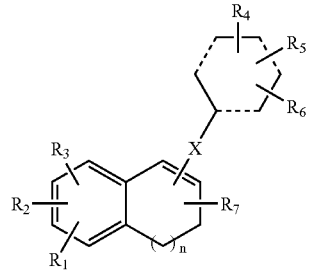

(II)

or a pharmaceutically acceptable salt thereof, wherein
the dashed lines indicate a single or double bond;
$R_1$, $R_2$, $R_3$, $R_4$, $R_5$, $R_6$ and $R_7$ are each, independently, selected from the group consisting of H, halogen, lower alkyl, lower alkoxy, hydroxyl, amine, phosphate, phosphoramidate, and amino acid acyl group;
X is C(O); and
n is 2.

5. A compound of claim 1 of the Formula IIa:

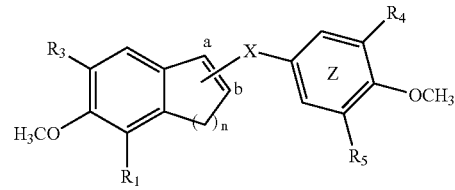

(IIa)

or a pharmaceutically acceptable salt thereof, wherein
phenyl ring "Z" is bonded to either carbon "a" or "b";
$R_1$, $R_3$, $R_4$ and $R_5$ are each, independently, selected from the group consisting of H, lower alkoxy and hydroxyl;
X is C(O); and
n is 3.

6. A compound of claim 1 of the Formula IIb:

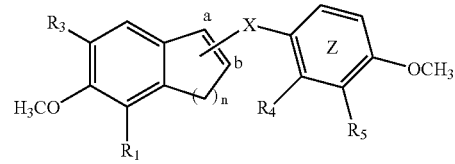

(IIb)

or a pharmaceutically acceptable salt thereof, wherein
phenyl ring "Z" is bonded to either carbon "a" or "b";
$R_1$, $R_3$, $R_4$ and $R_5$ are each, independently, selected from the group consisting of H, lower alkoxy and hydroxyl;
X is C(O); and
n is 3.

7. The compound of claim 1, wherein Z is bonded to carbon "a."

8. The compound of claim 1, wherein Z is bonded to carbon "b."

9. The compound of claim 1, wherein at least one of $R_1$-$R_6$ is lower alkoxy.

10. The compound of claim 1, wherein $R_7$ is H.

11. The compound of claim 3, wherein at least one of $R_1$-$R_6$ is lower alkoxy.

12. The compound of claim 3, wherein $R_7$ is H.

13. The compound of claim 5, wherein Z is bonded to carbon "a."

14. The compound of claim 6, wherein Z is bonded to carbon "a."

15. The compound of claim 6, wherein Z is bonded to carbon "b."

* * * * *